United States Patent
Mueller et al.

(10) Patent No.: US 11,707,495 B2
(45) Date of Patent: Jul. 25, 2023

(54) RECOMBINANT RHABDOVIRUS ENCODING FOR CCL21

(71) Applicants: Boehringer Ingelheim International GmbH, Ingelheim am Rhein (DE); ViraTherapeutics GmbH, Rum (AT)

(72) Inventors: Philipp Mueller, Mittelbiberach (DE); Klaus Erb, Mittelbiberach (DE); Patrik Erlmann, Goetzens (AT); Tobias Friederike Nolden, Birgitz (AT); John Edward Park, Warthausen (DE); Guido Wollmann, Innsbruck (AT)

(73) Assignees: Boehringer Ingelheim International GmbH, Ingelheim am Rhein (DE); ViraTherapeutics GmbH, Rum (AT)

( * ) Notice: Subject to any disclaimer, the term of this patent is extended or adjusted under 35 U.S.C. 154(b) by 554 days.

(21) Appl. No.: 16/751,364

(22) Filed: Jan. 24, 2020

(65) Prior Publication Data

US 2020/0237838 A1  Jul. 30, 2020

(30) Foreign Application Priority Data

Jan. 25, 2019 (EP) .................... 19153668

(51) Int. Cl.
| | |
|---|---|
| A61K 35/766 | (2015.01) |
| C12N 7/00 | (2006.01) |
| A61K 35/00 | (2006.01) |
| A61K 31/4375 | (2006.01) |
| A61P 35/00 | (2006.01) |
| A61K 9/00 | (2006.01) |
| A61K 31/4704 | (2006.01) |
| A61K 31/4725 | (2006.01) |
| A61K 31/506 | (2006.01) |
| A61K 31/5377 | (2006.01) |
| A61K 39/395 | (2006.01) |
| C07K 14/52 | (2006.01) |

(52) U.S. Cl.
CPC .......... *A61K 35/766* (2013.01); *A61K 9/0019* (2013.01); *A61K 31/4375* (2013.01); *A61K 31/4704* (2013.01); *A61K 31/4725* (2013.01); *A61K 31/506* (2013.01); *A61K 31/5377* (2013.01); *A61K 39/3955* (2013.01); *A61P 35/00* (2018.01); *C07K 14/521* (2013.01); *C12N 7/00* (2013.01); *C12N 2760/20221* (2013.01)

(58) Field of Classification Search
None
See application file for complete search history.

(56) References Cited

U.S. PATENT DOCUMENTS

| | | | |
|---|---|---|---|
| 10,265,357 | B2 | 4/2019 | Laer et al. |
| 2010/0260798 | A1 | 10/2010 | Fabre et al. |
| 2014/0301992 | A1* | 10/2014 | Laer ..................... A61K 35/766 |
| | | | 514/44 R |

FOREIGN PATENT DOCUMENTS

| | | |
|---|---|---|
| WO | 9706243 A1 | 2/1997 |
| WO | 2007123961 | 11/2007 |
| WO | 2010040526 | 4/2010 |
| WO | 2017143449 | 8/2017 |
| WO | 2017197525 | 11/2017 |

OTHER PUBLICATIONS

Sharma et al. CCL21 Chemokine Therapy for Lung Cancer. Int Trends Immun. Jan. 2013 ; 1(1): 10-15.*
Li et al. CCL21/IL21-armed oncolytic adenovirus enhances antitumor activityagainst TERT-positive tumor cells. Virus Research 220 (2016) 172-178.*
GenBank: AAH27918.1. Chemokine (C-C motif) ligand 21 [*Homo sapiens*]. Dated Jul. 15, 2006.*
GenBank: J02428.1. Vesicular stomatitis Indiana virus, complete genome. Dated Oct. 21, 2002.*
NCT03546361. CCL21-Gene Modified Dendritic Cell Vaccine and Pembrolizumab in Treating Patients With Stage IV Non-small Cell Lung Cancer. Publication of clinical trial. First posted on Jun. 6, 2018. https://www.clinicaltrials.gov/ct2/show/NCT03546361.*
Hjorto et al. Differential ccr7 Targeting in Dendritic cells by Three naturally Occurring cc-chemokines. Front. Immunol., 2016, 7:568.*
International Search Report and Written Opinion dated Mar. 3, 2020 for PCT/EP2020/051701.
Galivo, Interference of CD40L-Mediated Tumor Immunotherapy by Oncolytic Vesicular Stomatitis Virus, Human Gene Therapy, vol. 21, 2010.
Barmore, Transferring the C-terminus of the chemokine CCL221 to CCL19 confers enhanced heparin binding, Biochemical Research Comm., vol. 477, 2016.
Ausbel, Current good Manufacturing practice production of an oncolytic recombinant vesicular stomatitis viral vector for cancer treatment, Human gene therapy, vol. 22, 2011.
Gagnon, The emerging generation of chromatography tools for virus purification, Bioprocess international, vol. 6, 2008.

* cited by examiner

*Primary Examiner* — Nianxiang Zou
(74) *Attorney, Agent, or Firm* — Wendy M. Gombert

(57) ABSTRACT

The present invention relates to the field of oncolytic viruses and in particular to a recombinant rhabdovirus, such as vesicular stomatitis virus encoding in its genome for a CCL21 protein. The invention is further directed to the use of the recombinant virus in the treatment of cancer, and also to methods for producing such viruses.

34 Claims, 28 Drawing Sheets

Specification includes a Sequence Listing.

FIG. 2A-D
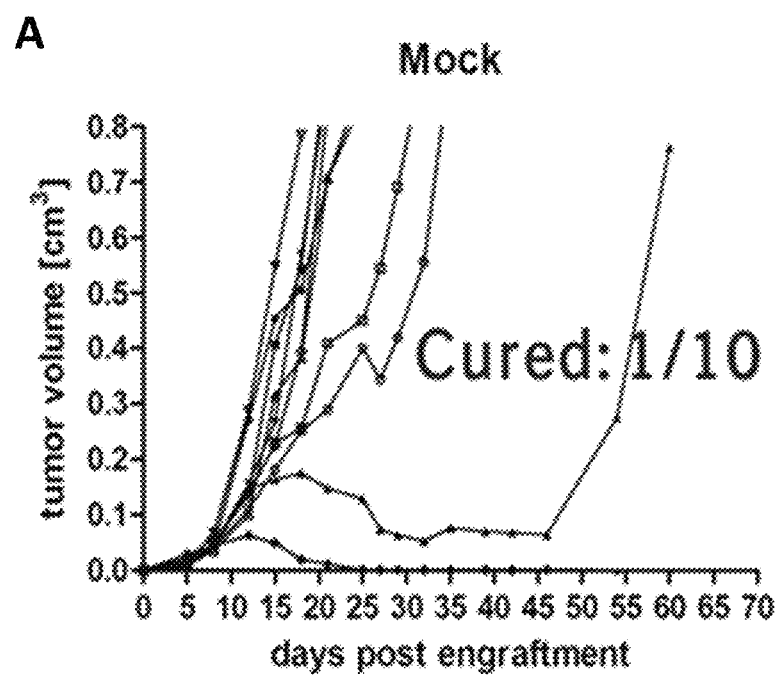
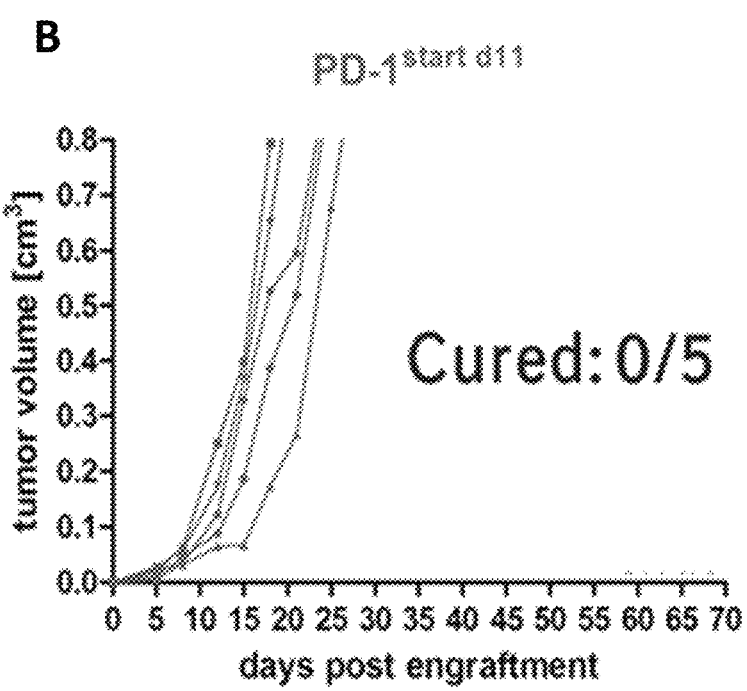

FIG. 2A-D cont.
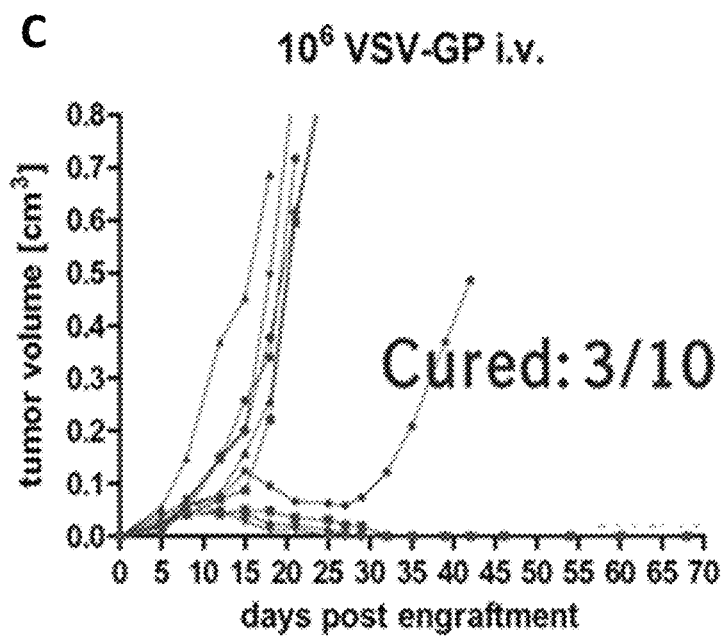
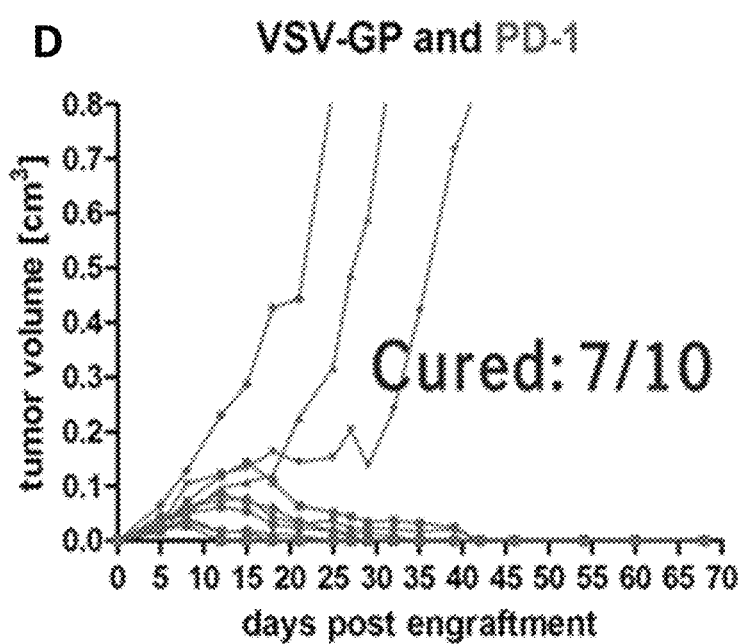

FIG. 3A-C
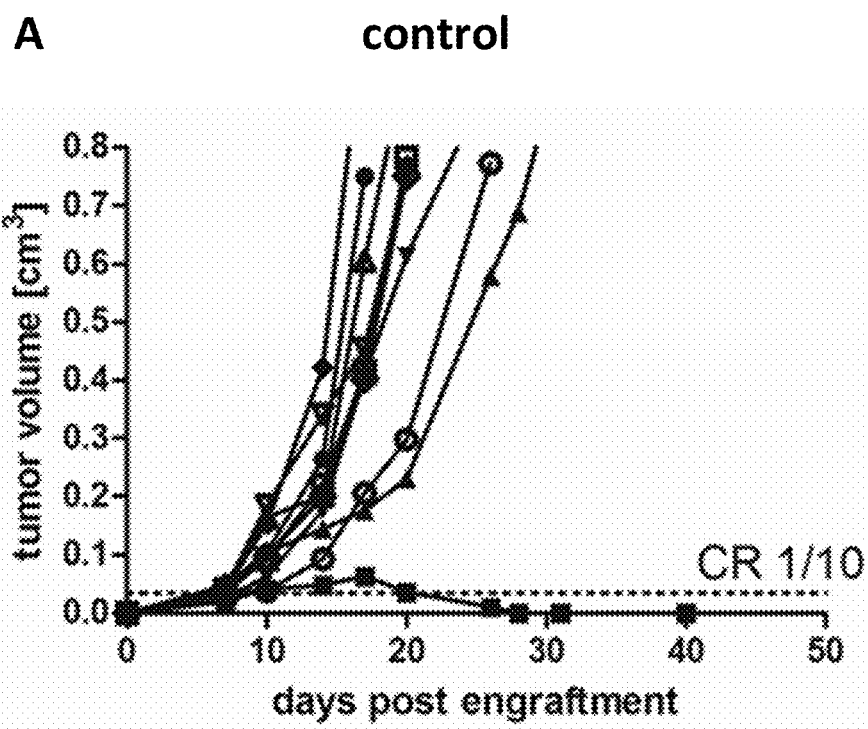
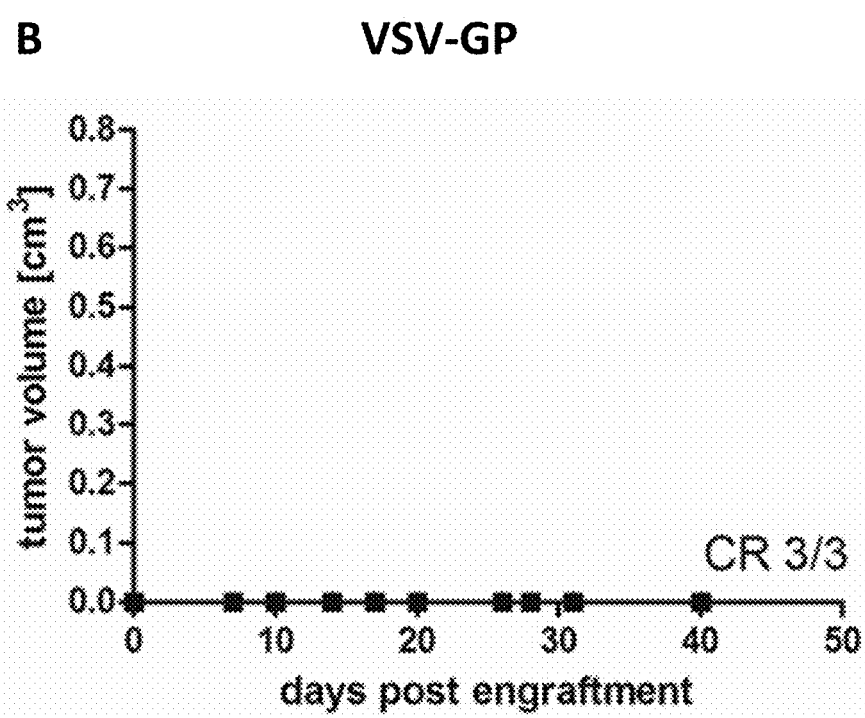

FIG. 3A-C cont.
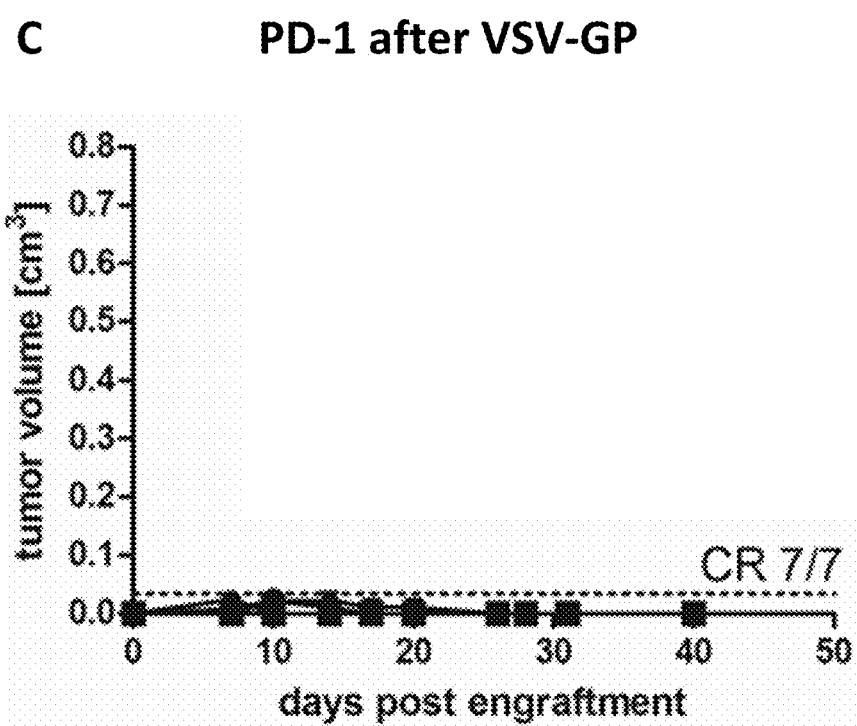

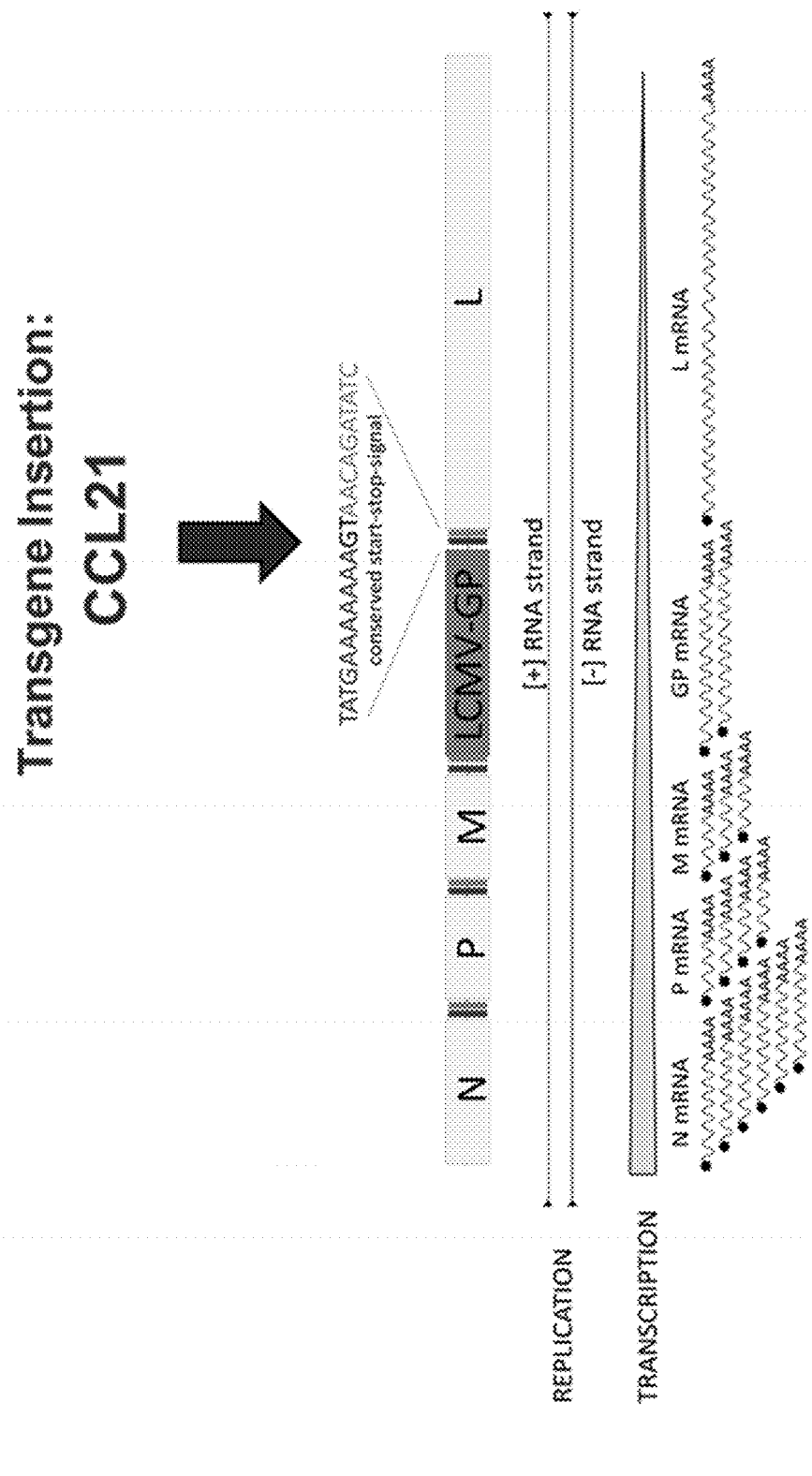
FIG. 5A-B

FIG. 5A-B cont.
B
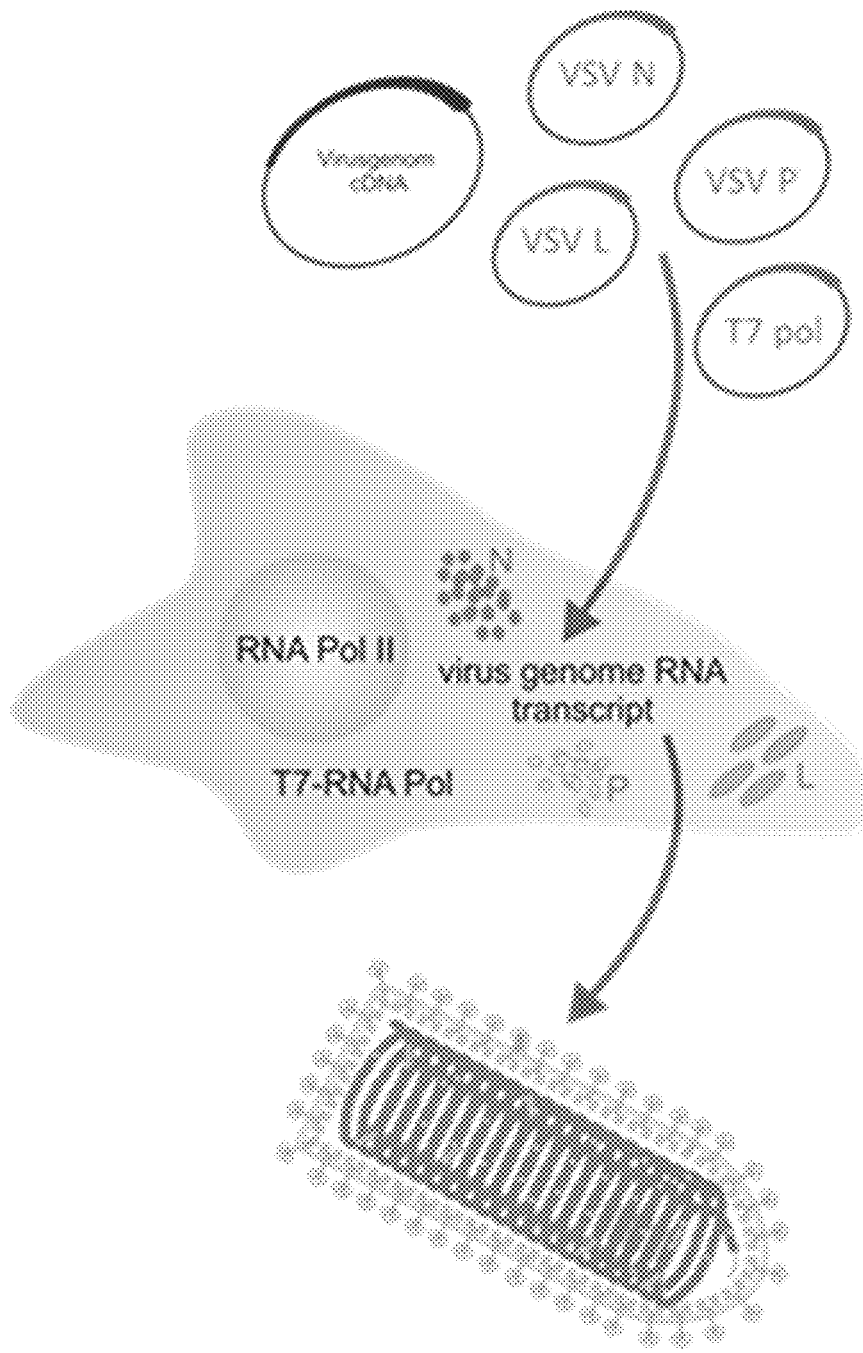

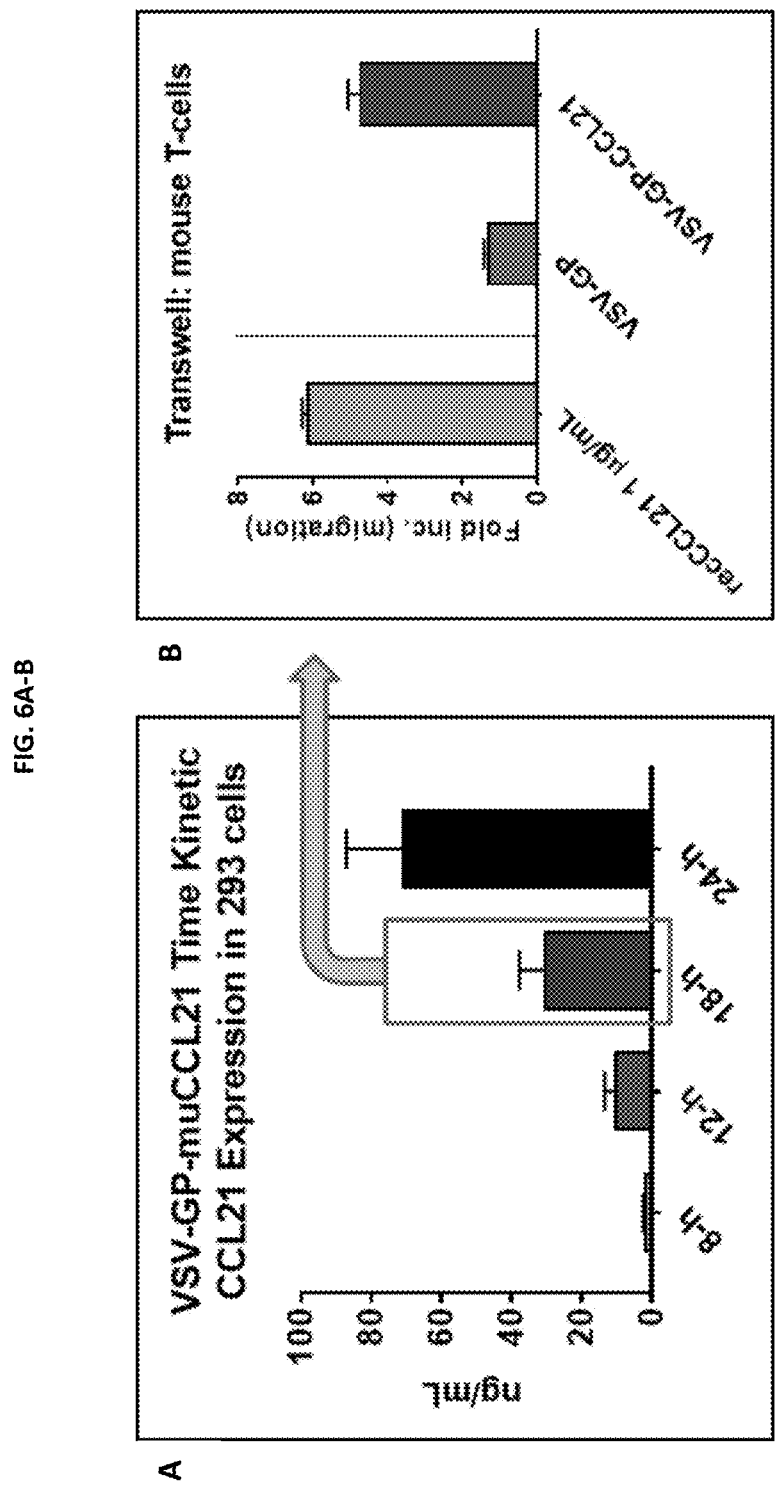
FIG. 6A-B

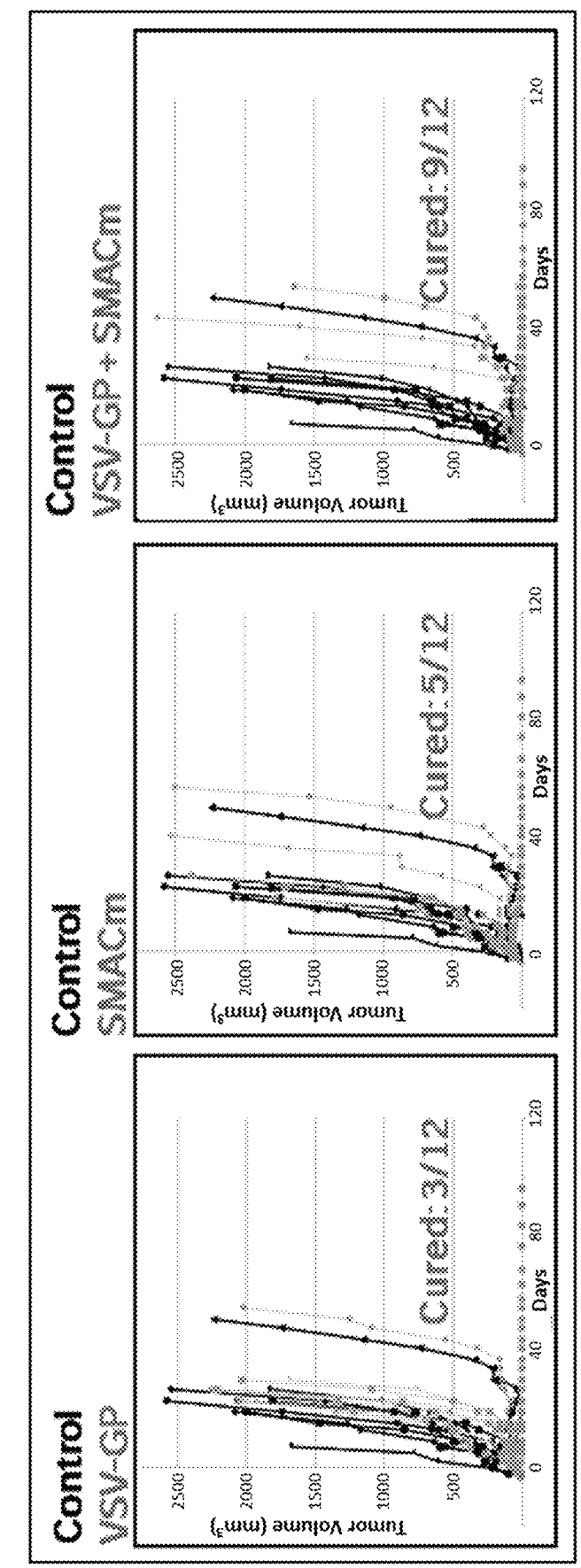
FIG. 7A-C

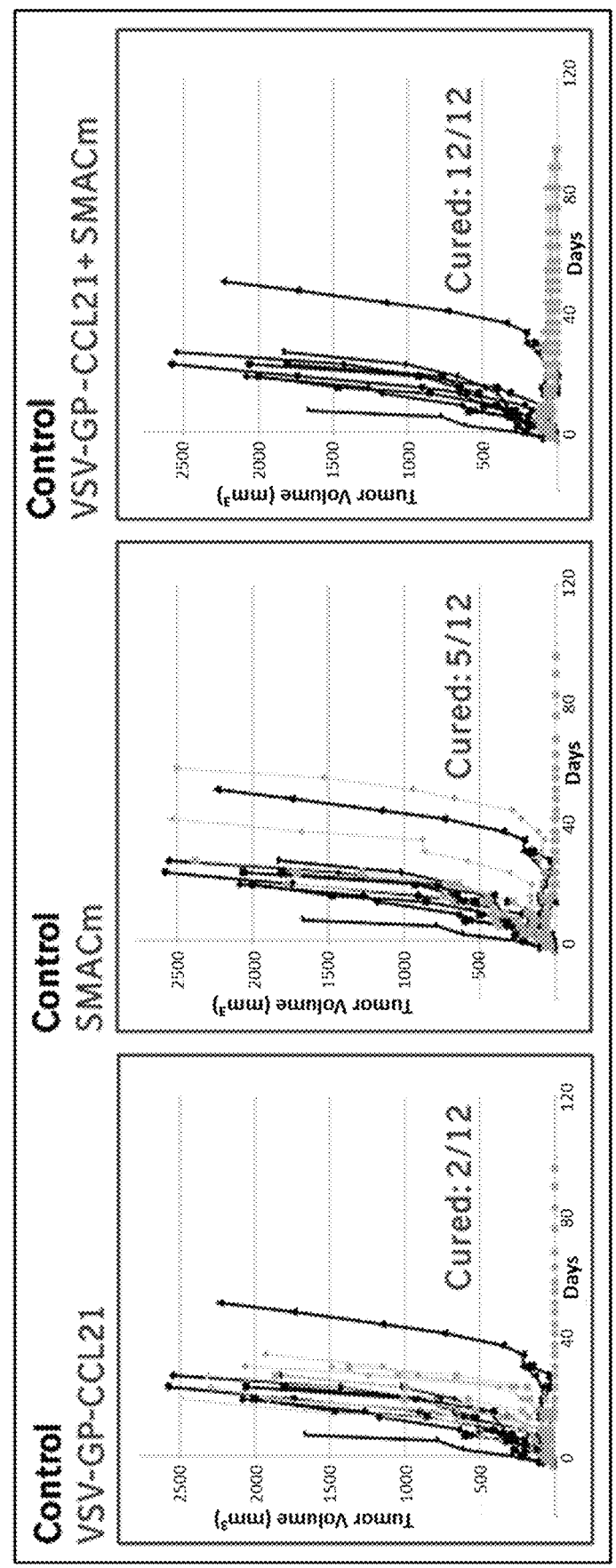
FIG. 8A-C

FIG. 19A-C
A
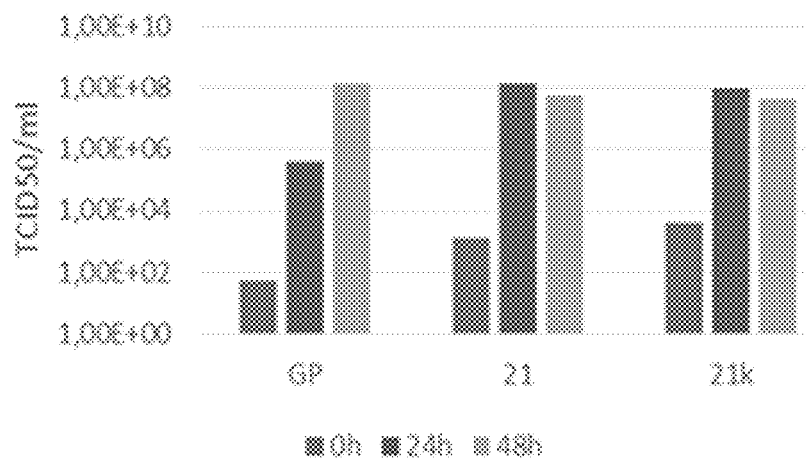
B
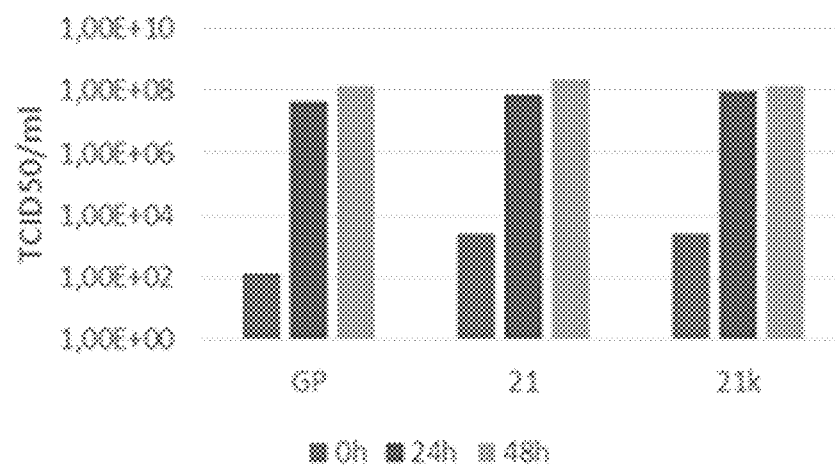

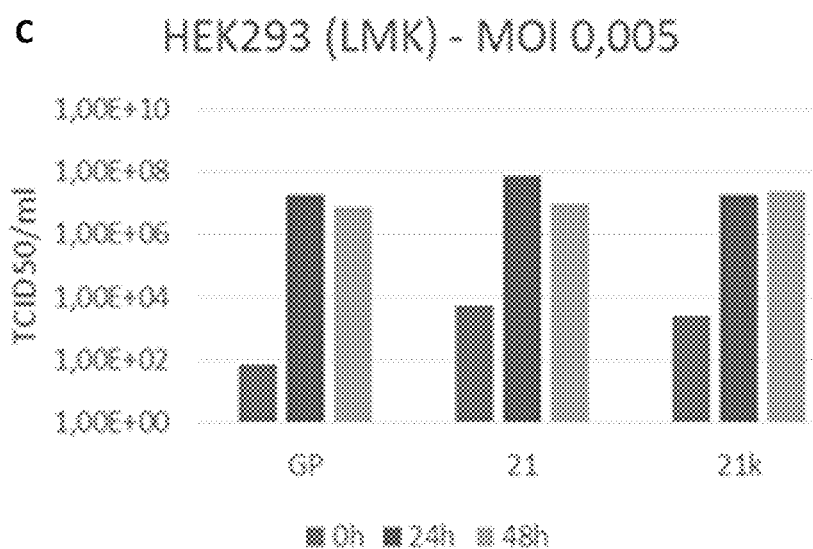
FIG. 19A-C cont.

FIG. 21

RECOMBINANT RHABDOVIRUS ENCODING FOR CCL21

FIELD OF THE INVENTION

The present invention relates to the field of oncolytic viruses and in particular to a recombinant rhabdovirus encoding in its genome for a CCL21 protein. The invention is further directed to the use of the recombinant rhabdovirus in the treatment of cancer, and also to methods for producing such viruses.

BACKGROUND OF THE INVENTION

Oncolytic viruses are an emerging class of biologicals which selectively replicate in and kill cancer cells and are able to spread within tumors. Efforts to further improve oncolytic viruses to increase their therapeutic potential has led to the development of so called armed viruses, which encode in their genome tumor antigens or immune modulatory transgenes to improve their efficacy in tumor treatment.

In many cases there is a paucity of T cells in tumors and therefor there exists what has become known as "immune deserts"—a tumor microenvironment where the immune system's T cells cannot or do not penetrate the tumor to kill the cells growing out of control. It has been postulated that to evade immune surveillance, tumors create an immunosuppressive microenvironment by recruiting myeloid-derived suppressor cells or secrete factors including TGFβ, which play a dual role of inducing the expression of extracellular matrix genes and suppressing the expression of chemokines and cytokines required to facilitate T-cell infiltration into tumors (Pickup M, Novitskiy S, Moses H L. The roles of TGFbeta in the tumour microenvironment. Nat Rev Cancer 2013; 13:788-99). Furthermore, studies have found that tumors exhibiting high expression of genes which correspond to an immunosuppressive microenvironment are associated with poor outcomes across a number of cancer types, including ovarian cancer and colorectal cancer (Calon A, Lonardo E, Berenguer-Llergo A, Espinet E, Hernando-Momblona X, Iglesias M, et al. Stromal gene expression defines poor-prognosis subtypes in colorectal cancer. Nat Genet 2015; 47:320-9; Ryner L, Guan Y, Firestein R, Xiao Y, Choi Y, Rabe C, et al. Upregulation of periostin and reactive stroma is associated with primary chemoresistance and predicts clinical outcomes in epithelial ovarian cancer. Clin Cancer Res 2015; 21:2941-51; Tothill R W, Tinker A V, George J, Brown R, Fox S B, Lade S, et al. Novel molecular subtypes of serous and endometrioid ovarian cancer linked to clinical outcome. Clin Cancer Res 2008; 14:5198-208.)

One recent approach foresees an oncolytic virus that encodes in its genome the IFN-β protein as a cargo. In a further approach expression of the tumor antigen MAGE-A3 was contemplated. In addition to identifying a suitable and effective cargo, the expression of additional cargos from a viral backbone, always carries the risk that it will not only potentiate anti-tumor efficacy but also anti-viral immunity. Care has to be taken that the cargo does not restrict the oncolytic potential of the virus to a degree where the benefit gained by expression of the therapeutic cargo is negated by the loss of oncolytic potency. Thus, there is a need in the art for further improved armed oncolytic viruses that can be used in effective treatment of tumors. There is further a need in the art to selectively improve T cell and/or dendritic cell infiltration into immunosuppressive tumor microenvironments.

SUMMARY OF THE INVENTION

The present invention addresses the above needs by providing a recombinant rhabdovirus, such as a vesicular stomatitis virus, which encodes in its genome a CCL21 protein or a functional variant thereof, preferably human CCL21.

It is to be understood that any embodiment relating to a specific aspect might also be combined with another embodiment also relating to that specific aspect, even in multiple tiers and combinations comprising several embodiments to that specific aspect.

In a first aspect, the present invention relates to a recombinant rhabdovirus encoding in its genome at least one CCL21 protein or a functional variant thereof.

In one embodiment relating to the first aspect, the CCL21 protein or functional variant thereof is selected from the group comprising: (i) plasmin processed CCL21 protein, (ii) c-terminally truncated CCL21 protein, (iii) a protein comprising SEQ ID NO:2 or having at least 80%, 85%, 90%, 92%, 94%, 96%, 98% or 99% identity to SEQ ID NO:2, (iv) a protein comprising SEQ ID NO:3 or having at least 80%, 85%, 90%, 92%, 94%, 96%, 98% or 99% identity to SEQ ID NO:3, (v) a protein comprising SEQ ID NO:4 or having at least 80%, 85%, 90%, 92%, 94%, 96%, 98% or 99% identity to SEQ ID NO:4, (vi) a protein according to any of (i)-(v) further comprising a signal peptide sequence, (vii) a protein comprising SEQ ID NO:1 or having at least 80%, 85%, 90%, 92%, 94%, 96%, 98% or 99% identity to SEQ ID NO:1, or (viii) a protein comprising SEQ ID NO:5 or having at least 80%, 85%, 90%, 92%, 94%, 96%, 98% or 99% identity to SEQ ID NO:5.

In one embodiment relating to the first aspect, the recombinant rhabdovirus is a vesiculovirus.

In one embodiment relating to the first aspect, the vesiculovirus is selected from the group comprising: vesicular stomatitis alagoas virus (VSAV), carajás virus (CJSV), chandipura virus (CHPV), cocal virus (COCV), vesicular stomatitis Indiana virus (VSIV), isfahan virus (ISFV), maraba virus (MARAV), vesicular stomatitis New Jersey virus (VSNJV), or piry virus (PIRYV), preferably a vesicular stomatitis Indiana virus (VSIV) or preferably a vesicular stomatitis New Jersey virus (VSNJV).

In one embodiment relating to the first aspect, the recombinant rhabdovirus is replication-competent.

In one embodiment relating to the first aspect, the CCL21 protein or functional variant thereof is human CCL21.

In one embodiment relating to the first aspect, the recombinant rhabdovirus lacks a functional gene coding for glycoprotein G, and/or lacks a functional glycoprotein G; or, the gene coding for the glycoprotein G is replaced by the gene coding for the glycoprotein GP of another virus, and/or the glycoprotein G is replaced by the glycoprotein GP of another virus; or, the gene coding for the glycoprotein G is replaced by the gene coding for the glycoprotein GP of an arenavirus, and/or the glycoprotein G is replaced by the glycoprotein GP of an arenavirus. In a further preferred embodiment, the gene coding for the glycoprotein G is replaced by the gene coding for the glycoprotein GP of Dandenong virus or Mopeia virus, and/or the glycoprotein G is replaced by the glycoprotein GP of Dandenong virus or Mopeia virus. Even more preferred, the gene coding for the glycoprotein G is replaced by the gene coding for the glycoprotein GP of lymphocyte choriomeningitis virus (LCMV), and/or the glycoprotein G is replaced by the glycoprotein GP of LCMV.

In a preferred embodiment relating to the first aspect, the invention provides a recombinant vesicular stomatitis virus encoding in its genome at least one CCL21 protein or a functional variant thereof, preferably human CCL21, selected from the group comprising: (i) plasmin processed CCL21 protein, (ii) c-terminally truncated CCL21 protein, (iii) a protein comprising SEQ ID NO:2 or having at least 80%, 85%, 90%, 92%, 94%, 96%, 98% or 99% identity to SEQ ID NO:2, (iv) a protein comprising SEQ ID NO:3 or having at least 80%, 85%, 90%, 92%, 94%, 96%, 98% or 99% identity to SEQ ID NO:3, (v) a protein comprising SEQ ID NO:4 or having at least 80%, 85%, 90%, 92%, 94%, 96%, 98% or 99% identity to SEQ ID NO:4, (vi) a protein according to any of (i)-(v) further comprising a signal peptide sequence, (vii) a protein comprising SEQ ID NO:1 or having at least 80%, 85%, 90%, 92%, 94%, 96%, 98% or 99% identity to SEQ ID NO:1, or (viii) a protein comprising SEQ ID NO:5 or having at least 80%, 85%, 90%, 92%, 94%, 96%, 98% or 99% identity to SEQ ID NO:5, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

In a second aspect, the present invention relates to a recombinant vesicular stomatitis virus, encoding in its genome at least for a vesicular stomatitis virus nucleoprotein (N), large protein (L), phosphoprotein (P), matrix protein (M), glycoprotein (G) and at least one CCL21 protein or a functional variant thereof, preferably human CCL21.

In one embodiment relating to the second aspect, the nucleoprotein (N) comprises an amino acid sequence as set forth in SEQ ID NO:7 or a functional variant at least 80%, 85%, 90%, 92%, 94%, 96%, 98% identical to SEQ ID NO:7.

In one embodiment relating to the second aspect, the phosphoprotein (P) comprises an amino acid sequence as set forth in SEQ ID NO:8 or a functional variant at least 80%, 85%, 90%, 92%, 94%, 96%, 98% identical to SEQ ID NO:8.

In one embodiment relating to the second aspect, the large protein (L) comprises an amino acid sequence as set forth in SEQ ID NO:9 or a functional variant at least 80%, 85%, 90%, 92%, 94%, 96%, 98% identical to SEQ ID NO:9.

In one embodiment relating to the second aspect, the matrix protein (M) comprises an amino acid sequence as set forth in SEQ ID NO:10 or a functional variant at least 80%, 85%, 90%, 92%, 94%, 96%, 98% identical to SEQ ID NO:10.

In a preferred embodiment relating to the second aspect, the nucleoprotein (N) comprises an amino acid sequence as set forth in SEQ ID NO:7 or a functional variant at least 80%, 85%, 90%, 92%, 94%, 96%, 98% identical to SEQ ID NO:7, the phosphoprotein (P) comprises an amino acid sequence as set forth in SEQ ID NO:8 or a functional variant at least 80%, 85%, 90%, 92%, 94%, 96%, 98% identical to SEQ ID NO:8, the large protein (L) comprises an amino acid sequence as set forth in SEQ ID NO:9 or a functional variant at least 80%, 85%, 90%, 92%, 94%, 96%, 98% identical to SEQ ID NO:9, and the matrix protein (M) comprises an amino acid sequence as set forth in SEQ ID NO:10 or a functional variant at least 80%, 85%, 90%, 92%, 94%, 96%, 98% identical to SEQ ID NO:10.

In one embodiment relating to the second aspect, the recombinant vesicular stomatitis virus is replication-competent.

In one embodiment relating to the second aspect, the recombinant vesicular stomatitis virus lacks a functional gene coding for glycoprotein G, and/or lacks a functional glycoprotein G; or, the gene coding for the glycoprotein G is replaced by the gene coding for the glycoprotein GP of another virus, and/or the glycoprotein G is replaced by the glycoprotein GP of another virus; or, the gene coding for the glycoprotein G is replaced by the gene coding for the glycoprotein GP of lymphocyte choriomeningitis virus (LCMV), and/or the glycoprotein G is replaced by the glycoprotein GP of LCMV.

In one embodiment relating to the second aspect, the CCL21 protein or functional variant thereof is selected from the group comprising: (i) plasmin processed CCL21 protein, (ii) c-terminally truncated CCL21 protein, (iii) a protein comprising SEQ ID NO:2 or having at least 80% identity to SEQ ID NO:2, (iv) a protein comprising SEQ ID NO:3 or having at least 80% identity to SEQ ID NO:3, (v) a protein comprising SEQ ID NO:4 or having at least 80% identity to SEQ ID NO:4, (vi) a protein according to any of (i)-(v) further comprising a signal peptide sequence, (vii) a protein comprising SEQ ID NO:1 or having at least 80% identity to SEQ ID NO:1, or a protein comprising SEQ ID NO:5 or having at least 80%, 85%, 90%, 92%, 94%, 96%, 98% or 99% identity to SEQ ID NO:5.

In a preferred embodiment relating to the second aspect, the invention provides a recombinant vesicular stomatitis virus encoding in its genome a vesicular stomatitis virus nucleoprotein (N), large protein (L), phosphoprotein (P), matrix protein (M), glycoprotein (G) and at least one CCL21 protein or a functional variant thereof, preferably human CCL21, wherein the CCL21 protein or functional variant thereof is selected from the group comprising: (i) plasmin processed CCL21 protein, (ii) c-terminally truncated CCL21 protein, (iii) a protein comprising SEQ ID NO:2 or having at least 80% identity to SEQ ID NO:2, (iv) a protein comprising SEQ ID NO:3 or having at least 80% identity to SEQ ID NO:3, (v) a protein comprising SEQ ID NO:4 or having at least 80% identity to SEQ ID NO:4, (vi) a protein according to any of (i)-(v) further comprising a signal peptide sequence, (vii) a protein comprising SEQ ID NO:1 or having at least 80% identity to SEQ ID NO:1, or (viii) a protein comprising SEQ ID NO:5 or having at least 80%, 85%, 90%, 92%, 94%, 96%, 98% or 99% identity to SEQ ID NO:5, wherein, the gene coding for the glycoprotein G of the vesicular stomatitis virus is replaced by the gene coding for the glycoprotein GP of lymphocyte choriomeningitis virus (LCMV), and/or the glycoprotein G is replaced by the glycoprotein GP of LCMV, and wherein the nucleoprotein (N) comprises an amino acid as set forth in SEQ ID NO:7 or a functional variant at least 80%, 85%, 90%, 92%, 94%, 96%, 98% identical to SEQ ID NO:7, the phosphoprotein (P) comprises an amino acid as set forth in SEQ ID NO:8 or a functional variant at least 80%, 85%, 90%, 92%, 94%, 96%, 98% identical to SEQ ID NO:8, the large protein (L) comprises an amino acid as set forth in SEQ ID NO:9 or a functional variant at least 80%, 85%, 90%, 92%, 94%, 96%, 98% identical to SEQ ID NO:9, and the matrix protein (M) comprises an amino acid as set forth in SEQ ID NO:10 or a functional variant at least 80%, 85%, 90%, 92%, 94%, 96%, 98% identical to SEQ ID NO:10.

In a third aspect, the present invention provides for a pharmaceutical composition, characterized in that the composition comprises a recombinant rhabdovirus according to the first aspect or any of its embodiments, or a recombinant vesicular stomatitis virus according the second aspect or any of its embodiments.

In a fourth aspect, the present invention provides for a recombinant rhabdovirus according to the first aspect or any of its embodiments, or a recombinant vesicular stomatitis virus according the second aspect or any of its embodiments, or a pharmaceutical composition according to the third aspect or any of its embodiments, for use as a medicament.

In one embodiment relating to the fourth aspect, the invention provides a recombinant rhabdovirus, a recombinant vesicular stomatitis virus, or a pharmaceutical composition for the use in the treatment of cancer, preferably solid cancers. In a preferred embodiment, the solid cancer is selected from the list comprising: reproductive tumor, an ovarian tumor, a pancreatic tumor, a testicular tumor, an endocrine tumor, a gastrointestinal tumor, a liver tumor, a kidney tumor, a colon tumor, a colorectal tumor, a bladder tumor, a prostate tumor, a skin tumor, melanoma, a respiratory tumor, a lung tumor, a breast tumor, a head & neck tumor, a head and neck squamous-cell carcinoma (HNSCC), and a bone tumor.

In one embodiment relating to the fourth aspect, the recombinant rhabdovirus, the recombinant vesicular stomatitis virus, or the pharmaceutical composition is to be administered intratumorally or intravenously. In another related embodiment, the recombinant rhabdovirus, the recombinant vesicular stomatitis virus or the pharmaceutical composition is to be administered at least once intratumorally and subsequently intravenously. In a further related embodiment, the subsequent intravenous administration of the recombinant rhabdovirus, recombinant vesicular stomatitis virus or the pharmaceutical composition is given 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29, days, 30 days or 31 days after the initial intratumoral administration.

In a fifth aspect, the present invention provides for a composition comprising a recombinant rhabdovirus according to the first aspect or any of its embodiments, or a recombinant vesicular stomatitis virus according the second aspect or any of its embodiments and further an inhibitor, wherein the inhibitor is a PD-1 pathway inhibitor or a SMAC mimetic.

In one embodiment relating to the fifth aspect, the PD-1 pathway inhibitor is an antagonistic antibody, which is directed against PD-1 or PD-L1. In a further related embodiment, the SMAC mimetic is selected from the group consisting of any of compounds 1 to 26 from table 2 or a pharmaceutically acceptable salt of one of these compounds. In another related embodiment, the PD-1 pathway inhibitor is an antagonist selected from the group consisting of pembrolizumab, nivolumab, pidilizumab, atezolizumab, avelumab, durvalumab, PDR-001, PD1-1, PD1-2, PD1-3, PD1-4 and PD1-5 (as shown in Table 1).

In a sixth aspect, the present invention provides a kit of parts comprising: a recombinant rhabdovirus, a recombinant vesicular stomatitis virus or a pharmaceutical composition as defined in any of the first to third aspects or any of their embodiments, and a PD-1 pathway inhibitor or SMAC mimetic as defined in any of the embodiments relating to the fifth aspect.

In a seventh aspect, the present invention provides for a combination treatment comprising: a) a recombinant rhabdovirus according to the first aspect or any of its embodiments, or a recombinant vesicular stomatitis virus according the second aspect or any of its embodiments, or a pharmaceutical composition according to the third aspect or any of its embodiments, and b) a PD-1 pathway inhibitor or a SMAC mimetic. In one embodiment relating to the seventh aspect a) and b) may be administered concomitantly, sequentially or alternately. In a related embodiment, a) and b) are administered via different administration routes. In a further related embodiment, a) is administered intratumorally b) is administered intravenously.

In one embodiment relating to the seventh aspect, the PD-1 pathway inhibitor is an antagonistic antibody, which is directed against PD-1 or PD-L1. In a related embodiment the PD-1 pathway inhibitor is selected from the group consisting of pembrolizumab, nivolumab, pidilizumab, atezolizumab, avelumab, durvalumab, PDR-001, PD1-1, PD1-2, PD1-3, PD1-4 and PD1-5 (see Table 1). In a further related embodiment the SMAC mimetic is selected from the group consisting of any one of compounds 1 to 26 according to table 2 or a pharmaceutically acceptable salt of one of these compounds.

In an eight aspect, the invention provides for a virus producing cell, characterized in that the cell produces a recombinant rhabdovirus according to the first aspect or any of its embodiments, or a recombinant vesicular stomatitis virus according the second aspect or any of its embodiments.

In one embodiment relating to the eight aspect, the virus producing cell is a Vero cell, a HEK cell, a HEK293 cell, a Chinese hamster ovary cell (CHO), or a baby hamster kidney (BHK) cell.

In a ninth aspect, the invention provides for a method of producing a recombinant rhabdovirus in a cell culture:
(i) Infecting a host cell with a recombinant rhabdovirus, preferably a vesicular stomatitis virus,
(ii) Culturing the host cell under conditions allowing replication of the recombinant rhabdovirus,
(iii) Harvesting the recombinant rhabdovirus from the cell culture,
(iv) Optionally, enzyme treatment of the virus harvest, preferably with benzonase,
(v) Capturing the rhabdovirus harvest by loading on a cation exchange monolith membrane adsorber or resin followed by elution,
(vi) Polish rhabdovirus by subjecting the eluate of step (v) to size exclusion, multi modal size exclusion/ion exchange or tangential flow filtration,
(vii) Buffer change of polished rhabdovirus by ultrafiltration/diafiltration,
(viii) Sterile filtration of rhabdovirus.

In one embodiment relating to the ninth aspect, the host cell is a HEK293 cell.

In one embodiment relating to the ninth aspect, the host cell is cultured in suspension.

In one embodiment relating to the ninth aspect, the recombinant rhabdovirus is formulated into a pharmaceutical composition. In a preferred embodiment, the recombinant rhabdovirus according to the first aspect or any of its embodiments, or a recombinant vesicular stomatitis virus according the second aspect or any of its embodiments is formulated into a pharmaceutical composition.

In a further aspect, the recombinant rhabdovirus encodes in its RNA genome at least one CCL21 protein or a functional variant thereof, preferably human CCL21, wherein the RNA genome of the recombinant rhabdovirus comprises or consists of a coding sequence identical or at least 75%, 76%, 77%, 78%, 79%, 80%, 81%, 82%, 83%, 84%, 88%, 88%, 87%, 88%, 89%, 90%, 91%, 92%, 93%, 94%, 98%, 96%, 97%, 98%, or 99% identical to SEQ ID NO: 24.

BRIEF DESCRIPTION OF THE DRAWINGS

FIG. 2A-D: Single tumor growth curves of CT26.CL25-IFNARKO tumor-bearing mice. (A) control mice (mock treated), (B) mice treated with anti-PD-1, (C) mice treated with VSV-GP i.v. or (D) mice treated with a combination of VSV-GP and anti-PD-1.

FIG. 3A-C: Tumor (re-)challenge analysis of cured mice which were pre-treated with VSV-GP (see FIG. 2C) or the combination of VSV-GP and anti-PD1 (see FIG. 2D). (A) Naïve mice with CT26.CL25-IFNARKO tumor cells were used as control. For tumor (re-)challenge CT26C125 IFNAR-/- cells were injected into either (B) VSV-GP treated long-term tumor free mice (cured) from the experiments as shown in FIG. 2C, or (C) VSV-GP and anti-PD-1 combination treated long-term tumor free mice (cured) from the experiments as shown in FIG. 2D.

FIG. 5A-B: (A) Cartoon illustrating the CCL21 (Transgene) insertion site within the VSV-GP genome. (B) Cartoon illustrating viral rescue.

FIG. 6: (A) Analysis of murine CCL21 in the supernatants of HEK293 cells infected with VSV-GP-muCCL21 (VSV-GP encoding full length murine CCL21). (B) Functional analysis of murine T-cell migration using a Transwell Set-up and recombinant murine CCL21 or supernatants from VSV-GP resp. VSV-GP-muCCL21 infected HEK293 cells.

FIG. 7A-C: Single tumor growth analysis of CT26.CL25-IFNARKO tumor-bearing mice. Tumor bearing mice were treated with (A) VSV-GP, (B) SMACm (SMAC mimetic), or (C) VSV-GP in combination with a SMACm (SMAC mimetic). Dark black lines show tumor volume of untreated control mice whereas light grey lines show tumor volume of mice treated with either (A) VSV-GP, (B) SMACm, or (C) VSV-GP+ SMACm.

FIG. 8A-C: Single tumor growth analysis of CT26.CL25-IFNARKO tumor-bearing mice. Tumor bearing mice were treated with (A) VSV-GP-CCL21, (B) SMACm (SMAC mimetic), or (C) VSV-GP-CCL21 in combination with a SMACm (SMAC mimetic). Dark black lines show tumor volume of untreated control mice whereas light grey lines show tumor volume of mice treated with either (A) VSV-GP-CCL21, (B) SMACm, or (C) VSV-GP-CCL21+ SMACm.

FIG. 17: Functional analysis of human monocyte derived dendritic cell (moDC) migration using a Transwell Set-up and recombinant human CCL21 or supernatants from VSV-GP resp. VSV-GP-huCCL21 or VSV-GP-huCCL21(1-79) infected HEK293 cells.

FIG. 19A-C: Viral Titers of VSV-GP (GP), VSV-GP-huCCL21 (21) or VSV-GP-huCCL21(1-79) (21 k) in supernatants of the indicated cells were measured at the indicated time points post viral infection to determine viral replication competence. The different panels show from left to right (A) Vero cells, (B) BHK21 cells, and (C) HEK293 cells. In each panel VSV-GP (GP), VSV-GP-huCCL21 (21) or VSV-GP-huCCL21(1-79) (21 k) titers were measured at 0 h, 24 h and 48 h.

Figure 21:
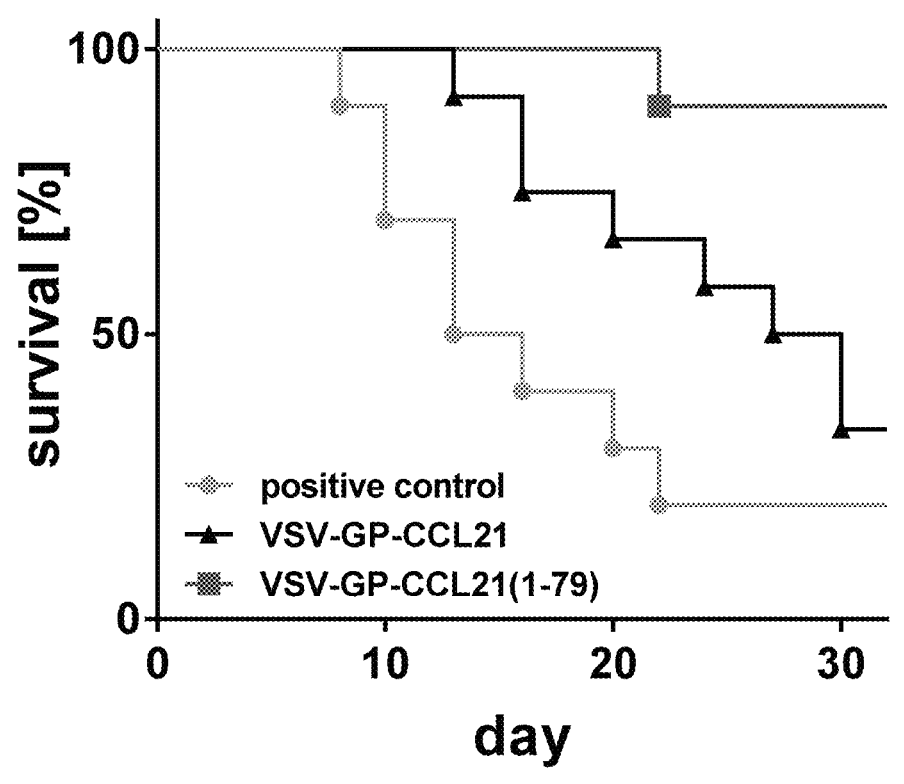

FIG. 21: 30-day survival of mice from FIG. 20.

DETAILED DESCRIPTION OF THE INVENTION

Figure 1:
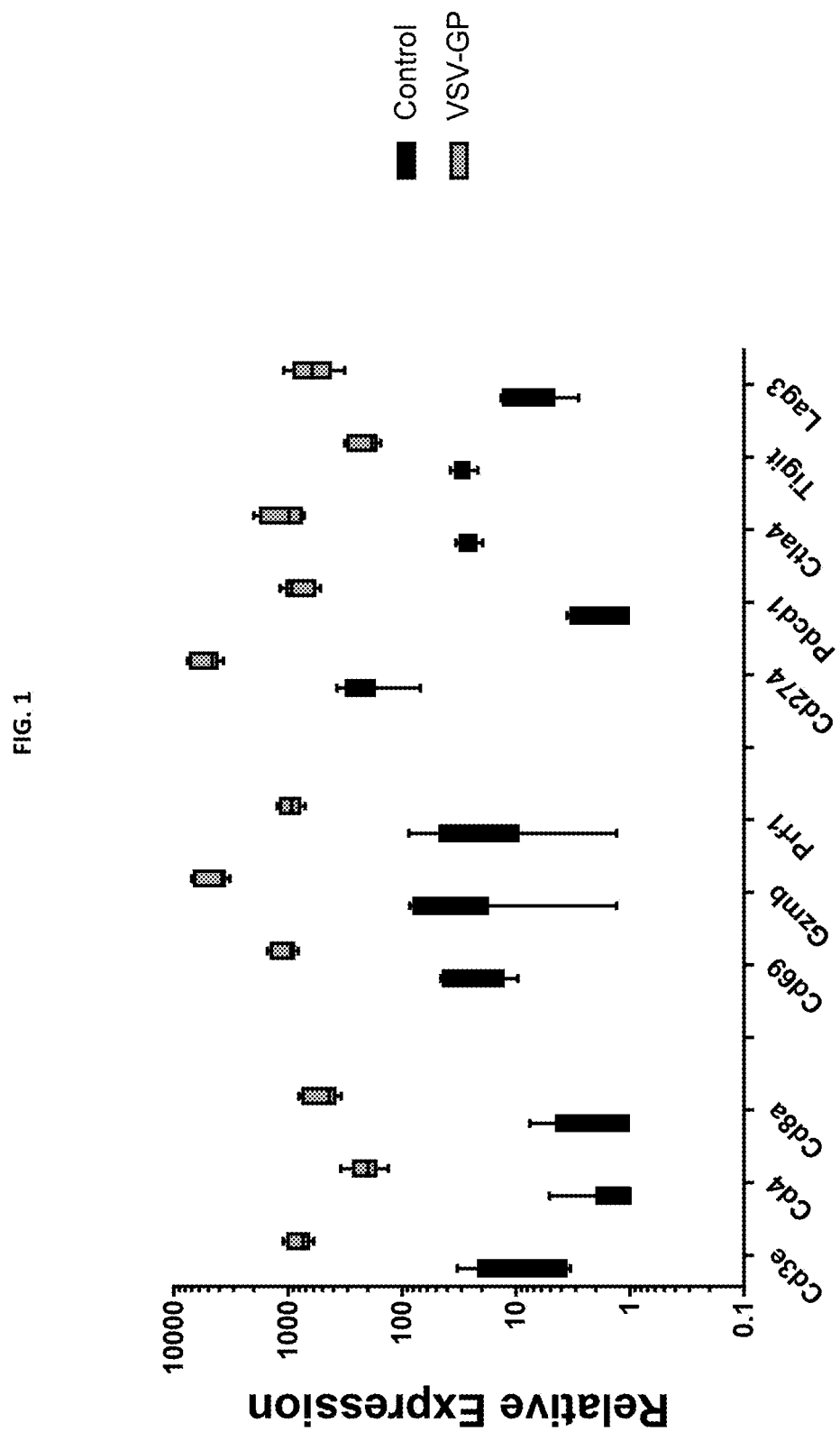
FIG. 1: Expression Analysis of LLC1-IFNARKO Tumors (whole RNA) from control or VSV-GP treated mice for the indicated genes.
Figure 4:
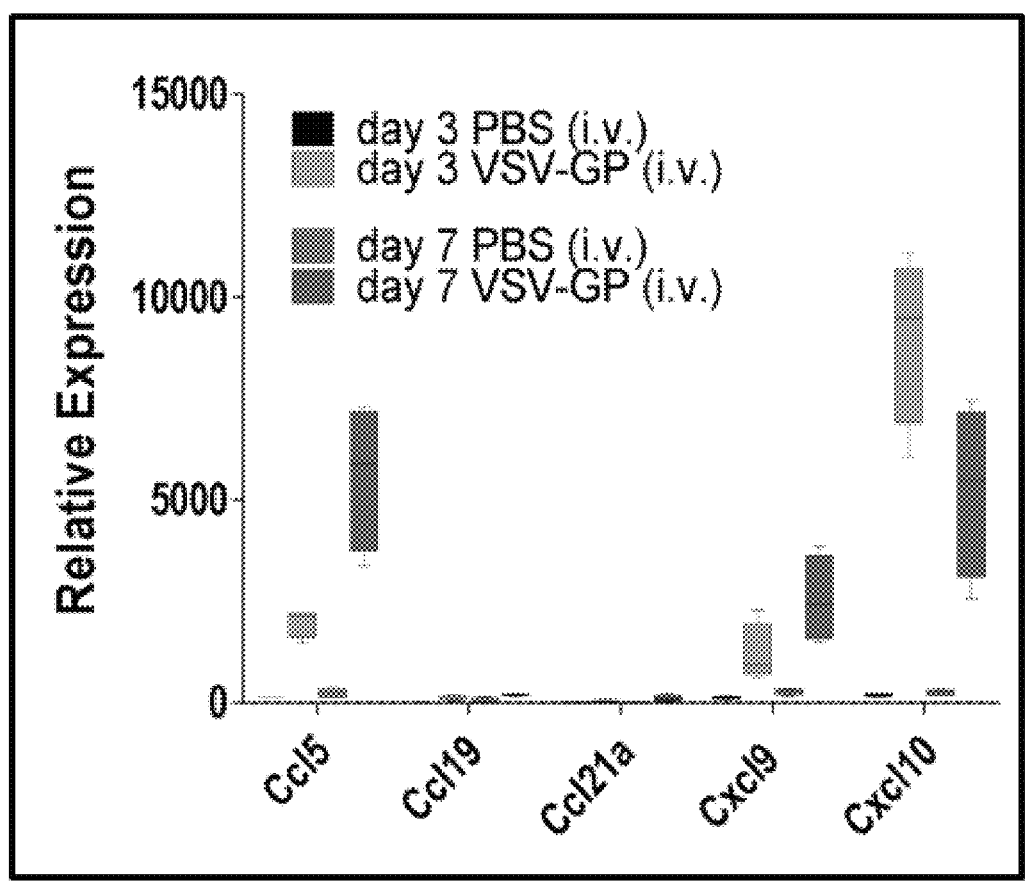
FIG. 4: Expression Analysis of LLC1-IFNARKO Tumors (whole RNA) from control or VSV-GP treated mice for the indicated chemokines.

In the following detailed description, numerous specific details are set forth to provide a full understanding of the present invention. It will be apparent, however, to one ordinarily skilled in the art that the subject technology may be practiced without some of these specific details. In other instances, well-known structures and techniques have not been shown in detail so as not to obscure the present invention. The headings are included merely for convenience to assist in reading and shall not be understood to limit the invention to specific aspects or embodiments.

Rhabdoviruses

The family of rhabdoviruses includes 18 genera and 134 species with negative-sense, single-stranded RNA genomes of approximately 10-16 kb (Walke et al., ICTV Virus Taxonomy Profile: Rhabdoviridae, Journal of General Virology, 99:447-448 (2018)).

Characterizing features of members of the family of rhabdoviruses include one or more of the following: A bullet-shaped or bacilliform particle 100-430 nm in length and 45-100 nm in diameter comprised of a helical nucleocapsid surrounded by a matrix layer and a lipid envelope, wherein some rhabdoviruses have non-enveloped filamentous viruses. A negative-sense, single-stranded RNA of 10.8-16.1 kb, which are mostly unsegmented. A genome encoding for at least 5 genes encoding the structural proteins nucleoprotein (N), large protein (L), phosphoprotein (P), matrix protein (M), and glycoprotein (G).

As used herein a rhabdovirus can belong to the genus of: almendravirus, curiovirus, cytorhabdovirus, dichorhavirus, ephemerovirus, Hapavirus, ledantevirus, lyssavirus, novirhabdovirus, nucleorhabdovirus, perhabdovirus, sigmavirus, sprivivirus, sripuvirus, tibrovirus, tupavirus, varicosavirus or vesiculovirus.

Within the genus mentioned herein the rhabdovirus can belong to any of the listed species. The genus of almendravirus includes: arboretum almendravirus, balsa almendravirus, Coot Bay almendravirus, Puerto Almendras almendravirus, Rio Chico almendravirus; the genus of curiovirus includes: curionopolis curiovirus, Iriri curiovirus, ltacaiunas curiovirus, Rochambeau curiovirus; the genus of cythorhabdovirus includes: Alfalfa dwarf cytorhabdovirus, Barley yellow striate mosaic cytorhabdovirus, Broccoli necrotic yellows cytorhabdovirus, Colocasia bobone disease-associated cytorhabdovirus, Festuca leaf streak cytorhabdovirus, Lettuce necrotic yellows cytorhabdovirus, Lettuce yellow mottle cytorhabdovirus, Northern cereal mosaic cytorhabdovirus, Sonchus cytorhabdovirus 1, Strawberry crinkle cytorhabdovirus, Wheat American striate mosaic cytorhabdovirus; the genus of dichorhavirus includes: Coffee ringspot dichorhavirus, Orchid fleck dichorhavirus; the genus of ephemerovirus includes: Adelaide River ephemerovirus, Berrimah ephemerovirus, Bovine fever ephemerovirus, Kimberley ephemerovirus, Koolpinyah ephemerovirus, Kotonkan ephemerovirus, Obodhiang ephemerovirus, Yata ephemerovirus; the genus of hapavirus includes: Flanders hapavirus, Gray Lodge hapavirus, Hart Park hapavirus, Joinjakaka hapavirus, Kamese hapavirus, La Joya hapavirus, Landjia hapavirus, Manitoba hapavirus, Marco hapavirus, Mosqueiro hapavirus, Mossuril hapavirus, Ngaingan hapavirus, Ord River hapavirus, Parry Creek hapavirus, Wongabel hapavirus; the genus of ledantevirus includes: Barur ledantevirus, Fikirini ledantevirus, Fukuoka ledantevirus, Kanyawara ledantevirus, Kern Canyon ledantevirus, Keuraliba ledantevirus, Kolente ledantevirus, Kumasi ledantevirus, Le Dantec ledantevirus, Mount Elgon bat ledantevirus, Nishimuro ledantevirus, Nkolbisson ledantevirus, Oita ledantevirus, Wuhan ledantevirus, Yongjia ledantevirus; the genus of lyssavirus includes: Aravan lyssavirus, Australian bat lyssavirus, Bokeloh bat lyssavirus, Duvenhage lyssavirus, European bat 1 lyssavirus, European bat 2 lyssavirus, Gannoruwa bat lyssavirus, Ikoma lyssavirus, Irkut lyssavirus, Khujand lyssavirus, Lagos bat lyssavirus, Lleida bat lyssavirus, Mokola lyssavirus, Rabies lyssavirus, Shimoni bat lyssavirus, West Caucasian bat lyssavirus; the genus of novirhabdovirus includes: Hirame novirhabdovirus, Piscine novirhabdovirus, Salmonid novirhabdovirus, Snakehead novirhabdovirus; the genus of nucleorhabdovirus includes: Datura yellow vein nucleorhabdovirus, Eggplant mottled dwarf nucleorhabdovirus, Maize fine streak nucleorhabdovirus, Maize Iranian mosaic nucleorhabdovirus, Maize mosaic nucleorhabdovirus, Potato yellow dwarf nucleorhabdovirus, Rice yellow stunt nucleorhabdovirus, Sonchus yellow net nucleorhabdovirus, Sowthistle yellow vein nucleorhabdovirus, Taro vein chlorosis nucleorhabdovirus; the genus of perhabdovirus includes: Anguillid perhabdovirus, Perch perhabdovirus, Sea trout perhabdovirus; the genus of sigmavirus includes: Drosophila affinis sigmavirus, Drosophila ananassae sigmavirus, Drosophila immigrans sigmavirus, Drosophila melanogaster sigmavirus, Drosophila obscura sigmavirus, Drosophila tristis sigmavirus, Muscina stabulans sigmavirus; the genus of sprivivirus includes: Carp sprivivirus, Pike fry sprivivirus; the genus of Sripuvirus includes: Almpiwar sripuvirus, Chaco sripuvirus, Niakha sripuvirus, Sena Madureira sripuvirus, Sripur sripuvirus; the genus of tibrovirus includes: Bas-Congo tibrovirus, Beatrice Hill tibrovirus, Coastal Plains tibrovirus, Ekpoma 1 tibrovirus, Ekpoma 2 tibrovirus, Sweetwater Branch tibrovirus, tibrogargan tibrovirus; the genus of tupavirus includes: Durham tupavirus, Klamath tupavirus, Tupaia tupavirus; the genus of varicosavirus includes: Lettuce big-vein associated varicosavirus; the genus of vesiculovirus includes: Alagoas vesiculovirus, American bat vesiculovirus, Carajas vesiculovirus, Chandipura vesiculovirus, Cocal vesiculovirus, Indiana vesiculovirus, Isfahan vesiculovirus, Jurona vesiculovirus, Malpais Spring vesiculovirus, Maraba vesiculovirus, Morreton vesiculovirus, New Jersey vesiculovirus, Perinet vesiculovirus, Piry vesiculovirus, Radi vesiculovirus, Yug Bogdanovac vesiculovirus, or Moussa virus.

Preferably, the recombinant rhabdovirus of the invention is an oncolytic rhabdovirus. In this respect, oncolytic has its regular meaning known in the art and refers to the ability of a rhabdovirus to infect and lyse (break down) cancer cells but not normal cells (to any significant extend). Preferably, the oncolytic rhabdovirus is capable of replication within cancer cells. Oncolytic activity may be tested in different assay systems known to the skilled artisan (an exemplary in vitro assay is described by Muik et al., Cancer Res., 74(13), 3567-78, 2014). It is to be understood that an oncolytic rhabdovirus may infect and lyse only specific types of cancer cells. Also, the oncolytic effect may vary depending on the type of cancer cells.

In a preferred embodiment, the rhabdovirus belongs to the genus of vesiculovirus. Vesiculovirus species have been defined primarily by serological means coupled with phylogenetic analysis of the genomes. Biological characteristics such as host range and mechanisms of transmission are also used to distinguish viral species within the genus. As such, the genus of vesiculovirus form a distinct monophyletic group well-supported by Maximum Likelihood trees inferred from complete L sequences.

Viruses assigned to different species within the genus vesiculovirus may have one or more of the following characteristics: A) a minimum amino acid sequence divergence of 20% in L; B) a minimum amino acid sequence divergence of 10% in N; C) a minimum amino acid sequence divergence of 15% in G; D) can be distinguished in serological tests; and E) occupy different ecological niches as evidenced by differences in hosts and or arthropod vectors.

Preferred is the vesicular stomatitis virus (VSV) and in particular the VSV-GP (recombinant with GP of LCMV). Advantageous properties of the VSV-GP include one or more of the following: very potent and fast killer (<8 h);

oncolytic virus; systemic application possible; reduced neurotropism/neurotox; it reproduces lytically and induces immunogenic cell death; does not replicate in healthy human cells, due to interferon (IFN) response; strong activation of innate immunity; about 3 kb space for immunomodulatory cargos and antigens; recombinant with an arenavirus glycoprotein from the Lympho-Chorio-Meningitis-Virus (LCMV); favorable safety features in terms of reduced neurotoxicity and less sensitive to neutralizing antibody responses and complement destruction as compared to the wild type VSV (VSV-G); specifically replicates in tumor cells, which have lost the ability to mount and respond to anti-viral innate immune responses (e.g. type-I IFN signaling); abortive replication in "healthy cells" so is rapidly excluded from normal tissues; viral replication in tumor cells leads to the induction of immunogenic cell death, release of tumor associated antigens, local inflammation and the induction of anti-tumor immunity.

The invention is further embodied by a recombinant vesicular stomatitis virus, encoding in its genome at least for a vesicular stomatitis virus nucleoprotein (N), large protein (L), phosphoprotein (P), matrix protein (M), glycoprotein (G) and at least one CCL21 protein or a functional variant thereof, preferably human CCL21.

In a preferred embodiment the recombinant vesicular stomatitis virus encodes in its genome at least for a vesicular stomatitis virus nucleoprotein (N) comprising an amino acid sequence as set forth in SEQ ID NO:7 or a functional variant at least 80%, 85%, 90%, 92%, 94%, 96%, 98% identical to SEQ ID NO:7, a phosphoprotein (P) comprising an amino acid sequence as set forth in SEQ ID NO:8 or a functional variant at least 80%, 85%, 90%, 92%, 94%, 96%, 98% identical to SEQ ID NO:8, a large protein (L) comprising an amino acid sequence as set forth in SEQ ID NO:9 or a functional variant at least 80%, 85%, 90%, 92%, 94%, 96%, 98% identical to SEQ ID NO:9, and a matrix protein (M) comprising an amino acid sequence as set forth in SEQ ID NO:10 or a functional variant at least 80%, 85%, 90%, 92%, 94%, 96%, 98% identical to SEQ ID NO:10.

It is understood by the skilled artisan that modifications to the vesicular stomatitis virus nucleoprotein (N), large protein (L), phosphoprotein (P), matrix protein (M), or glycoprotein (G) sequence can be made without losing the basic functions of those proteins. Such functional variants as used herein retain all or part of their basic function or activity. The protein L for example is the polymerase and has an essential function during transcription and replication of the virus. A functional variant thereof must retain at least part of this ability. A good indication for retention of basic functionality or activity is the successful production of viruses, including these functional variants, that are still capable to replicate and infect tumor cells. Production of viruses and testing for infection and replication in tumor cells may be tested in different assay systems known to the skilled artisan (an exemplary in vitro assay is described by Muik et al., Cancer Res., 74(13), 3567-78, 2014).

In a preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CCL21 protein or a functional variant thereof, preferably human CCL21, wherein the large protein (L) comprises an amino acid sequence having a sequence identity 80% of SEQ ID NO:9.

In a preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CCL21 protein or a functional variant thereof, preferably human CCL21, wherein the nucleoprotein (N) comprises an amino acid sequence having a sequence identity 90% of SEQ ID NO:7.

In a further preferred embodiment the recombinant vesicular stomatitis virus encodes in its genome at least for a vesicular stomatitis virus nucleoprotein (N), large protein (L), phosphoprotein (P), matrix protein (M), glycoprotein (G) and at least one CCL21 protein or a functional variant thereof, preferably human CCL21, wherein the large protein (L) comprises an amino acid sequence having a sequence identity equal or greater 80% of SEQ ID NO:9 and the nucleoprotein (N) comprises an amino acid sequence having a sequence identity 90% of SEQ ID NO:7.

In a preferred embodiment of the invention the RNA genome of the recombinant rhabdovirus of the invention comprises or consists of a sequence as shown in SEQ ID NO: 24. Furthermore, the RNA genome of the recombinant rhabdovirus of the invention may also consist of or comprise those sequences, wherein nucleic acids of the RNA genome are exchanged according to the degeneration of the genetic code, without leading to an alteration of respective amino acid sequence. In a further preferred embodiment, the RNA genome of the recombinant rhabdovirus of the invention comprises or consists of a coding sequence identical or at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 24.

It is to be understood that a recombinant rhabdovirus of the invention may encode in its genome further cargos, such as tumor antigens, further chemokines, cytokines or other immunomodulatory elements.

In a further embodiment the recombinant rhabdovirus of the invention additionally encodes in its genome a sodium iodide symporter protein (NIS). Expression of NIS and co-incubation with e.g. $^{125}$I allows the use of NIS as imaging reporter (Carlson et al., Current Gene Therapy, 12, 33-47, 2012).

Recombinant Rhabdovirus

It is known that certain wildtype rhabdovirus strains such as wildtype VSV strains are considered to be neurotoxic. It is also reported that infected individuals are able to rapidly mount a strong humoral response with high antibody titers directed mainly against the glycoprotein. Neutralizing antibodies targeting the glycoprotein G of rhabdoviruses in general and VSV specifically are able to limit virus spread and thereby mediate protection of individuals from virus re-infection. Virus neutralization, however, limits repeated application of the rhabdovirus to the cancer patient.

To eliminate these drawbacks the rhabdovirus wildtype glycoprotein G may be replaced with the glycoprotein from another virus. In this respect replacing the glycoprotein refers to (i) replacement of the gene coding for the wild type glycoprotein G with the gene coding for the glycoprotein GP of another virus, and/or (ii) replacement of the wild type glycoprotein G with the glycoprotein GP of another virus.

In a preferred embodiment the rhabdovirus glycoprotein G is replaced with the glycoprotein GP of the lymphocytic choriomeningitis virus (LCMV), preferably with the strain WE-HPI. In an even more preferred embodiment, the rhabdovirus is a vesicular stomatitis virus with the glycoprotein GP of the lymphocytic choriomeningitis virus (LCMV), preferably with the strain WE-HPI. Such VSV is for example described in WO2010/040526 and named VSV-GP. Advantages offered are (i) the loss of VSV-G mediated neurotoxicity and (ii) a lack of vector neutralization by antibodies (as shown in mice).

The glycoprotein GP of the lymphocytic choriomeningitis virus (LCMV) may be GP1 or GP2. The invention includes glycoproteins from different LCMV strains. In particular, LCMV-GP can be derived from LCMV wild-type or LCMV strains LCMV-WE, LCMV-WE-HPI, LCMV-WE-HPIopt. In a preferred embodiment, the gene coding for the glycoprotein GP of the LCMV encodes for a protein with an amino acid sequence as shown in SEQ ID NO:11 or an amino acid sequence having at least 80, 85, 90, 95%, 98%, 99% sequence identity to the amino acid sequence of SEQ ID NO:11 while the functional properties of the recombinant rhabdovirus comprising a glycoprotein GP encoding an amino acid sequence as shown in SEQ ID NO:11 are maintained.

In another embodiment the recombinant rhabdovirus glycoprotein G is replaced with the glycoprotein GP of the Dandenong virus (DANDV) or Mopeia (MOPV) virus. In a more preferred embodiment, the recombinant rhabdovirus is a vesicular stomatitis virus wherein the glycoprotein G is replaced with the glycoprotein GP of the Dandenong virus (DANDV) or Mopeia (MOPV) virus. Advantages offered are (i) the loss of VSV-G mediated neurotoxicity and (ii) a lack of vector neutralization by antibodies (as shown in mice).

The Dandenong virus (DANDV) is an old world arenavirus. To date, there is only a single strain known to the person skilled in the art, which comprise a glycoprotein GP and which may be employed within the present invention as donor of the glycoprotein GP comprised in the recombinant rhabdovirus of the invention. The DANDV glycoprotein GP comprised in the recombinant rhabdovirus of the invention has more than 6 glycosylation sites, in particular 7 glycosylation sites. An exemplary preferred glycoprotein GP is that as comprised in DANDV as accessible under Genbank number EU136038. In one embodiment, the gene coding for the glycoprotein GP of the DNADV encodes for an amino acid sequence as shown in SEQ ID NO:12 or a sequence having at least 80, 85, 90 or 95% sequence identity to the amino acid sequence of SEQ ID NO:12 while the functional properties of the recombinant rhabdovirus comprising a glycoprotein GP encoding an amino acid sequence as shown in SEQ ID NO:12 are maintained.

The Mopeia virus (MOPV) is an old world arenavirus. There are several strains known to the person skilled in the art, which comprise a glycoprotein GP and which may be employed within the present invention as donor of the glycoprotein GP comprised in the recombinant rhabdovirus of the invention. The MOPV glycoprotein GP comprised in the recombinant rhabdovirus of the invention has more than 6 glycosylation sites, in particular 7 glycosylation sites. An exemplary preferred glycoprotein GP is that as comprised in Mopeia virus as accessible under Genbank number AY772170. In one embodiment, the gene coding for glycoprotein GP of the MOPV encodes for an amino acid sequence as shown in SEQ ID NO:13 or a sequence having at least 60, 65, 70, 75, 80, 85, 90 or 95% sequence identity to the amino acid sequence of SEQ ID NO:13 while the functional properties of the recombinant rhabdovirus comprising a glycoprotein GP encoding an amino acid sequence as shown in SEQ ID NO:13 are maintained.

CCL21 and Functional Variants of CCL21

It was surprisingly found that a recombinant rhabdovirus encoding in its genome a CCL21 protein was able to induce tumor cell lysis combined with immunogenic cell death and stimulation of innate immune cells in the tumor microenvironment. Further, prolonged survival rates were observed in an established mouse tumor model treated with such recombinant rhabdovirus armed with CCL21.

CCL21 belongs to the CC chemokine family and is also known as secondary lymphoid-tissue chemokine (SLC), exodus-2, ckb9, scya21, TCA4 or 6Ckine. CCL21 contains a C-terminal region that binds to extracellular matrix. CCL21 also binds to the CCR7 cell surface receptor and thereby exerts its function such as attraction of T cells and dendritic cells as well as activation of the latter. CCR7 is expressed on a wide-range of peripheral T cells and dendritic cells in both healthy and cancer patients.

Thus in one aspect, the recombinant rhabdovirus encoding in its genome at least one CCL21 protein or a functional variant thereof is able to enhance recruitment of T-cells and dendritic cells to the tumor environment.

In another aspect, the local expression of the highly potent chemokine CCL21 further enhances immune cell recruitment of preferentially T-lymphocytes and dendritic cells into the tumor microenvironment and improved efficacy of the recombinant rhabdovirus.

In yet another aspect, the recombinant rhabdovirus encoding in its genome at least one CCL21 protein or a functional variant thereof acts as an innate immune stimulator.

In one aspect, the recombinant rhabdovirus encoding in its genome at least one CCL21 protein or a functional variant thereof turns cold tumors into hot tumors. In particular, the resulting pro-inflammatory tumor microenvironment turns non-T cell infiltrated ("cold") tumors into T cell inflamed ("hot") tumors and is accompanied by generation of an adaptive anti-tumor immune response in the tumor-draining lymph nodes.

Human CCL21 protein was described e.g. by M. Nagira et al, The Journal of Biological Chemistry, 272, 19518-19524 (Aug. 1, 1997) and is a highly basic polypeptide of 134 amino acids total with a putative signal peptide of 23 amino acids:

```
                                         (SEQ ID NO: 1)
MAQSLALSLLILVLAFGIPRTQGSDGGAQDCCLKYSQRKIPAKVVRSYRKQ

EPSLGCSIPAILFLPRKRSQAELCADPKELWVQQLMQHLDKTPSPQKPAQG

CRKDRGASKTGKKGKGSKGCKRTERSQTPKGP
```

A CCL21 protein in particular includes CCL21 comprising or consisting of the following sequence:

```
                                         (SEQ ID NO: 2)
SDGGAQDCCLKYSQRKIPAKVVRSYRKQEPSLGCSIPAILFLPRKRSQAEL

CADPKELWVQQLMQHLDKTPSPQKPAQGCRKDRGASKTGKKGKGSKGCKRT

ERSQTPKGP
```

Preferably, a CCL21 protein comprises or consists of a protein having the following sequence:

```
                                         (SEQ ID NO: 4)
SDGGAQDCCLKYSQRKIPAKVVRSYRKQEPSLGCSIPAILFLPRKRSQAEL

CADPKELWVQQLMQHLDKTPSPQKPAQGCR
``` or having at least 70%, 72%, 74%, 76%, 78%, 80%, 85%, 89%, 90%, 91%, 92%, 93%, 94%, 95%, 96%, 97%, 98%, 99% or 100% identity to SEQ ID NO:4.

More preferably, a CCL21 protein comprises or consists of a protein having the following sequence:

```
                                            (SEQ ID NO: 3)
SDGGAQDCCLKYSQRKIPAKVVRSYRKQEPSLGCSIPAILFLPRKRSQAEL

CADPKELWVQQLMQHLDKTPSPQKPAQG
``` or having at least 70%, 72%, 74%, 76%, 78%, 80%, 85%, 89%, 90%, 91%, 92%, 93%, 94%, 95%, 96%, 97%, 98%, 99% or 100% identity to SEQ ID NO:3.

The term "signal peptide" or "signal peptide sequence" describes a peptide sequence usually 10 to 30 amino acids in length and present at the N-terminal end of newly synthesized secretory or membrane polypeptides which directs the polypeptide across or into a cell membrane of the cell (the plasma membrane in prokaryotes and the endoplasmic reticulum membrane in eukaryotes). It is usually subsequently removed. In particular, the signal peptide may be capable of directing the polypeptide into a cell's secretory pathway.

It is to be understood that for the present invention other (i.e., other than the wild-type) signal peptide sequences may be used together with the CCL21 protein. Such other signal peptide sequences may replace the original wild-type signal peptide sequence. A signal peptide includes peptides that direct newly synthesized protein in the ribosome to the ER and further to the Golgi complex for transport to the plasma membrane or out of the cell. They generally include a string of hydrophobic amino acids and include immunoglobulin leader sequences as well as others known to those skilled in the art. Signal peptides include in particular peptides capable of being acted upon by signal peptidase, a specific protease located on the cisternal face of the endoplasmatic reticulum. Signal peptides are well understood by those of skill in the art and may include any known signal peptide. The signal peptide is incorporated at the N-terminus of the protein and processing of the CCL21 protein by signal peptidase produces the active biological form.

In a preferred embodiment the signal peptide has a sequence as shown in SEQ ID NO:6. In a related preferred embodiment the CCL21 protein comprises or consists of a protein having the following sequence:

```
                                            (SEQ ID NO: 5)
MGWSCIILFLVATATGVHSSDGGAQDCCLKYSQRKIPAKVVRSYRKQEPSL

GCSIPAILFLPRKRSQAELCADPKELWVQQLMQHLDKTPSPQKPAQG
``` or having at least 70%, 72%, 74%, 76%, 78%, 80%, 85%, 90%, 95%, 98%, 99% or 100% identity to SEQ ID NO:5.

In a related embodiment, a CCL21 protein includes a protein comprising or consisting of the amino acids of SEQ ID Nos: 2, 3 or 4 or respectively having at least 70%, 72%, 74%, 76%, 78%, 80%, 85%, 89%, 90%, 91%, 92%, 93%, 94%, 95%, 96%, 97%, 98%, 99% or 100% identity to SEQ ID Nos:2, 3 or 4 and further comprising a signal peptide sequence. In a preferred embodiment the signal peptide sequence comprises or consists of the amino acids 1-19 of SEQ ID NO:5.

A CCL21 protein also includes a protein comprising or consisting of the amino acids of SEQ ID Nos: 2, 3 or 4 or respectively having at least 70%, 72%, 74%, 76%, 7%, 80%, 85%, 89%, 90%, 91%, 92%, 93%, 94%, 95%, 96%, 97, 98%, 99% or 100% identity to SEQ ID Nos: 2, 3 or 4 and further comprising a signal peptide sequence comprising or consisting of the amino acids 1-23 of SEQ ID NO:1.

A CCL21 protein further includes a protein corresponding to the plasmin processed forms of CCL21. CCL21 contains an extended unique C-terminus (e.g. human CCL21 about 30aa) with a net positive charge that contributes to binding of extracellular matrix components such as heparin-like glycosaminoglycans. Truncation/deletion of the C-terminus dramatically reduces binding to glycosaminoglycans like heparin. CCL21 is processed within the human body by plasmin which is defective in some human cancers. It was shown that the necessity of plasmin cleavage can be overcome by encoding the bioactive, i.e. biologically active, N-terminal fragment of CCL21, which resembles plasmin processed forms of CCL21 into a recombinant rhabdovirus. Plasmin processed forms of CCL21 are characterized by a truncation/deletion of the C-terminus resulting in a reduced ability to bind to heparin and/or heparan sulfate which can be measured by methods known to the skilled artisan. In this context a reduced ability to bind to heparin and/or heparan sulfate refers to a comparison with a CCL21 protein having the SEQ ID NO:1 or 2 and a binding ability that is reduced to 95%, 90%, 85%, 80%, 75%, 70%, 65%, 60%, 55%, 50%, 45%, 40%, 35%, 30%, 25%, 20% or lower of the binding ability of the CCL21 protein with the sequence as shown in SEQ ID NO:1 or 2 (respectively with or without signal peptide sequence) if tested in the same assay and under the same conditions.

Plasmin is a serine protease that acts to dissolve fibrin blood clots. Apart from fibrinolysis, plasmin proteolyses proteins in various other systems: It activates collagenases, some mediators of the complement system, and weakens the wall of the Graafian follicle, leading to ovulation. It cleaves fibrin, fibronectin, thrombospondin, laminin, and von Willebrand factor. Plasmin belongs to the family of serine proteases. Plasmin is released as a proenzyme called plasminogen from the liver into the systemic circulation. The conversion of plasminogen to active plasmin involves the cleavage of the peptide bond between Arg-561 and Val-562 by e.g. tissue plasminogen activator (tPA), urokinase plasminogen activator (uPA), kallikrein, and factor XII (Hageman factor).

Cleavage of CCL21 protein by plasmin can either occur on cell surface-bound CCL21 or in vitro in either case by incubating CCL21 protein with plasmin. A plasmin processed CCL21 protein therefore includes CCL21 comprising or consisting of a sequence corresponding to amino acids 1-88 of SEQ ID NO:2 or having at least 70%, 72%, 74%, 76%, 78%, 80%, 85%, 89%, 90%, 91%, 92%, 93%, 94%, 95%, 96%, 97%, 98%, 99% or 100% identity to amino acids 1-88 of SEQ ID NO:2. Further, a CCL21 protein includes CCL21 comprising or consisting of a sequence corresponding to amino acids 1-91 of SEQ ID NO:2 or having at least 70%, 72%, 74%, 76%, 78%, 80%, 85%, 89%, 90%, 91%, 92%, 93%, 94%, 95%, 96%, 97%, 98%, 99% or 100% identity to amino acids 1-91 of SEQ ID NO:2. A CCL21 protein also includes CCL21 comprising or consisting of a sequence corresponding to amino acids 1-104 of SEQ ID NO:2 or having at least 70%, 72%, 74%, 76%, 78%, 80%, 85%, 89%, 90%, 91%, 92%, 93%, 94%, 95%, 96%, 97%, 98%, 99% or 100% identity to amino acids 1-104 of SEQ ID NO:2.

C-terminally truncated CCL21 protein is characterized by deletion and/or mutation of amino acid(s) in the extended c-terminus of a CCL21 protein. By deleting and/or mutating amino acids in the extended c-terminus binding to glycosaminoglycans like heparin is thereby reduced. In a preferred embodiment, c-terminally truncated CCL21 protein comprises or consists of SEQ ID NO:2 or has at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, 99% or 100% identity to amino acids 1-79 of SEQ ID NO:2 with the proviso that the protein lacks at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 amino acid residue(s) indicated at positions 80-111, or wherein one or more of said residues is mutated. In a further preferred embodiment, c-terminally truncated CCL21 is a CCL21 comprising or consisting of SEQ ID NO:2 or having at least 70%, 72%, 74%, 76%, 78%, 80%, 81%, 82%, 83%, 84%, 85%, 86%, 87%, 88%, 89%, 90%, 91%, 92%, 93%, 94%, 95%, 96%, 97%, 98%, 99% or 100% identity to amino acids 1-79 of SEQ ID NO:2, wherein all amino acids of 80-111 of SEQ ID NO:2 are deleted (i.e. 32 deletions).

In each case either the plasmin processed CCL21 or the c-terminally truncated CCL21 may further comprise a signal peptide sequence. Particularly preferred are the signal peptide sequences comprising or consisting of the amino acids 1-23 of SEQ ID NO:1 or the amino acids 1-19 of SEQ ID NO:5. Also other signal peptide sequences may be used which replace the original signal peptide sequence. Thus, in a preferred embodiment plasmin processed or c-terminally truncated CCL21 protein comprises or consists of a protein having the following sequence:

(SEQ ID NO: 5)
MGWSCIILFLVATATGVHSSDGGAQDCCLKYSQRKIPAKVVRSYRKQEPSL

GCSIPAILFLPRKRSQAELCADPKELWVQQLMQHLDKTPSPQKPAQG or having at least 70%, 72%, 74%, 76%, 78%, 80%, 85%, 89%, 90%, 91%, 92%, 93%, 94%, 95%, 96%, 97% 98%, 99% or 100% identity to SEQ ID NO:5.

A CCL21 protein may also include CCL21 with a truncated signal peptide sequence. In this context truncated refers to a signal peptide sequence that is shorter than the original signal peptide sequence but still retains at least a portion of its functionality to act as a signal peptide. For example, the human signal peptide sequence comprises or consists of amino acids 1-23 of SEQ ID NO:1. A CCL21 with a truncated signal peptide sequence could have 22, 21, 20, 19, 18, 17, 16, 15, 14, 13, 12, 11, 10, 9, 8, 7, 6, 5, 4, 3, 2 or 1 of the amino acids 1-23 of SEQ ID NO:1. In a further example, the signal peptide could comprise or consist of the sequence as shown in SEQ ID NO:6. A CCL21 with a truncated signal peptide sequence could have 18, 17, 16, 15, 14, 13, 12, 11, 10, 9, 8, 7, 6, 5, 4, 3, 2 or 1 of the amino acids 1-18 of SEQ ID NO:6.

A CCL21 protein with a truncated signal peptide sequence could also be a protein comprising any of the sequences of SEQ ID Nos: 2-4 and in addition a signal peptide sequence that is shorter than the original signal peptide sequence. Again, by way of example signal peptide sequence could have 22, 21, 20, 19, 18, 17, 16, 15, 14, 13, 12, 11, 10, 9, 8, 7, 6, 5, 4, 3, 2 or 1 of the amino acids 1-23 of SEQ ID NO:1 or in a further example, the signal peptide could comprise or consist of the sequence as shown in SEQ ID NO:6. A CCL21 with a truncated signal peptide sequence could have 18, 17, 16, 15, 14, 13, 12, 11, 10, 9, 8, 7, 6, 5, 4, 3, 2 or 1 of the amino acids 1-18 of SEQ ID NO:6.

The CCL21 protein can be of any origin including from mouse and rat. Preferably, the CCL21 protein is from human origin.

Functional variants of a CCL21 protein include biologically active variants and biologically active fragments of the foregoing described CCL21 proteins. Variants may have one or more different amino acids in a position of a specifically described CCL21 protein. Variants can share at least about 50%, 55%, 60%, 65%, 70%, 75%, 80%, 85%, 89%, 90%, 91%, 92%, 93%, 94%, 95%, 96%, 97%, 98% or 99% or more amino acid identity with such a CCL21 protein. Fragments have the same amino acids as a given specifically described CCL21 protein but may lack a specific portion or area of the CCL21 protein.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

In both cases, the functional variants only include variants and fragments of CCL21 that are biologically active. For the invention, the biological activity of the CCL21 variant or the CCL21 fragment—which is encoded in the genome of a recombinant rhabdovirus—is determined after its expression in a respective cell or tumor cell. This means that the biological activity is determined in the context of a recombinant rhabdovirus encoding for the CCL21 variant or the CCL21 fragment (e.g. in a Transwell assay or in vitro tumor model). Preferably, the biological activity is determined with a vesiculovirus encoding for the CCL21 variant or the CCL21 fragment. More preferably, the biological activity is determined with a VSV-GP encoding for the CCL21 variant or the CCL21 fragment.

Biological activity can include one or more of the following abilities: chemoattractant activity, anti-tumor activity, modulation of cytokine expression such as increase in the expression of Interferon-gamma (IFN-gamma) polypeptides or decrease in the expression of transforming growth factor-beta (TGF-beta) polypeptides in a population of syngeneic mammalian cells including CD8 positive T cells, CD4 positive T cells, antigen presenting cells and tumor cells. Testing for biological activity may be done without limitation for example according to the protocol as shown in the Examples. For the purpose of the invention the functional variant or fragment of the CCL21 protein is biologically active if it shows at least 30%, 40%, 50%, 60%, 70%, 80%, 90%, 95%, or 98% of the activity of a CCL21 protein with the sequence as shown in SEQ ID NO:1 or 2 (respectively with or without signal peptide sequence) if tested in the same assay and under the same conditions.

Without wishing to be bound by theory the inventors have found that after treatment of tumor cells with VSV-GP several chemokines and cytokines are upregulated in response. CCL21 is one of the chemokines that is not upregulated in tumor cells after VSV-GP treatment. The present data show that a VSV-GP coding in its genome for a CCL21 protein is particularly effective in treatment of cancer and is geared towards further improving immune cell infiltration into tumors infected by the oncolytic virus and thereby further potentiating anti-tumor immunity.

More surprisingly, recombinant rhabdoviruses encoding a CCL21 protein comprising or containing the sequences of SEQ ID NO:3 or 4 and in particular SEQ ID NO:5 were even more potent and more effective in tumor treatment compared to the full length CCL21 protein and are active without the need for proteolytic processing.

Such CCL21 proteins are further preferred to the full length CCL21 protein due to their smaller size. Larger or multiple transgenes may negatively impact the viability, stability, oncolytic capability, manufacturability or expression of the rhabdovirus as well as the transgene itself. Utilizing smaller transgenes also provides the possibility of adding additional transgenes to rhabdovirus which may have limitations in their capacity to accommodate further transgenes.

Rhabdoviruses have negative sense single-stranded RNA (ssRNA) as their genetic material (genome). Negative sense ssRNA viruses need RNA polymerase to form a positive sense RNA. The positive-sense RNA acts as a viral mRNA, which is translated into proteins for the production of new virus materials. With the newly formed virus, more negative sense RNA molecules are produced.

A typical rhabdovirus genome encodes for at least five structural proteins in the order of 3'-N—P-M-G-L-5'. The genome might contain further short intergenic regions or additional genes between the structural proteins and therefore might vary in length and organization.

According to the invention the CCL21 gene can be introduced into any location of the rhabdovirus genome. Depending on the insertion site the transcription efficiency of the CCL21 gene can be influenced. In general, transcription efficiency of the CCL21 gene decreases from 3' insertion to 5' prime insertion. The CCL21 gene may be inserted into the following genome locations: 3'-CCL21-N—P-M-G-L-5',3'-N—CCL21-P-M-G-L-5',3'-N—P—CCL21-M-G-L-5',3'-N—P-M-CCL21-G-L-5',3'-N—P-M-G-CCL21-L-5' or 3'-N—P-M-G-L-CCL21-5'. In a preferred embodiment the CCL21 gene is inserted between the G protein and the L protein.

After infection of tumor cells the CCL21 gene encoded in the genome of the recombinant rhabdovirus is transcribed into positive sense RNA and then translated into CCL21 protein by the tumor cell. The term "encoding" or "coding" refers to the inherent property of specific sequences of nucleotides in a nucleic acid to serve as templates for synthesis of other polymers and macromolecules in biological processes having a defined sequence of nucleotides (e.g. RNA molecules) or amino acids and the biological properties resulting therefrom. Accordingly, a gene codes for a protein if the desired protein is produced in a cell or another biological system by transcription and subsequent translation of the mRNA. Both the coding strand, the nucleotide sequence of which is identical to the mRNA sequence and the non-coding strand may serve as the template for the transcription of a gene and can be referred to as encoding the protein or other product of that gene. Nucleic acids and nucleotide sequences that encode proteins may include introns.

The transcription of the CCL21 gene is preferably not under the control of its own promoter and only strictly linked to viral replication ensuring thereby targeted expression of CCL21 to the location of viral replication and spread (tumor). Thus, the transcription of the CCL21 gene is not controlled by additional elements such as promoters or inducible gene expression elements.

It will be appreciated that a nucleic acid sequence may be varied with or without changing the primary sequence of the encoded polypeptide. A nucleic acid that encodes a protein includes any nucleic acids that have different nucleotide sequences but encode the same amino acid sequence of the protein due to the degeneracy of the genetic code. It is within the knowledge of the skilled artisan to choose a nucleic acid sequence that will result in the expression of a CCL21 protein and in particular to any specific CCL21 proteins as disclosed herein. Nucleic acid molecules encoding amino acid sequences of CCL21 protein are prepared by a variety of methods known in the art. These methods include, but are not limited to, isolation from a natural source or preparation by oligonucleotide-mediated (or site-directed) mutagenesis, PCR mutagenesis, and cassette mutagenesis of an earlier prepared CCL21 protein.

Pharmaceutical Compositions

The actual pharmaceutically effective amount or therapeutic dosage will of course depend on factors known by those skilled in the art such as age and weight of the patient, route of administration and severity of disease. In any case the recombinant rhabdovirus will be administered at dosages and in a manner which allows a pharmaceutically effective amount to be delivered based upon patient's unique condition.

Generally, for the treatment and/or alleviation of the diseases, disorders and conditions mentioned herein and depending on the specific disease, disorder or condition to be treated, the potency of the specific recombinant rhabdovirus of the invention to be used, the specific route of administration and the specific pharmaceutical formulation or composition used, the recombinant rhabdovirus of the invention will generally be administered for example, twice a week, weekly, or in monthly doses, but can significantly vary, especially, depending on the before-mentioned parameters. Thus, in some cases it may be sufficient to use less than the minimum dose given above, whereas in other cases the upper limit may have to be exceeded. When administering large amounts it may be advisable to divide them up into a number of smaller doses spread over the day.

To be used in therapy, the recombinant rhabdovirus of the invention is formulated into pharmaceutical compositions appropriate to facilitate administration to animals or humans. Typical formulations can be prepared by mixing the recombinant virus with physiologically acceptable carriers, excipients or stabilizers, in the form of aqueous solutions or aqueous or non-aqueous suspensions. Carriers, excipients, modifiers or stabilizers are nontoxic at the dosages and concentrations employed. They include buffer systems such as phosphate, citrate, acetate and other inorganic or organic acids and their salts; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g., Zn-protein complexes); and/or ionic or non-ionic surfactants such as TWEEN™ (polysorbates), PLURONICS™ or fatty acid esters, fatty acid ethers or sugar esters. The excipients may also have a release-modifying or absorption-modifying function.

In one embodiment the recombinant rhabdovirus of the invention is formulated into a pharmaceutical composition comprising Tris, arginine and optionally citrate. Tris is preferably used in a concentration of about 1 mM to about 100 mM. Arginine is preferably used in a concentration of about 1 mM to about 100 mM. Citrate may be present in a concentration up to 100 mM. A preferred formulation comprises about 50 mM Tris and 50 mM arginine.

The pharmaceutical composition may be provided as a liquid, a frozen liquid or in a lyophilized form. The frozen liquid may be stored at temperatures between about 0° C. and about −85° C. including temperatures between −70° C. and −85° C. and of about −15° C., −16° C., −17° C., −18° C., −19° C., −20° C., −21° C., −22° C., −23° C., −24° C. or about −25° C.

The recombinant rhabdovirus or pharmaceutical composition of the invention need not be, but is optionally, formulated with one or more agents currently used to prevent or treat the disorder in question. The effective amount of such other agents depends on the amount of recombinant antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the recombinant rhabodvirus or pharmaceutical composition of the invention (when used alone or in combination with one or more other additional therapeutic agents) will depend on the type of disease to be treated, the type of recombinant rhabdovirus, the severity and course of the disease, whether the recombinant rhabdovirus is administered for preventive or therapeutic purposes, previous therapy, the patient's clinical history and response to the recombinant rhabdovirus, and the discretion of the attending physician. The recombinant rhabdovirus or pharmaceutical composition of the invention suitably administered to the patient at one time or over a series of treatments.

Depending on the type and severity of the disease, about $10^8$ to $10^{13}$ infectious particles measured by $TCID_{50}$ of the recombinant rhabdovirus can be an initial candidate dosage for administration to the patient, whether, for example, by one or more separate administrations, or by continuous infusion. For repeated administrations over several days or longer, depending on the condition, the treatment would generally be sustained until a desired suppression of disease symptoms occurs. One exemplary dosage of the recombinant rhabdovirus would be in the range from about $10^8$ to $10^{13}$ infectious particles measured by $TCID_{50}$. Thus, one or more doses of about $10^8$, $10^9$, $10^{10}$, $10^{11}$, $10^{12}$, or $10^{13}$ infectious particles measured by $TCID_{50}$ (or any combination thereof) may be administered to the patient. Such doses may be administered intermittently, e.g. every week or every three weeks (e.g. such that the patient receives from about two to about twenty, or e.g. about six doses of the recombinant rhabdovirus). An initial higher loading dose, followed by one or more lower doses or vice versa may be administered. However, other dosage regimens may be useful. The progress of this therapy is easily monitored by conventional techniques and assays.

The efficacy of the recombinant rhabdovirus of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

The actual pharmaceutically effective amount or therapeutic dosage will of course depend on factors known by those skilled in the art such as age and weight of the patient, route of administration and severity of disease. In any case the recombinant rhabdovirus of the invention will be administered at dosages and in a manner which allows a pharmaceutically effective amount to be delivered based upon patient's unique condition.

Alternatively, the recombinant rhabdovirus or pharmaceutical composition of the invention may be delivered in a volume of from about 50 µl to about 100 ml including all numbers within the range, depending on the size of the area to be treated, the viral titer used, the route of administration, and the desired effect of the method.

For intratumoral administration the volume is preferably between about 50 µl to about 5 ml including volumes of about 100 µl, 200 µl, 300 µl, 400 µl, 500 µl, 600 µl, 700 µl, 800 µl, 900 µl, 1000 µl, 1100 µl, 1200 µl, 1300 µl, 1400 µl, 1500 µl, 1600 µl, 1700 µl, 1800 µl, 1900 µl, 2000 µl, 2500 µl, 3000 µl, 3500 µl, 4000 µl, or about 4500 µl. In a preferred embodiment the volume is about 1000 µl.

For systemic administration, e.g. by infusion of the recombinant rhabdovirus the volumes may be naturally higher. Alternatively, a concentrated solution of the recombinant rhabdovirus could be diluted in a larger volume of infusion solution directly before infusion.

In particular for intravenous administration the volume is preferably between 1 ml and 100 ml including volumes of about 2 ml, 3 ml, 4 ml, 5 ml, 6 ml, 7 ml, 8 ml, 9 ml, 10 ml, 11 ml, 12 ml, 13 ml, 14 ml, 15 ml, 16 ml, 17 ml, 18 ml, 19 ml, 20 ml, 25 ml, 30 ml, 35 ml, 40 ml, 45 ml, 50 ml, 55 ml, 60 ml, 70 ml, 75 ml, 80 ml, 85 ml, 90 ml, 95 ml, or about 100 ml. In a preferred embodiment the volume is between about 5 ml and 15 ml, more preferably the volume is about 6 ml, 7 ml, 8 ml, 9 ml, 10 ml, 11 ml, 12 ml, 13 ml, or about 14 ml.

Preferably the same formulation is used for intratumoral administration and intravenous administration. The doses and/or volume ratio between intratumoral and intravenous administration may be about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or about 1:20. For example, a doses and/or volume ratio of 1:1 means that the same doses and/or volume is administered intratumorally as well as intravenously, whereas e.g. a doses and/or volume ratio of about 1:20 means an intravenous administration dose and/or volume that is twenty times higher than the intratumoral administration dose and/or volume. Preferably, the doses and/or volume ratio between intratumoral and intravenous administration is about 1:9.

An effective concentration of a recombinant rhabdovirus desirably ranges between about $10^8$ and $10^{14}$ vector genomes per milliliter (vg/mL). The infectious units may be measured as described in McLaughlin et al., J Virol.; 62(6):1963-73 (1988). Preferably, the concentration is from about $1.5 \times 10^9$ to about $1.5 \times 10^{13}$, and more preferably from about $1.5 \times 10^9$ to about $1.5 \times 10^{11}$. In one embodiment, the effective concentration is about $1.5 \times 10^9$. In another embodiment, the effective concentration is about $1.5 \times 10^{10}$. In another embodiment, the effective concentration is about $1.5 \times 10^{11}$. In yet another embodiment, the effective concentration is about $1.5 \times 10^{12}$. In another embodiment, the effective concentration is about $1.5 \times 10^{13}$. In another embodiment, the effective concentration is about $1.5 \times 10^{14}$. It may be desirable to use the lowest effective concentration in order to reduce the risk of undesirable effects. Still other dosages in these ranges may be selected by the attending physician, taking into account the physical state of the subject, preferably human, being treated, the age of the subject, the particular type of cancer and the degree to which the cancer, if progressive, has developed.

An effective target concentration of a recombinant rhabdovirus may be expressed with the $TCID_{50}$. The $TCID_{50}$ can be determined for example by using the method of Spearman-Karber. Desirably ranges include an effective target concentration between $1 \times 10^8$/ml and $1 \times 10^{14}$/ml $TCID_{50}$. Preferably, the effective target concentration is from about $1 \times 10^9$ to about $1 \times 10^{12}$/ml, and more preferably from about $1 \times 10^9$ to about $1 \times 10^{11}$/ml. In one embodiment, the effective target concentration is about $1 \times 10^{10}$/ml. In a preferred embodiment the target concentration is $5 \times 10^{10}$/ml. In another embodiment, the effective target concentration is about $1.5 \times 10^{11}$/ml. In one embodiment, the effective target concentration is about $1 \times 10^{12}$/ml. In another embodiment, the effective target concentration is about $1.5 \times 10^{13}$/ml.

An effective target dose of a recombinant rhabdovirus may also be expressed with the $TCID_{50}$. Desirably ranges include a target dose between $1 \times 10^8$ and $1 \times 10^{14}$ $TCID_{50}$. Preferably, the target dose is from about $1 \times 10^9$ to about $1 \times 10^{13}$, and more preferably from about $1 \times 10^9$ to about $1 \times 10^{12}$. In one embodiment, the effective concentration is about $1 \times 10^{10}$. In a preferred embodiment, the effective concentration is about $1 \times 10^{11}$. In one embodiment, the effective concentration is about $1 \times 10^{12}$. In another embodiment, the effective concentration is about $1 \times 10^{13}$.

In another aspect, a kit or kit-of-parts containing materials useful for the treatment, prevention and/or diagnosis of the disorders described herein is provided. The kit or kit-of-parts comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is the recombinant rhabdovirus or pharmaceutical composition of the invention. The label or package insert indicates that the composition is used for treating the condition of choice.

Moreover, the kit or kit-of-parts may comprise (a) a first container with a composition contained therein, wherein the composition comprises the recombinant rhabdovirus or pharmaceutical composition of the invention; and (b) a second container with a composition contained therein, wherein the composition comprises a further cytotoxic or otherwise therapeutic agent, such as a PD-1 pathway inhibitor or SMAC mimetic. The kit or kit-of-parts in this embodiment of the invention may further comprise a package insert indicating that the compositions can be used to treat a particular condition, in particular cancer. Alternatively, or additionally, the kit or kit-of-parts may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In a further aspect, a recombinant rhabdovirus of the invention is used in combination with a device useful for the administration of the recombinant rhabdovirus, such as a syringe, injector pen, micropump, or other device. Preferably, a recombinant rhabdovirus of the invention is comprised in a kit of parts, for example also including a package insert with instructions for the use of the recombinant rhabdovirus.

Medical Uses

A further aspect of the invention provides a recombinant rhabdovirus encoding in its genome at least one CCL21 protein or a functional variant thereof for use in medicine.

The recombinant rhabdovirus of the invention efficiently induces tumor cell lysis combined with immunogenic cell death and stimulation of innate immune cells in the tumor microenvironment. Accordingly, the recombinant rhabdovirus of the invention are useful for the treatment and/or prevention of cancer.

In a further aspect, the recombinant rhabdovirus of the invention can be used in a method for treating and/or preventing cancer, comprising administering a therapeutically effective amount of a recombinant rhabdovirus to an individual suffering from cancer, thereby ameliorating one or more symptoms of cancer.

In yet a further aspect the invention further provides for the use of a recombinant rhabdovirus according to the invention for the manufacture of a medicament for treatment and/or prevention of cancer.

In yet a further aspect, the recombinant rhabdovirus of the invention can be used in a method for treating and/or preventing gastrointestinal cancer, lung cancer or head & neck cancer, comprising administering a therapeutically effective amount of a recombinant rhabdovirus to an individual suffering from gastrointestinal cancer, lung cancer or head & neck cancer, thereby ameliorating one or more symptoms of gastrointestinal cancer, lung cancer or head & neck cancer.

For the prevention or treatment of a disease, the appropriate dosage of recombinant rhabdovirus will depend on a variety of factors such as the type of disease to be treated, as defined above, the severity and course of the disease, whether the recombinant rhabdovirus is administered for preventive or therapeutic purposes, previous therapy, the patient's clinical history and response to the recombinant rhabdovirus, and the discretion of the attending physician. The recombinant rhabdovirus is suitably administered to the patient at one time or over a series of treatments.

In one aspect, the cancer is a solid cancer. The solid cancer may be brain cancer, colorectal cancer, oropharyngeal squamous cell carcinoma, gastric cancer, gastroesophageal junction adenocarcinoma, esophageal carcinoma, hepatocellular carcinoma, pancreatic adenocarcinoma, cholangiocarcinoma, bladder urothelial carcinoma, metastatic melanoma, prostate carcinoma, breast carcinoma, a head and neck squamous-cell carcinoma (HNSCC), glioblastoma, non-small cell lung cancer, brain tumor or small cell lung cancer. Preferred is the treatment of gastrointestinal cancer, lung cancer and head & neck cancer.

The recombinant rhabdovirus is administered by any suitable means, including oral, parenteral, subcutaneous, intratumoral, intravenous, intradermal, intraperitoneal, intrapulmonary, and intranasal. Parenteral infusions include intramuscular, intravenous, intraarterial, intraperitoneal, or subcutaneous administration. In addition, the recombinant rhabdovirus is suitably administered by pulse infusion. In one aspect, the dosing is given by injections, most preferably intravenous or subcutaneous injections, depending in part on whether the administration is brief or chronic.

Depending on the specific recombinant rhabdovirus of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The treatment schedule may include various regimens and in typical will require multiple doses administered to the patient over a period of one, two, three or four weeks optionally followed by one or more further rounds of treatment. In one aspect, the recombinant rhabdovirus of the invention is administered to the patient in up to 1, 2, 3, 4, 5, or 6 doses within a given period of time. Preferably, the first round of treatment(s) is concluded within three weeks. During the course of the three week treatment the recombinant rhabdovirus may be administered to the patient as described in the following schemes: (i) once on day 0 (ii) on day 0 and day 3; (iii) on day 0, day 3 and day 6; (iv) on day 0, day 3, day 6, and day 9; (v) on day 0 and day 5; (vi) on day 0, day 5 and day 10; (vii) on day 0, day 5, day 10 and day 15. These regimens may be repeated and a second or third round of treatment may be needed depending on the outcome of the first round of treatment. Calculated on the basis of the first round of treatments the second round of treatment preferably includes further treatments on day 21, day 42 and day 63. In a preferred embodiment the recombinant rhabdovirus of the invention is administered to the patient according the following scheme: on day 0, day 3, day 21, day 42 and day 63.

The term "suppression" is used herein in the same context as "amelioration" and "alleviation" to mean a lessening or diminishing of one or more characteristics of the disease. The recombinant rhabdovirus or pharmaceutical composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the recombinant rhabdovirus to be administered will be governed by such considerations, and is the minimum amount necessary to prevent, ameliorate, or treat clinical symptoms of cancer, in particular the minimum amount which is effective to these disorders.

In another aspect the recombinant rhabdovirus of the invention can be administered multiple times and in several doses. In one aspect, the first dose of the recombinant rhabdovirus is administered intratumorally and subsequent doses of the recombinant rhabdovirus are administered intravenously. In a further aspect, the first dose and at least one or more following doses of the recombinant rhabdovirus is/are administered intratumorally and subsequent doses of the recombinant rhabdovirus are administered intravenously. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration.

In another aspect, the first dose of the recombinant rhabdovirus is administered intravenously and subsequent doses of the recombinant rhabdovirus are administered intratumorally. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intravenous administration.

In another aspect, the recombinant rhabdovirus is administered intravenously and subsequent doses of the recombinant rhabdovirus are administered intratumorally.

In another aspect, the recombinant rhabdovirus is administered at each time point intravenously and intratumorally.

As stated above, the recombinant rhabdovirus of the invention have much utility for stimulating an immune response against cancer cells. The strong immune activating potential was observed to be restricted to the tumor microenvironment. Thus, in a preferred aspect, the recombinant rhabdovirus of the invention may be administered systemically to a patient. Systemic applicability is a crucial attribute, as many cancers are highly metastasized and it will permit the treatment of difficult to access as well as non-accessible tumor lesions. Due to this unique immune stimulating properties the recombinant rhabdovirus according to the invention are especially useful for treatment of metastasizing tumors.

Some patients develop resistance to checkpoint inhibitor therapy and it was observed that such patients seem to accumulate mutations in the IFN pathway. Therefore in one aspect, the recombinant rhabdovirus of the invention and in particular the recombinant vesicular stomatitis virus of the invention is useful for the treatment of patients who developed a resistance to checkpoint inhibitor therapy. Due to the unique immune promoting properties of the recombinant rhabdovirus and in particular the recombinant vesicular stomatitis virus of the invention such treated patients may become eligible for continuation of checkpoint inhibitor therapy.

In a preferred embodiment, the recombinant rhabdovirus of the invention and in particular the recombinant vesicular stomatitis virus of the invention is useful for the treatment of patients with non-small cell lung cancer which have completed checkpoint inhibitor therapy with either a PD-1 or PD-L1 inhibitor, e.g. antagonistic antibodies to PD-1 or PD-L1.

It is understood that any of the above pharmaceutical formulations or therapeutic methods may be carried out using any one of the inventive recombinant rhabdovirus or pharmaceutical compositions.

Combinations

The present invention also provide combination treatments/methods providing certain advantages compared to treatments/methods currently used and/or known in the prior art. These advantages may include in vivo efficacy (e.g. improved clinical response, extend of the response, increase of the rate of response, duration of response, disease stabilization rate, duration of stabilization, time to disease progression, progression free survival (PFS) and/or overall survival (OS), later occurrence of resistance and the like), safe and well tolerated administration and reduced frequency and severity of adverse events.

The recombinant rhabdovirus of the invention may be used in combination with other pharmacologically active ingredients, such as state-of-the-art or standard-of-care compounds, such as e.g. cytostatic or cytotoxic substances, cell proliferation inhibitors, anti-angiogenic substances, steroids, immune modulators/checkpoint inhibitors, and the like.

Cytostatic and/or cytotoxic active substances which may be administered in combination with recombinant rhabdovirus of the invention include, without being restricted thereto, hormones, hormone analogues and antihormones, aromatase inhibitors, LHRH agonists and antagonists, inhibitors of growth factors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF)), inhibitors are for example (anti-) growth factor antibodies, (anti-)growth factor receptor antibodies and tyrosine kinase inhibitors, such as for example cetuximab, gefitinib, afatinib, nintedanib, imatinib, lapatinib, bosutinib and trastuzumab; antimetabolites (e.g. antifolates such as methotrexate, raltitrexed, pyrimidine analogues such as 5-fluorouracil (5-FU), gemcitabine, irinotecan, doxorubicin, TAS-102, capecitabine and gemcitabine, purine and adenosine analogues such as mercaptopurine, thioguanine, cladribine and pentostatin, cytarabine (ara C), fludarabine); antitumor antibiotics (e.g. anthracyclins); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors, including bevacizumab, ramucirumab and aflibercept, tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK33 inhibitors, AKT inhibitors, PLK1 inhibitors (such as volasertib), inhibitors of CDKs, including CDK9 inhibitors, Aurora kinase inhibitors), tyrosine kinase inhibitors (e.g. PTK2/FAK inhibitors), protein protein interaction inhibitors, MEK inhibitors, ERK inhibitors, FLT3 inhibitors, BRD4 inhibitors, IGF-1R inhibitors, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, immunotherapeutic agents such as immune checkpoint inhibitors (e.g. CTLA4, PD1, PD-L1, LAG3, and TIM3 binding molecules/immunoglobulins, such as ipilimumab, nivolumab, pembrolizumab) and various chemotherapeutic agents such as amifostin, anagrelid, clodronat, filgrastin, interferon, interferon alpha, leucovorin, rituximab, procarbazine, levamisole, mesna, mitotane, pamidronate and porfimer; proteasome inhibitors (such as Bortezomib); Smac and BH3 mimetics; agents restoring p53 functionality including mdm2-p53 antagonist; inhibitors of the Wnt/beta-catenin signaling pathway; and/or cyclin-dependent kinase 9 inhibitors.

The recombinant rhabdovirus of the invention can be used in combination treatment with either a PD-1 pathway inhibitor or a SMACm/IAP antagonist. Such a combined treatment may be given as a non-fixed (e.g. free) combination of the substances or in the form of a fixed combination, including kit-of-parts.

In this context, "combination" or "combined" within the meaning of this invention includes, without being limited, a product that results from the mixing or combining of more than one active agent and includes both fixed and non-fixed (e.g. free) combinations (including kits) and uses, such as e.g. the simultaneous, concurrent, sequential, successive, alternate or separate use of the components or agents. The term "fixed combination" means that the active agents are both administered to a patient simultaneously in the form of a single entity or dosage. The term "non-fixed combination" means that the active agents are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active agents.

The invention provides for a recombinant rhabdovirus in combination with a PD-1 pathway inhibitor or a SMACm/IAP antagonist for use in the treatment of cancers as described herein, preferably for the treatment of solid cancers.

The invention also provides for the use of a recombinant rhabdovirus in combination with a PD-1 pathway inhibitor or a SMACm/IAP antagonist for the manufacture of a medicament for treatment and/or prevention of cancers as described herein, preferably for the treatment of solid cancers.

The invention further provides for a method for treating and/or preventing cancer, comprising administering a therapeutically effective amount of a recombinant rhabdovirus of the invention, and a PD-1 pathway inhibitor or a SMACm/IAP antagonist to an individual suffering from cancer, thereby ameliorating one or more symptoms of cancer. The recombinant rhabdovirus of the invention and the PD-1 pathway inhibitor or the SMACm/IAP antagonist may be administered concomitantly, sequentially or alternately.

The recombinant rhabdovirus of the invention and the PD-1 pathway inhibitor or a SMACm/IAP antagonist may be administered by the same administration routes or via different administration routes. Preferably, the PD-1 pathway inhibitor or SMACm/IAP antagonist is administered intravenously and the recombinant rhabdovirus of the invention is administered intratumorally. In another embodiment, the PD-1 pathway inhibitor or the SMACm/IAP antagonist is administered intravenously and the recombinant rhabdovirus of the invention is administered at least once intratumorally and subsequent doses of the recombinant rhabdovirus are administered intravenously. The subsequent doses may be administered 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration. In a preferred embodiment the PD-1 pathway inhibitor or the SMACm/IAP antagonists is administered 21 days after the initial intratumoral administration.

Particularly preferred are treatments with the recombinant rhabdovirus of the invention in combination with:
(i) SMAC mimetica (SMACm)/IAP antagonists,
(ii) immunotherapeutic agents, including anti-PD-1 and anti-PD-L1 agents and anti LAG3 agents, such as pembrolizumab and nivolumab and antibodies as disclosed in WO2017/198741.

A combination as herein provided comprises (i) a recombinant rhabdovirus of the invention and (iia) a PD-1 pathway inhibitor, preferably an antagonistic antibody which is directed against PD-1 or PD-L1 or (iib) a SMACm/IAP antagonists. Further provided is the use of such a combination comprising (i) and (iia) or (i) and (iib) for the treatment of cancers as described herein.

In another aspect a combination treatment is provided comprising the use of (i) a recombinant rhabdovirus of the invention and (iia) a PD-1 pathway inhibitor or (iib) a SMACm/IAP antagonists. In such combination treatment the recombinant rhabdovirus of the invention may be administered concomitantly, sequentially or alternately with the PD-1 pathway inhibitor or SMACm/IAP antagonists.

For example, "concomitant" administration includes administering the active agents within the same general time period, for example on the same day(s) but not necessarily at the same time. Alternate administration includes administration of one agent during a time period, for example over the course of a few days or a week, followed by administration of the other agent during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent during a second time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

Sequential treatment schedules include administration of the recombinant rhabdovirus of the invention followed by administration of the PD-1 pathway inhibitor or the SMACm/IAP antagonists. Sequential treatment schedules also include administration of the PD-1 pathway inhibitor or the SMACm/IAP antagonists followed by administration of the recombinant rhabdovirus of the invention. Sequential treatment schedules may include administrations 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after each other.

A PD-1 pathway inhibitor within the meaning of this invention and all of its embodiments is a compound that inhibits the interaction of PD-1 with its receptor(s). A PD-1 pathway inhibitor is capable to impair the PD-1 pathway signaling, preferably mediated by the PD-1 receptor. The PD-1 inhibitor may be any inhibitor directed against any member of the PD-1 pathway capable of antagonizing PD-1 pathway signaling. The inhibitor may be an antagonistic antibody targeting any member of the PD-1 pathway, preferably directed against PD-1 receptor, PD-L1 or PD-L2. Also, the PD-1 pathway inhibitor may be a fragment of the PD-1 receptor or the PD-1 receptor blocking the activity of PD1 ligands.

PD-1 antagonists are well-known in the art, e.g. reviewed by Li et al., Int. J. Mol. Sci. 2016, 17, 1151 (incorporated herein by reference). Any PD-1 antagonist, especially antibodies, such as those disclosed by Li et al. as well as the further antibodies disclosed herein below, can be used according to the invention. Preferably, the PD-1 antagonist of this invention and all its embodiments is selected from the group consisting of the following antibodies:
pembrolizumab (anti-PD-1 antibody);
nivolumab (anti-PD-1 antibody);
pidilizumab (anti-PD-1 antibody);
PDR-001 (anti-PD-1 antibody);
PD1-1, PD1-2, PD1-3, PD1-4, and PD1-5 as disclosed herein below (anti-PD-1 antibodies)
atezolizumab (anti-PD-L1 antibody);
avelumab (anti-PD-L1 antibody);
durvalumab (anti-PD-L1 antibody).

Pembrolizumab (formerly also known as lambrolizumab; trade name Keytruda; also known as MK-3475) disclosed e.g. in Hamid, O. et al. (2013) New England Journal of Medicine 369(2):134-44, is a humanized IgG4 monoclonal antibody that binds to PD-1; it contains a mutation at C228P designed to prevent Fc-mediated cytotoxicity. Pembrolizumab is e.g. disclosed in U.S. Pat. No. 8,354,509 and WO2009/114335. It is approved by the FDA for the treatment of patients suffering from unresectable or metastatic melanoma and patients with metastatic NSCLC.

Nivolumab (CAS Registry Number: 946414-94-4; BMS-936558 or MDX1106b) is a fully human IgG4 monoclonal antibody which specifically blocks PD-1, lacking detectable antibody-dependent cellular toxicity (ADCC). Nivolumab is e.g. disclosed in U.S. Pat. No. 8,008,449 and WO2006/121168. It has been approved by the FDA for the treatment of patients suffering from unresectable or metastatic melanoma, metastatic NSCLC and advanced renal cell carcinoma.

Pidilizumab (CT-011; Cure Tech) is a humanized IgG1k monoclonal antibody that binds to PD-1. Pidilizumab is e.g. disclosed in WO2009/101611.

PDR-001 or PDR001 is a high-affinity, ligand-blocking, humanized anti-PD-1 IgG4 antibody that blocks the binding of PD-L1 and PD-L2 to PD-1. PDR-001 is disclosed in WO2015/112900 and WO2017/019896.

Antibodies PD1-1 to PD1-5 are antibody molecules defined by the sequences as shown in Table 1, wherein HC denotes the (full length) heavy chain and LC denotes the (full length) light chain:

TABLE 1

| SEQ ID NO: | Sequence name | Amino acid sequence |
|---|---|---|
| 14 | HC of PD1-1 | EVMLVESGGGLVQPGGSLRLSCTASGFTFSASAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNVDH KPSNTKVDKRVESKYGPPCPPCPAPEFLGGPSVFLFPPKPKDTLMISRTPEVTC VVVDVSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTVDKSR WQEGNVFSCSVMHEALHNHYTQKSLSLSLG |
| 15 | LC of PD1-1 | EIVLTQSPATLSLSPGERATMSCRASENIDTSGISFMNWYQQKPGQAPKLLIYV ASNQGSGIPARFSGSGSGTDFTLTISRLEPEDFAVYYCQQSKEVPWTFGQGTK LEIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSF NRGEC |
| 16 | HC of PD1-2 | EVMLVESGGGLVQPGGSLRLSCTASGFTFSASAMSWVRQAPGKGLEWVAYI SGGGGDTYYSSSVKGRFTISRDNAKNSLYLQMNSLRAEDTAVYYCARHSNP NYYAMDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNVDH KPSNTKVDKRVESKYGPPCPPCPAPEFLGGPSVFLFPPKPKDTLMISRTPEVTC VVVDVSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTVDKSR WQEGNVFSCSVMHEALHNHYTQKSLSLSLG |
| 17 | LC of PD1-2 | EIVLTQSPATLSLSPGERATMSCRASENIDTSGISFMNWYQQKPGQAPKLLIYV ASNQGSGIPARFSGSGSGTDFTLTISRLEPEDFAVYYCQQSKEVPWTFGQGTK LEIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSF NRGEC |
| 18 | HC of PD1-3 | EVMLVESGGGLVQPGGSLRLSCTASGFTFSKSAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNVDH KPSNTKVDKRVESKYGPPCPPCPAPEFLGGPSVFLFPPKPKDTLMISRTPEVTC VVVDVSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTVDKSR WQEGNVFSCSVMHEALHNHYTQKSLSLSLG |
| 19 | LC of PD1-3 | EIVLTQSPATLSLSPGERATMSCRASENIDVSGISFMNWYQQKPGQAPKLLIY VASNQGSGIPARFSGSGSGTDFTLTISRLEPEDFAVYYCQQSKEVPWTFGQGT KLEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVT KSFNRGEC |
| 20 | HC of PD1-4 | EVMLVESGGGLVQPGGSLRLSCTASGFTFSKSAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNVDH KPSNTKVDKRVESKYGPPCPPCPAPEFLGGPSVFLFPPKPKDTLMISRTPEVTC VVVDVSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTVDKSR WQEGNVFSCSVMHEALHNHYTQKSLSLSLG |

TABLE 1-continued

| SEQ ID NO: | Sequence name | Amino acid sequence |
|---|---|---|
| 21 | LC of PD1-4 | EIVLTQSPATLSLSPGERATMSCRASENIDVSGISFMNWYQQKPGQAPKLLIY VASNQGSGIPARFSGSGSGTDFTLTISRLEPEDFAVYYCQQSKEVPWTFGQGT KLEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVT KSFNRGEC |
| 22 | HC of PD1-5 | EVMLVESGGGLVQPGGSLRLSCTASGFTFSKSAMSWVRQAPGKGLEWVAYI SGGGGDTYYSSSVKGRFTISRDNAKNSLYLQMNSLRAEDTAVYYCARHSNV NYYAMDYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNVDH KPSNTKVDKRVESKYGPPCPPCPAPEFLGGPSVFLFPPKPKDTLMISRTPEVTC VVVDVSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTVDKSR WQEGNVFSCSVMHEALHNHYTQKSLSLSLG |
| 23 | LC of PD1-5 | EIVLTQSPATLSLSPGERATMSCRASENIDVSGISFMNWYQQKPGQAPKLLIY VASNQGSGIPARFSGSGSGTDFTLTISRLEPEDFAVYYCQQSKEVPWTFGQGT KLEIKRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVT KSFNRGEC |

Specifically, the anti-PD-1 antibody molecule described herein above has:
(PD1-1:) a heavy chain comprising the amino acid sequence of SEQ ID NO:14 and a light chain comprising the amino acid sequence of SEQ ID NO:15; or
(PD1-2:) a heavy chain comprising the amino acid sequence of SEQ ID NO:16 and a light chain comprising the amino acid sequence of SEQ ID NO:17; or
(PD1-3:) a heavy chain comprising the amino acid sequence of SEQ ID NO:18 and a light chain comprising the amino acid sequence of SEQ ID NO:19; or
(PD1-4:) a heavy chain comprising the amino acid sequence of SEQ ID NO:20 and a light chain comprising the amino acid sequence of SEQ ID NO:21; or
(PD1-5:) a heavy chain comprising the amino acid sequence of SEQ ID NO:22 and a light chain comprising the amino acid sequence of SEQ ID NO:23.

Atezolizumab (Tecentriq, also known as MPDL3280A) is a phage-derived human IgG1k monoclonal antibody targeting PD-L1 and is described e.g. in Deng et al. mAbs 2016; 8:593-603. It has been approved by the FDA for the treatment of patients suffering from urothelial carcinoma.

Avelumab is a fully human anti-PD-L1 IgG1 monoclonal antibody and described in e.g. Boyerinas et al. Cancer Immunol. Res. 2015; 3:1148-1157.

Durvalumab (MED14736) is a human IgG1k monoclonal antibody with high specificity to PD-L1 and described in e.g. Stewart et al. Cancer Immunol. Res. 2015; 3:1052-1062 or in Ibrahim et al. Semin. Oncol. 2015; 42:474-483.

Further PD-1 antagonists disclosed by Li et al. (supra), or known to be in clinical trials, such as AMP-224, MED10680 (AMP-514), REGN2810, BMS-936559, JS001-PD-1, SHR-1210, BMS-936559, TSR-042, JNJ-63723283, MED14736, MPDL3280A, and MSB0010718C, may be used as alternative or in addition to the above mentioned antagonists.

The INNs as used herein are meant to also encompass all biosimilar antibodies having the same, or substantially the same, amino acid sequences as the originator antibody, including but not limited to those biosimilar antibodies authorized under 42 USC § 262 subsection (k) in the US and equivalent regulations in other jurisdictions.

PD-1 antagonists listed above are known in the art with their respective manufacture, therapeutic use and properties.

In one embodiment the PD-1 antagonist is pembrolizumab.
In another embodiment the PD-1 antagonist is nivolumab.
In another embodiment the PD-1 antagonist is pidilizumab.
In another embodiment the PD-1 antagonist is atezolizumab.
In another embodiment the PD-1 antagonist is avelumab.
In another embodiment the PD-1 antagonist is durvalumab.
In another embodiment the PD-1 antagonist is PDR-001.
In another embodiment the PD-1 antagonist is PD1-1.
In another embodiment the PD-1 antagonist is PD1-2.
In another embodiment the PD-1 antagonist is PD1-3.
In another embodiment the PD-1 antagonist is PD1-4.
In another embodiment the PD-1 antagonist is PD1-5.

The SMAC mimetic within the meaning of this invention and all its embodiments is a compound which binds to IAP proteins and induces their degradation. Preferably, the SMAC mimetic within this invention and all its embodiments is selected from the group consisting of the following (A0):
a SMAC mimetic (i.e. a compound) as (generically and/or specifically) disclosed in WO 2013/127729, or a pharmaceutically acceptable salt thereof;
a SMAC mimetic (i.e. a compound) as (generically and/or specifically) disclosed in WO 2015/025018, or a pharmaceutically acceptable salt thereof;
a SMAC mimetic (i.e. a compound) as (generically and/or specifically) disclosed in WO 2015/025019, or a pharmaceutically acceptable salt thereof;
a SMAC mimetic (i.e. a compound) as (generically and/or specifically) disclosed in WO 2016/023858, or a pharmaceutically acceptable salt thereof;
a SMAC mimetic (i.e. a compound) as (generically and/or specifically) disclosed in WO 2008/0016893, or a pharmaceutically acceptable salt thereof;
LCL161, i.e. compound A in example 1 of WO 2008/016893 (page 28/29; [122]), or a pharmaceutically acceptable salt thereof;

the SMAC mimetic known as Debio-1143, or a pharmaceutically acceptable salt thereof;

the SMAC mimetic known as birinapant, or a pharmaceutically acceptable salt thereof;

the SMAC mimetic known as ASTX-660, or a pharmaceutically acceptable salt thereof;

the SMAC mimetic known as CUDC-427, or a pharmaceutically acceptable salt thereof any one of the SMAC mimetics 1 to 26 in table 2 or a pharmaceutically acceptable salt thereof:

TABLE 2

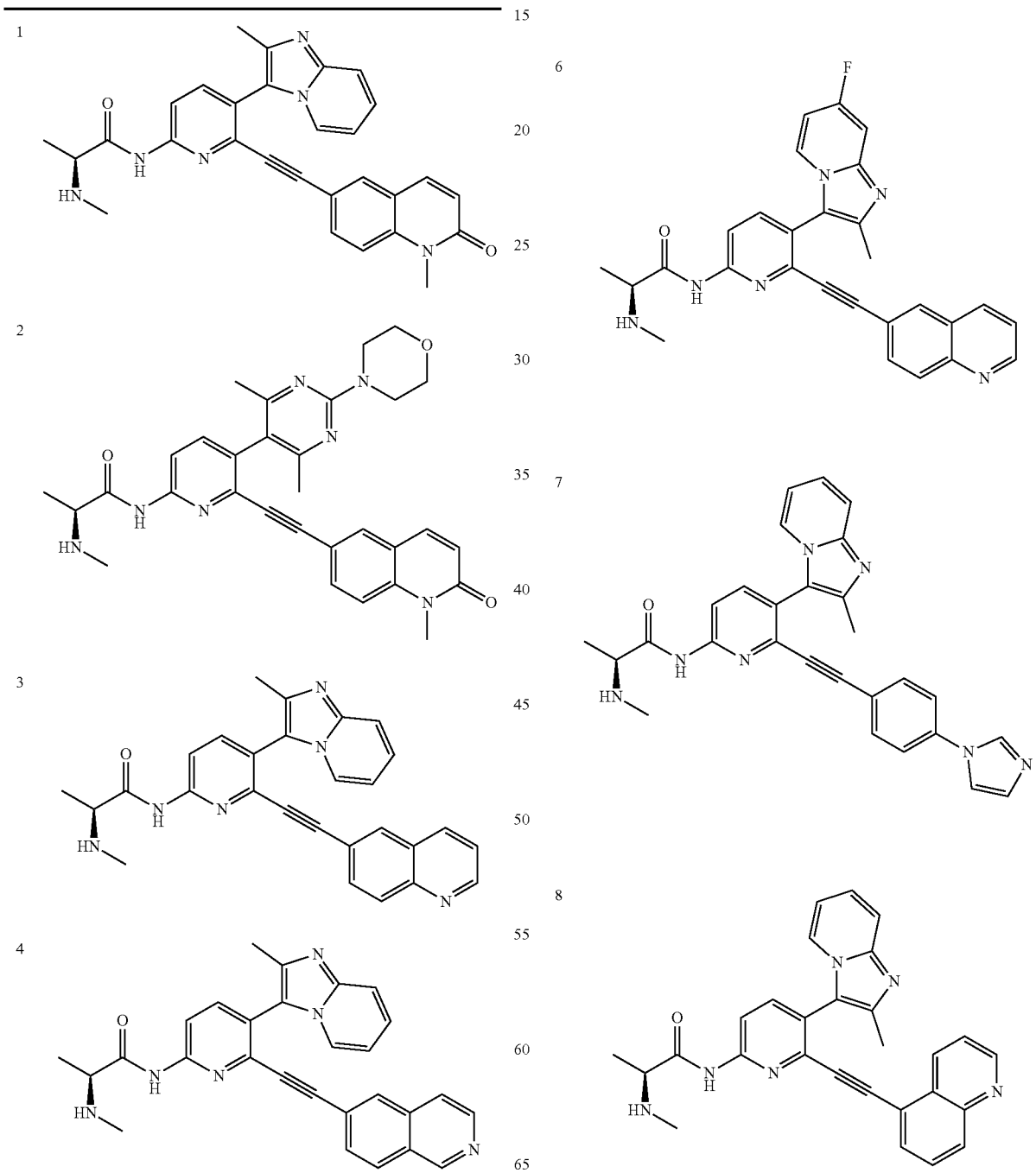

TABLE 2-continued

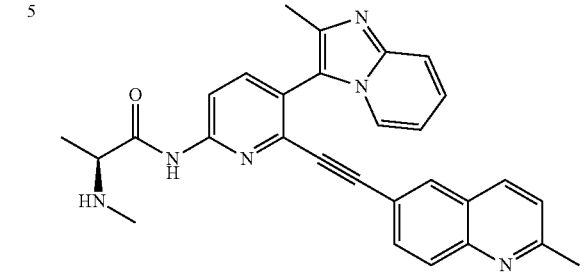

TABLE 2-continued
| | |
|---|---|
| 9 | 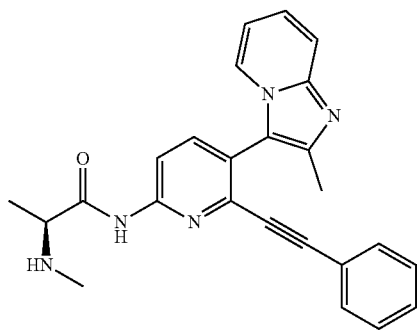 [SMILES: CN[C@@H](C)C(=O)Nc1ccc(-c2c(C)nc3ccccn23)c(C#Cc2ccccc2)n1] |
| 10 | 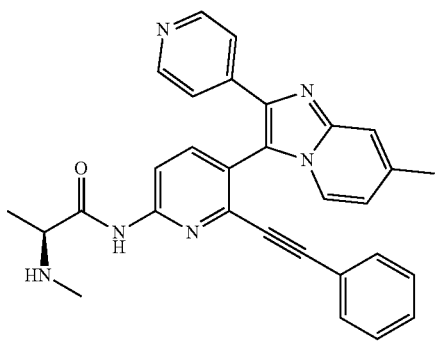 [SMILES: CN[C@@H](C)C(=O)Nc1ccc(-c2c(-c3ccncc3)nc3cc(C)ccn23)c(C#Cc2ccccc2)n1] |
| 11 | 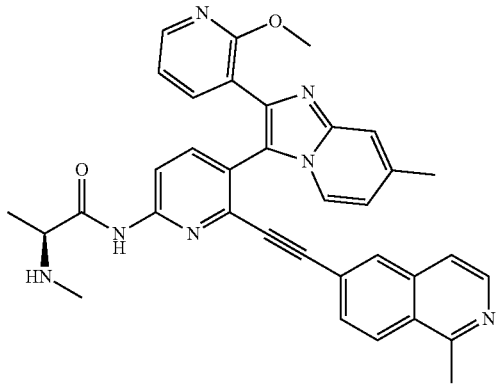 [SMILES: CN[C@@H](C)C(=O)Nc1ccc(-c2c(-c3cccnc3OC)nc3cc(C)ccn23)c(C#Cc2ccc3c(C)nccc3c2)n1] |
| 12 | 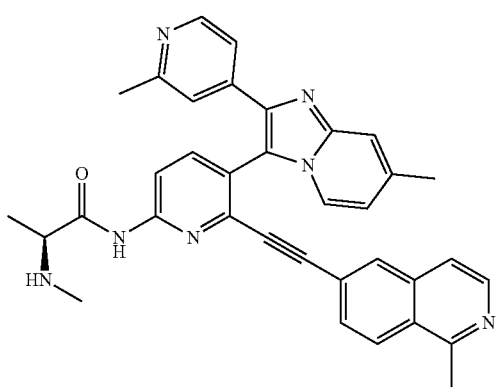 [SMILES: CN[C@@H](C)C(=O)Nc1ccc(-c2c(-c3ccnc(C)c3)nc3cc(C)ccn23)c(C#Cc2ccc3c(C)nccc3c2)n1] |
| 13 | 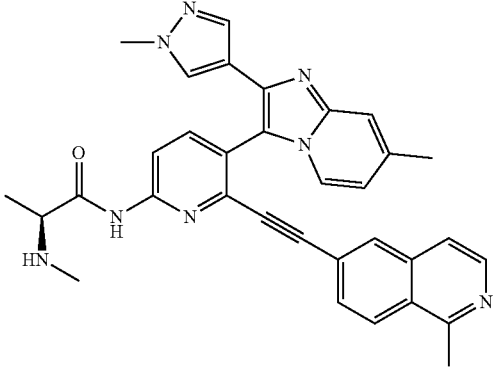 [SMILES: CN[C@@H](C)C(=O)Nc1ccc(-c2c(-c3cnn(C)c3)nc3cc(C)ccn23)c(C#Cc2ccc3c(C)nccc3c2)n1] |
| 14 | 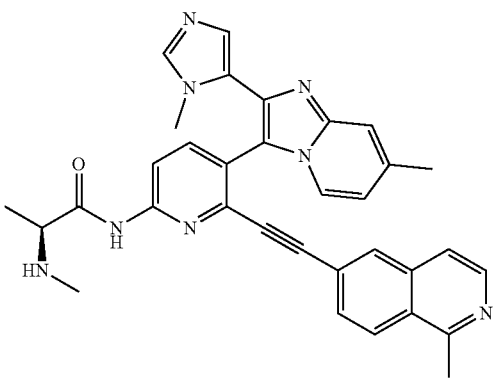 [SMILES: CN[C@@H](C)C(=O)Nc1ccc(-c2c(-c3cncn3C)nc3cc(C)ccn23)c(C#Cc2ccc3c(C)nccc3c2)n1] |
| 15 | 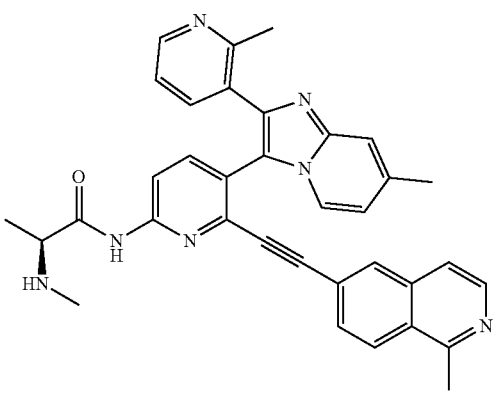 [SMILES: CN[C@@H](C)C(=O)Nc1ccc(-c2c(-c3cccnc3C)nc3cc(C)ccn23)c(C#Cc2ccc3c(C)nccc3c2)n1] |
| 16 | 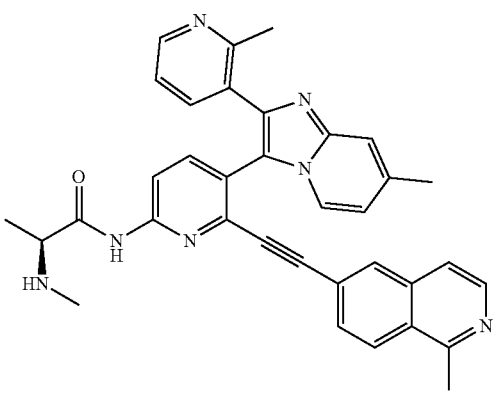 [SMILES: CN[C@@H](C)C(=O)Nc1ccc(-c2c(-c3cccnc3C)nc3cc(C)ccn23)c(C#Cc2ccc3c(C)nccc3c2)n1] |

TABLE 2-continued
17 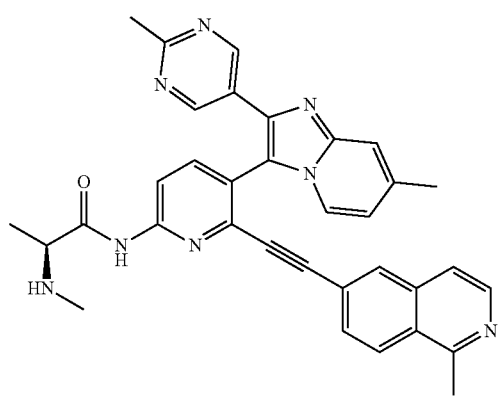 [SMILES: CN[C@@H](C)C(=O)Nc1ccc(-c2c(-c3cnc(C)nc3)nc3cc(C)ccn23)c(C#Cc2ccc3c(C)nccc3c2)n1]
18 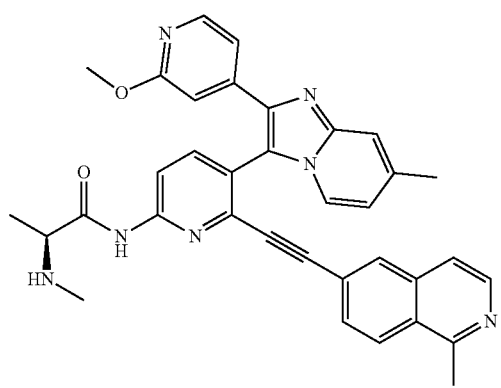 [SMILES: CN[C@@H](C)C(=O)Nc1ccc(-c2c(-c3ccnc(OC)c3)nc3cc(C)ccn23)c(C#Cc2ccc3c(C)nccc3c2)n1]
19 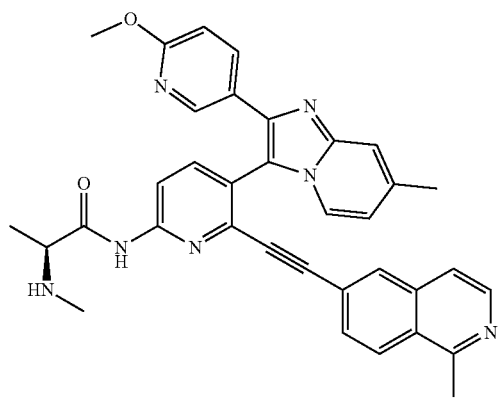 [SMILES: CN[C@@H](C)C(=O)Nc1ccc(-c2c(-c3ccc(OC)nc3)nc3cc(C)ccn23)c(C#Cc2ccc3c(C)nccc3c2)n1]
20 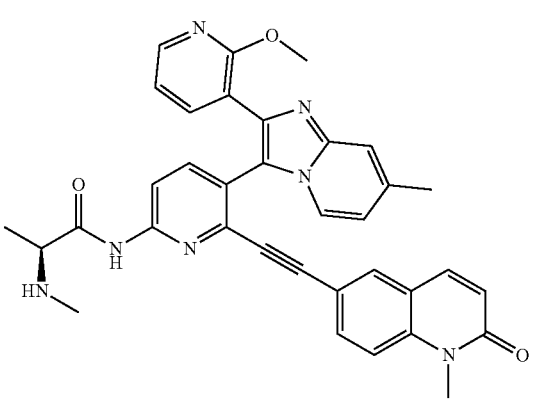 [SMILES: CN[C@@H](C)C(=O)Nc1ccc(-c2c(-c3cccnc3OC)nc3cc(C)ccn23)c(C#Cc2ccc3c(ccc(=O)n3C)c2)n1]
TABLE 2-continued
21 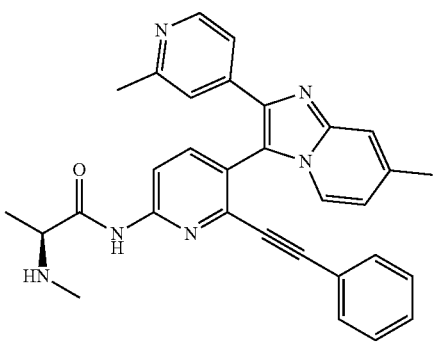 [SMILES: CN[C@@H](C)C(=O)Nc1ccc(-c2c(-c3ccnc(C)c3)nc3cc(C)ccn23)c(C#Cc2ccccc2)n1]
22 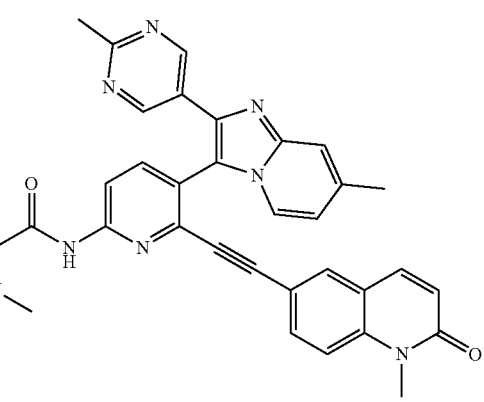
23 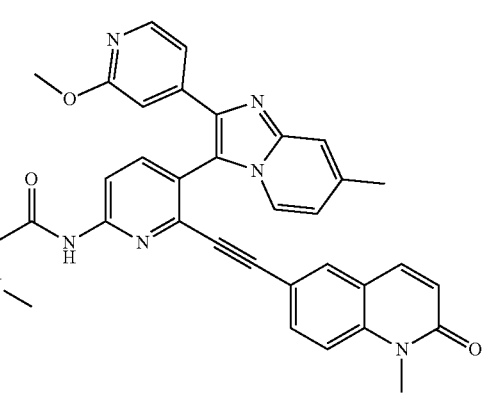
24 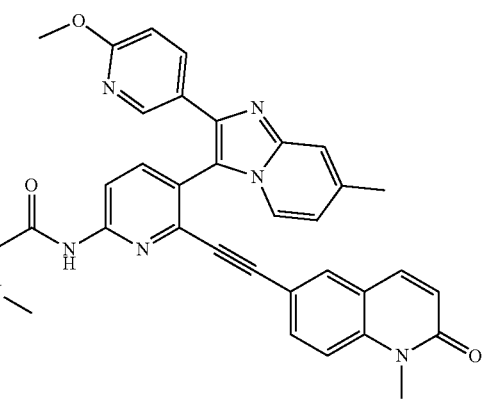

TABLE 2-continued

25

26

Example compounds 1 to 10 in Table 2 are disclosed in WO 2013/127729. Example compounds 11 to 26 in Table 2 are disclosed in WO 2016/023858.

The term "SMAC mimetic/IAP antagonist" as used herein also includes the SMAC mimetics listed above in the form of a tautomer, of a pharmaceutically acceptable salt, of a hydrate or of a solvate (including a hydrate or solvate of a pharmaceutically acceptable salt). It also includes the SMAC mimetic in all its solid, preferably crystalline, forms and in all the crystalline forms of its pharmaceutically acceptable salts, hydrates and solvates (including hydrates and solvates of pharmaceutically acceptable salts).

All SMAC mimetics listed above are known in the art with the respective synthesis and properties. All patent applications referred to above are incorporated by reference in their entirety.

In one embodiment the SMAC mimetic is LCL161 or a pharmaceutically acceptable salt thereof (A1).

In another embodiment the SMAC mimetic is compound 1 in table 2 or a pharmaceutically acceptable salt thereof (A2).

In another embodiment the SMAC mimetic is compound 2 in table 2 or a pharmaceutically acceptable salt thereof (A3).

In another embodiment the SMAC mimetic is compound 3 in table 2 or a pharmaceutically acceptable salt thereof (A4).

In another embodiment the SMAC mimetic is compound 4 in table 2 or a pharmaceutically acceptable salt thereof (A5).

In another embodiment the SMAC mimetic is compound 5 in table 2 or a pharmaceutically acceptable salt thereof (A6).

In another embodiment the SMAC mimetic is compound 6 in table 2 or a pharmaceutically acceptable salt thereof (A7).

In another embodiment the SMAC mimetic is compound 7 in table 2 or a pharmaceutically acceptable salt thereof (A8).

In another embodiment the SMAC mimetic is compound 8 in table 2 or a pharmaceutically acceptable salt thereof (A9).

In another embodiment the SMAC mimetic is compound 9 in table 2 or a pharmaceutically acceptable salt thereof (A10).

In another embodiment the SMAC mimetic is compound 10 in table 2 or a pharmaceutically acceptable salt thereof (A11).

In another embodiment the SMAC mimetic is compound 11 in table 2 or a pharmaceutically acceptable salt thereof (A12).

In another embodiment the SMAC mimetic is compound 12 in table 2 or a pharmaceutically acceptable salt thereof (A13).

In another embodiment the SMAC mimetic is compound 13 in table 2 or a pharmaceutically acceptable salt thereof (A14).

In another embodiment the SMAC mimetic is compound 14 in table 2 or a pharmaceutically acceptable salt thereof (A15).

In another embodiment the SMAC mimetic is compound 15 in table 2 or a pharmaceutically acceptable salt thereof (A16).

In another embodiment the SMAC mimetic is compound 16 in table 2 or a pharmaceutically acceptable salt thereof (A17).

In another embodiment the SMAC mimetic is compound 17 in table 2 or a pharmaceutically acceptable salt thereof (A18).

In another embodiment the SMAC mimetic is compound 18 in table 2 or a pharmaceutically acceptable salt thereof (A19).

In another embodiment the SMAC mimetic is compound 19 in table 2 or a pharmaceutically acceptable salt thereof (A20).

In another embodiment the SMAC mimetic is compound 20 in table 2 or a pharmaceutically acceptable salt thereof (A21).

In another embodiment the SMAC mimetic is compound 21 in table 2 or a pharmaceutically acceptable salt thereof (A22).

In another embodiment the SMAC mimetic is compound 22 in table 2 or a pharmaceutically acceptable salt thereof (A23).

In another embodiment the SMAC mimetic is compound 23 in table 2 or a pharmaceutically acceptable salt thereof (A24).

In another embodiment the SMAC mimetic is compound 24 in table 2 or a pharmaceutically acceptable salt thereof (A25).

In another embodiment the SMAC mimetic is compound 25 in table 2 or a pharmaceutically acceptable salt thereof (A26).

In another embodiment the SMAC mimetic is compound 26 in table 2 or a pharmaceutically acceptable salt thereof (A27).

All embodiments (A1) to (A27) are preferred embodiments of embodiment (A0) in respect of the nature of the SMAC mimetic.

In a preferred embodiment relating to the combination treatments the recombinant rhabdovirus is a recombinant vesicular stomatitis virus encoding in its genome at least one CCL21 protein or a functional variant thereof, preferably human CCL21, selected from the group comprising: (i) plasmin processed CCL21 protein, (ii) c-terminally truncated CCL21 protein, (iii) a protein comprising SEQ ID NO:2 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:2, (iv) a protein comprising SEQ ID NO:3 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:3, (v) a protein comprising SEQ ID NO:4 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:4, (vi) a protein according to any of (i)-(v) further comprising a signal peptide sequence, (vii) a protein comprising SEQ ID NO:1 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:1, or (viii) a protein comprising SEQ ID NO:5 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:5, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

In a further preferred embodiment relating to the combination treatment the recombinant rhabdovirus is a recombinant vesicular stomatitis virus encoding in its genome a vesicular stomatitis virus nucleoprotein (N), large protein (L), phosphoprotein (P), matrix protein (M), glycoprotein (G) and at least one CCL21 protein or a functional variant thereof, preferably human CCL21, wherein the CCL21 protein or functional variant thereof is selected from the group comprising: (i) plasmin processed CCL21 protein, (ii) c-terminally truncated CCL21 protein, (iii) a protein comprising SEQ ID NO:2 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:2, (iv) a protein comprising SEQ ID NO:3 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:3, (v) a protein comprising SEQ ID NO:4 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:4, (vi) a protein according to any of (i)-(v) further comprising a signal peptide sequence, (vii) a protein comprising SEQ ID NO:1 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:1, or (viii) a protein comprising SEQ ID NO:5 or having at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:5, wherein the gene coding for the glycoprotein G of the vesicular stomatitis virus is replaced by the gene coding for the glycoprotein GP of lymphocyte choriomeningitis virus (LCMV), and/or the glycoprotein G is replaced by the glycoprotein GP of LCMV, and wherein the nucleoprotein (N) comprises an amino acid as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, the phosphoprotein (P) comprises an amino acid as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, the large protein (L) comprises an amino acid as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and the matrix protein (M) comprises an amino acid as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

In a more preferred embodiment relating to the combination treatments the recombinant rhabdovirus is a recombinant vesicular stomatitis virus encoding in its genome at least one CCL21 protein or a functional variant thereof, preferably human CCL21, wherein the CCL21 protein or functional variant thereof comprises SEQ ID NO:5 or has at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO:5, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

While the combination of recombinant rhabdovirus of the invention and in particular the vesicular stomatitis virus of the invention together with PD-1 inhibitors or SMACm/IAP antagonists was exceptionally effective in the treatment of cancers it was found by the inventors that the combination of a vesicular stomatitis virus, not encoding for an additional cargo, i.e. not encoding for a CCL21 protein was also effective when combined with a PD-1 pathway inhibitor or a SMACm/IAP antagonist. In particular, the combination treatment of a VSV-GP (vesicular stomatitis virus with the glycoprotein of LCMV) with a PD-1 pathway inhibitor or SMACm/IAP antagonist, both as described herein, was efficient for the treatment of cancer, preferably solid cancers. Therefore, also provided herein is a combination comprising a VSV-GP not encoding for a CCL21 protein and a PD-1 pathway inhibitor, preferably an antagonistic antibody which is directed against PD-1 or PD-L1 or a SMACm/IAP antagonist. Further provided is the use of such a combination for the treatment of cancers as described herein. Further provided is a combination treatment comprising the use of a VSV-GP not encoding for a CCL21 protein and a PD-1 pathway inhibitor or a SMACm/IAP antagonist.

Related to the combination treatment of VSV-GP not encoding for a CCL21 protein, it is preferred that the recombinant rhabdovirus is a recombinant vesicular stomatitis virus, wherein the gene coding for the glycoprotein G of the recombinant vesicular stomatitis virus is replaced by the gene coding for the glycoprotein GP of lymphocyte choriomeningitis virus (LCMV), and/or the glycoprotein G is replaced by the glycoprotein GP of LCMV.

Further related to the combination treatment of a VSV-GP not encoding for a CCL21 protein, it is preferred that the recombinant rhabdovirus is a recombinant vesicular stomatitis virus encoding in its genome a vesicular stomatitis virus nucleoprotein (N), large protein (L), phosphoprotein (P), matrix protein (M), glycoprotein (G), wherein the gene coding for the glycoprotein G of the vesicular stomatitis virus is replaced by the gene coding for the glycoprotein GP of lymphocyte choriomeningitis virus (LCMV), and/or the glycoprotein G is replaced by the glycoprotein GP of LCMV, and wherein the nucleoprotein (N) comprises an amino acid as set forth in SEQ ID NO:7 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:7, the phosphoprotein (P) comprises an amino acid as set forth in SEQ ID NO:8 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:8, the large protein (L) comprises an amino acid as set forth in SEQ ID NO:9 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:9, and the matrix protein (M) comprises an amino acid as set forth in SEQ ID NO:10 or a functional variant at least 80%, 81%, 82%, 83%, 84%, 85%, 86%, 87%, 88%, 89%, 90%, 91%, 92%, 93%, 94%, 95%, 96%, 97%, 98% or 99% identical to SEQ ID NO:10.

Virus Generation, Production and Virus Producing Cell

The invention also provides a virus producing cell, characterized in that the cell produces a recombinant rhabdovirus or recombinant vesicular stomatitis virus according to the invention.

The cell may be of any origin and may be present as isolated cell or as a cell comprised in a cell population. It is preferred that the cell producing a recombinant rhabdovirus or recombinant vesicular stomatitis virus is a mammalian cell. In a more preferred embodiment, the virus producing cell of the invention is characterized in that the mammalian cell is a multipotent adult progenitor cell (MAPC), a neural stem cell (NSC), a mesenchymal stem cell (MSC), a HeLa cell, a HEK cell, any HEK293 cell (e.g. HEK293F or HEK293T), a Chinese hamster ovary cell (CHO), a baby hamster kidney (BHK) cell or a Vero cell or a bone marrow derived tumor infiltrating cell (BM-TIC).

Alternatively, the virus producing cell may be a human cell, monkey cell, mouse cell or hamster cell. The skilled person is aware of methods suitable for use in testing whether a given cell produces a virus and, thus, whether a particular cell falls within the scope of this invention. In this respect, the amount of virus produced by the cell of the invention is not particularly limited. Preferred viral titers are ≥1×10$^7$ TCID50/ml or ≥1×10$^8$ genome copies/ml in the crude supernatants of the given cell culture after infection without further downstream processing.

In a particular embodiment, the virus producing cell of the invention is characterized in that the cell comprises one or more expression cassettes for the expression of at least one of the genes selected from the group consisting of genes n, l, p and m coding for proteins N, L, P and M of the VSV and a gene gp coding for LCMV-GP, Dandenong-GP or Mopeia-GP glycoprotein.

Virus producing cells in the meaning of the invention include classical packaging cells for the production of recombinant rhabdovirus from non-replicable vectors as well as producer cells for the production of recombinant rhabdovirus from vectors capable of reproduction. Packaging cells usually comprise one or more plasmids for the expression of essential genes which lack in the respective vector to be packaged and/or are necessary for the production of virus. Such cells are known to the skilled person who can select appropriate cell lines suitable for the desired purpose.

Recombinant rhabdovirus of the invention can be produced according to methods known to the skilled artisan and include without limitation (1) using cDNAs transfected into a cell or (2) a combination of cDNAs transfected into a helper cell, or (3) cDNAs transfected into a cell, which is further infected with a helper/minivirus providing in trans the remaining components or activities needed to produce either an infectious or non-infectious recombinant rhabdovirus. Using any of these methods (e.g., helper/minivirus, helper cell line, or cDNA transfection only), the minimum components required are a DNA molecule containing the cis-acting signals for (1) encapsidation of the genomic (or antigenomic) RNA by the Rhabdovirus N protein, P protein and L protein and (2) replication of a genomic or antigenomic (replicative intermediate) RNA equivalent.

A replicating element or replicon is a strand of RNA minimally containing at the 5' and 3' ends the leader sequence and the trailer sequence of a rhabdovirus. In the genomic sense, the leader is at the 3' end and the trailer is at the 5' end. Any RNA-placed between these two replication signals will in turn be replicated. The leader and trailer regions further must contain the minimal cis-acting elements for purposes of encapsidation by the N protein and for polymerase binding which are necessary to initiate transcription and replication. For preparing recombinant rhabdovirus a minivirus containing the G gene would also contain a leader region, a trailer region and a G gene with the appropriate initiation and termination signals for producing a G protein mRNA. If the minivirus further comprises an M gene, the appropriate initiation and termination signals for producing the M protein mRNA must also present.

For any gene contained within the recombinant rhabdovirus genome, the gene would be flanked by the appropriate transcription initiation and termination signals which will allow expression of those genes and production of the protein products (Schnell et al., Journal of Virology, p. 2318-2323, 1996). To produce "non-infectious" recombinant rhabdovirus, the recombinant rhabdovirus must have the minimal replicon elements and the N, P, and L proteins and it must contain the M gene. This produces virus particles that are budded from the cell, but are non-infectious particles. To produce "infectious" particles, the virus particles must additionally comprise proteins that can mediate virus particle binding and fusion, such as through the use of an attachment protein or receptor ligand. The native receptor ligand of rhabdoviruses is the G protein.

Any cell that would permit assembly of the recombinant rhabdovirus can be used. One method to prepare infectious virus particles comprises an appropriate cell line infected with a plasmid encoding for a T7 RNA polymerase or other suitable bacteriophage polymerase such as the T3 or SP6 polymerases. The cells may then be transfected with individual cDNA containing the genes encoding the G, N, P, L and M rhabdovirus proteins. These cDNAs will provide the proteins for building a recombinant rhabdovirus particle. Cells can be transfected by any method known in the art.

Also transfected into the cell line is a "polycistronic cDNA" containing the rhabdovirus genomic RNA equivalent. If the infectious, recombinant rhabdovirus particle is intended to be lytic in an infected cell, then the genes encoding for the N, P, M and L proteins must be present as well as any heterologous nucleic acid segment. If the infectious, recombinant rhabdovirus particle is not intended to be lytic, then the gene encoding the M protein is not included in the polycistronic DNA. By "polycistronic cDNA" it is meant a cDNA comprising at least transcription units containing the genes which encode the N, P and L proteins. The recombinant rhabdovirus polycistronic DNA may also contain a gene encoding a protein variant or polypeptide fragment thereof, or a therapeutic nucleic acid or protein.

Alternatively, any protein to be initially associated with the viral particle first produced or fragment thereof may be supplied in trans.

Also contemplated is a polycistronic cDNA comprising a gene encoding for CCL21. The polycistronic cDNA contemplated may contain a gene encoding a protein variant, a gene encoding a reporter, a therapeutic nucleic acid, and/or either the N—P-L genes or the N—P-L-M genes. The first step in generating a recombinant rhabdovirus is expression of an RNA that is a genomic or antigenomic equivalent from a cDNA. Then that RNA is packaged by the N protein and then replicated by the P/L proteins. The recombinant virus thus produced can be recovered. If the G protein is absent from the recombinant RNA genome, then it is typically supplied in trans. If both the G and the M proteins are absent, then both are supplied in trans. For preparing “non-infectious rhabdovirus” particles, the procedure may be the same as above, except that the polycistronic cDNA transfected into the cells would contain the N, P and L genes of the rhabdovirus only. The polycistronic cDNA of non-infectious rhabdovirus particles may additionally contain a gene encoding a protein.

Transfected cells are usually incubated for at least 24 hr at the desired temperature, usually about 37 degrees. For non-infectious virus particles, the supernatant is collected and the virus particles isolated. For infectious virus particles, the supernatant containing virus is harvested and transferred to fresh cells. The fresh cells are incubated for approximately 48 hours, and the supernatant is collected.

Other features and advantages of the present invention will become apparent from the following more detailed Examples which illustrate, by way of example, the principles of the invention.

EXAMPLES

Example 1

Induction of Immune Infiltration/Activation and Immune Checkpoint Expression in VSV-GP Infected Tumors Expression Analysis/NanoString (FIG. 1)

To better understand the impact of therapeutic interventions with the VSV-GP Platform immune cell infiltration (T-cells: CD3 epsilon, CD4 and CD8), activation (CD69, Granzyme B (GzmB) and Perforin (Prf1)) as well as immune checkpoint (PD-L1 (CD274), PD-1 (Pdcd1), Ctla-4, Tigit and Lag3) expression was analyzed in control or VSV-GP infected tumors. To this end C57BL/6 mice with established LLC1-IFNARKO (LLC1 tumor cells deleted for the interferon alpha receptor) tumors were used as controls or treated with a single i.v. injection of $1\times10^8$ $TCID_{50}$ of VSV-GP. Seven days post treatment tumors were resected; whole RNA was extracted and analyzed using the “Pan Cancer Immune Profiling Panel” from NanoString according to the manufacturer’s instructions. As depicted in FIG. 1 VSV-GP treatment resulted in a strong upregulation of the expression of the analyzed genes, including the PD-L1 and PD-1 genes.

Example 2

Efficacy: VSV-GP Combo with Anti-PD-1

Tumor Growth (FIG. 2A-D)

Building on the clinical success of PD-1 resp. PD-L1 blocking antibodies in cancer patients and our own data (see FIG. 1) illustrating that treatment with the VSV-GP platform resulted in the activation of tumor infiltrating T-cells, going hand-in-hand with the upregulation of immune checkpoints, such as PD-1 and PD-L1 the therapeutic potential of combining VSV-GP derived therapeutics with a PD-1 blocking antibody was analyzed using the CT26.CL25-IFNARKO tumor model (CT26.CL25 tumor cells deleted for the interferon alpha receptor).

The engraftment rates of s.c. injected CT26C125 IFNAR−/− tumor cells was 100% (50/50 mice). At day 8 (day of virus application), median tumor size was 0.05 $cm^3$. Tumor growth was followed over a 60 day interval. Mock (=untreated) controls displayed 10% spontaneous remissions (1/10) and one tumor grew out much slower. Mice treated with VSV-GP i.v. alone, 30% (3/10 mice) complete remissions were observed. PD-1 treatment alone starting at day 11 post engraftment had no effect on tumor growth. Combination of VSV-GP with anti-PD-1 resulted in high tumor remission rates. Complete remissions were seen in 70% (7/10 mice) when anti-PD-1 was applied after VSV-GP treatment. Mice remained tumor-free for at least 60 days. Overall, high survival rates were achieved in the combination groups (not shown).

Example 3

Memory Formation: VSV-GP & VSV-GP/Anti-PD-1 Combo

Tumor Growth/Rechallenge (FIG. 3A-C)

Cured mice from VSV-GP/anti-PD-1 combination experiments are protected from rechallenge. Mice from VSV-GP/anti-PD-1 combination group (n=7) or VSV-GP alone (low dose, n=3) group were rechallenged. Briefly, CT26C125 IFNAR−/− cells were injected s.c. into the left flank of the mice and tumor growth was monitored over time. As positive control, age- and sex matched naïve mice (n=10) were engrafted with CT26C125 IFNAR−/− s.c. and tumors grew out consistently with one spontaneous remission as observed before. No tumor outgrowth was observed in VSV-GP/anti-PD-1 combination group (n=7) or VSV-GP alone (low dose, n=3) group, indicating that cured mice developed a certain immunological memory.

Example 4

Selection of CCL21 Cargo and VSV-GP Induced Chemokine Expression in Tumors

NanoString® Expression Analysis (FIG. 4)

The impact of therapeutic interventions with the VSV-GP platform in preclinical tumor models was analyzed by measuring the expression of multiple chemokines (FIG. 4). CCL5, CXCL9, CXCL10 and other chemokine expression were strongly upregulated in LLC1-IFNARKO tumors 3 resp. 7 days after a single i.v. treatment with $1\times10^8$ $TCID_{50}$ of VSV-GP. On the other hand expression of CCR7 ligands CCL19 and CCL21 were not upregulated by VSV-GP infection.

Example 5

Generation of VSV-CCL21 Recombinants

Viral Rescue (FIG. 5)

Building on the findings described in Example 4 the genome of the oncolytic virus VSV-GP was engineered to encode for the CCL21 gene (see FIG. 5) to locally express the CCL21 chemokine at the tumor site during viral replication and to fill the “immuno-therapeutic gap” of VSV-GP (VSV-GP was not able to upregulate the CCR7 ligands CCL19 and CCL21) and further improve immune cell infiltration as well as therapeutic efficacy of the oncolytic virus VSV-GP.

Replication competent VSV-GP-CCL21 virus variants were generated by means of reverse genetics (cloning the gene of interest (GOI), virus rescue and repeated plaque purification) from bacterial plasmids that contain the cDNA for the complete viral genome of VSV-GP and versions of murine or human CCL21. pVSV-GP-CCL21 plasmids were based on the plasmid pVSV-XN1 (Schnell et al.]which contains the complete cDNA genome of VSV Indiana serotype under the control of the T7 promoter. In order to generate pVSV-GP-CCL21 variants, the whole sequence for the VSV G envelope protein was substituted by the codon optimized sequence of GP envelope protein from Lymphocytic choriomeningitis virus (LCMV, WE-HPI strain). Additionally, a synthetic nucleic acid coding for a CCL21 gene was inserted between the glycoprotein GP and the viral polymerase L by Gibson assembly. Transcription of the CCL21 gene in the context of viral infection is ensured by an extra VSV start signal sequence at the 3' end and of an additional stop signal sequence at the 5' end of the CCL21 open reading frame (FIG. 5A).

Infectious viruses were recovered (or rescued) from the plasmid cDNAs by transfection of HEK293T or any other VSV permissive cell line by standard transfection methods (e.g. $CaPO_4$ precipitation, liposomal DNA delivery). Briefly, HEK293T cells were transfected with pSF-CAG-amp-based expression plasmids encoding the VSV proteins N, P, and L as well as a codon-optimized T7-polymerase. Additionally, the plasmid coding the viral genomic cDNA of VSV-GP, VSV-GP-CCL21 or a variant thereof was co-transfected (FIG. 5B). In a first step of the rescue process, the T7 polymerase transcribes the virus RNA genome from the plasmid coded virus cDNA. In a second step, VSV-L and —P proteins, which are exogenously expressed from the co-transfected plasmids, further amplify the viral RNA genomes. The viral RNA genomes are co-transcriptionally encapsidated by the VSV-N protein. Additionally, the P/L polymerase complex allows transcription of the full set of viral gene products N, P, M, GP and L as well as the inserted CCL21 variants. The viral RNA genomes are subsequently packaged into infectious VSV particles containing the ribonucleoprotein, the matrix protein and the viral envelope GP. Virus particles are released from the cells by budding.

Rescued viruses were initially passaged in permissive cell lines such as HEK293T, BHK21Cl.13 or VERO. Several rounds of plaque purification were performed before generation of a virus seed stock by standard methods. Briefly, HEK293T, BHK2101.13 or VERO cells were infected with serial ten-fold dilutions of the rescued pre-seeds. After approximately two hours, cell monolayers were washed twice and overlaid with media containing 0.8% of low melt agarose. 24 h to 48 h post infection, plaques were picked and virus was used for an additional round of plaque-purification or virus seed stocks were generated.

Example 5.1

Validation of Viral Fitness In Vitro
$TCID_{50}$ (FIG. 19A-C)
One day before infection, Vero, BHK21 and HEK293 cells were seeded into 6-well plates. The corresponding culture media were: (a) Vero cells: DMEM (Gibco, #31966-021)+5% heat-inactivated FBS (Gibco, #10500-064), (b) BHK21 cells: GMEM (Life Technologies, #21710-082/025)+10% heat-inactivated FBS (Gibco, #10500-064)+5% TPB Tryptose Phosphate Broth (Life Technologies, #18050-039), (c) HEK293 cells: Freestyle™ 293 Expression Medium (ThermoFisher Scientific, #12338018).

On the day of infection, all cell lines had a confluency of 60-70%. One well per cell line was counted (Countess™ cell counter, Invitrogen) before infecting the other wells with 0.005 MOI of one of the virus constructs VSV-GP (GP), VSV-GP-huCCL21 (21) or VSV-GP-huCCL21(1-79) (21 k).

Culture supernatants (3 mL total volume) were harvested 0 h, 24 h, or 48 h post infection to determine viral replication competence by measuring $TCID_{50}/mL$.

$TCID_{50}$ (Median Tissue Culture Infectious Dose) was determined on 96-well plates of VERO cells that were seeded one day before infection. Of all supernatants, twenty-two serial half-logarithmic dilutions were prepared (ranging from 1E-1.0 to 1E-11.5) and titrated in quadruplicates. Six days after infection, cytopathic effect (CPE) was read out by microscopic inspection of the plates.

$TCID_{50}/mL$ was calculated according to the Spearman-Karber formula $M=x+d\ [0.5-(1/n)\ (r)]$ with x: positive exponent of highest dilution tested; d=spacing between dilutions; n=wells per dilution; r=sum of the number of negative responses.

Example 5.2

Figure 12:
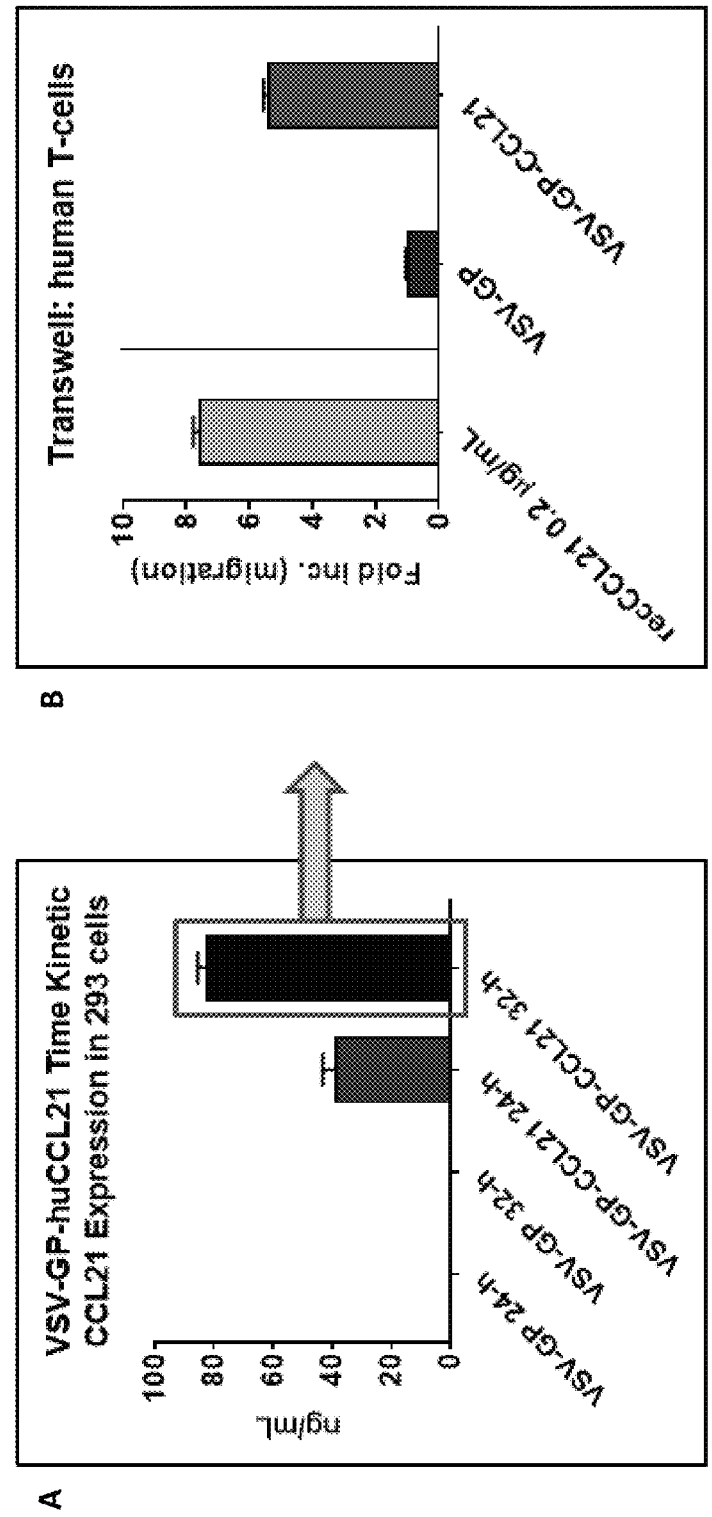
FIG. 12A-B: (A) Analysis of human CCL21 in the supernatants of HEK293 cells infected with VSV-GP-huCCL21 (VSV-GP encoding full length human CCL21). (B) Functional analysis of human T-cell migration using a Transwell Set-up and recombinant human CCL21 or supernatants from VSV-GP resp. VSV-GP-huCCL21 infected HEK293 cells.
Figure 18:
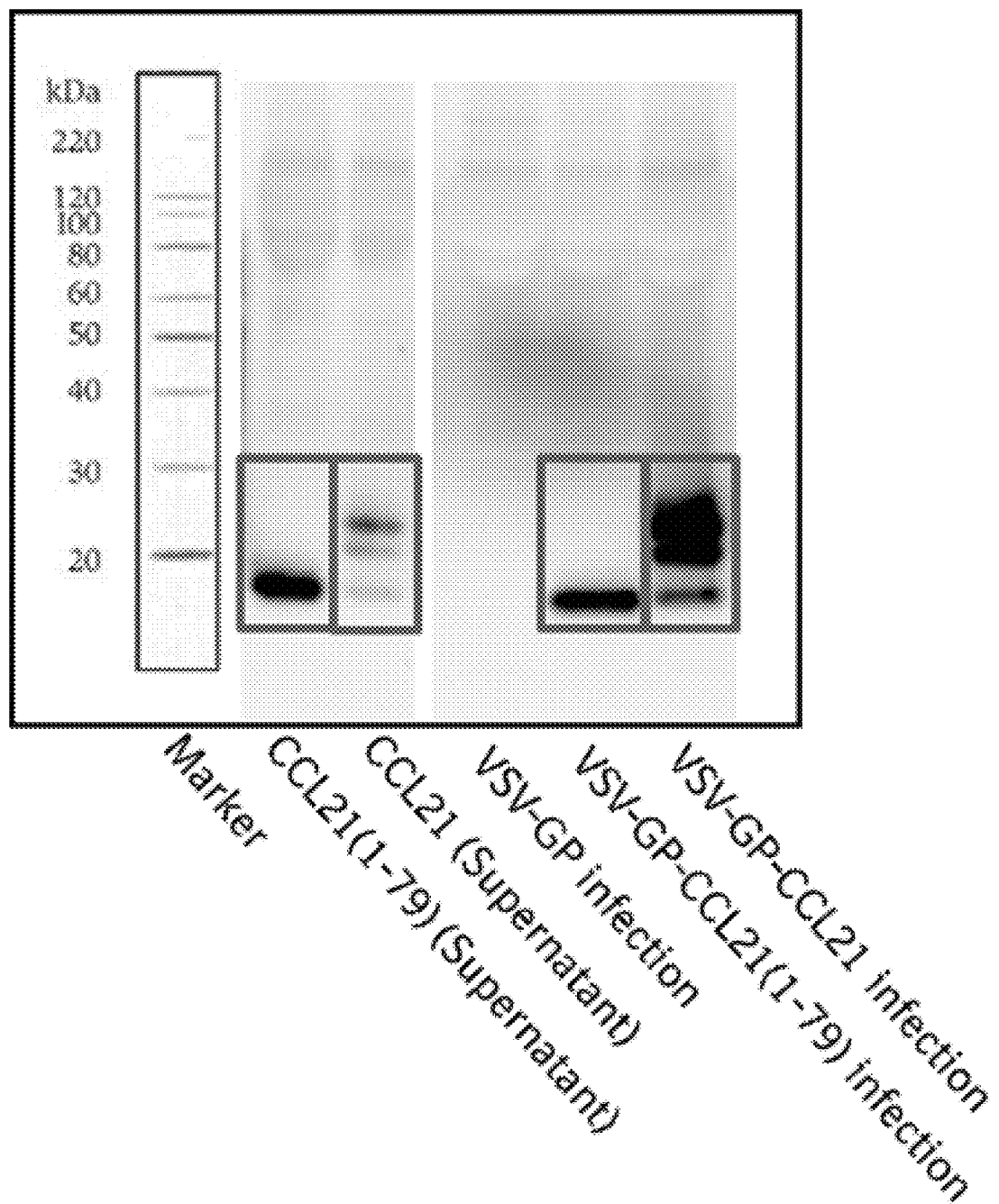
FIG. 18: Western Blot (WB) analysis of CCL21 in supernatants from plasmid transfected HEK293 cells expressing the indicated, c-terminally truncated resp. full-length version of CCL21 or supernatants from VSV-GP resp. VSV-GP-huCCL21(1-79) or VSV-GP-huCCL21infected HEK293 cells.

Cargo Expression In Vitro
ELISA/Western Blot (FIG. 6A-B & FIG. 12A-B & FIG. 18)
To confirm and quantitate expression of the viral CCL21 cargos (transgenes) as well as to better characterize different CCL21 variants CCL21 specific ELISAs as well as western blot analysis were conducted. As depicted FIG. 6A and FIG. 12A supernatants from VSV-GP-muCCL21 (FIG. 6A; VSV-GP expressing the full length murine CCL21) infected HEK293 cells or VSV-GP-huCCL21 (FIG. 12A; VSV-GP expressing the full length human CCL21) respectively were analyzed at different time points following viral infection using mouse resp. human specific ELISAs. In addition human CCL21 variants were characterized, namely the full length human CCL21 and the c-terminally truncated version resembling the first 79 amino acids (without the signal sequence) of human CCL21=CCL21(1-79) using a human CCL21 specific western blot. As depicted in FIG. 18 (from the left) supernatants from plasmid transfected HEK293 cells, which encode for the CCL21(1-79) or full length CCL21 proteins as well as supernatants from HEK293 cells infected with the indicated viruses were analyzed. The chemokine variants were expressed well in both systems (plasmid and virus). While the full-length CCL21 samples contained multiple CCL21 species resp. break-down/cleavage products the CCL21(1-79) protein presented as a clean single band.

Example 5.3

Figure 15:
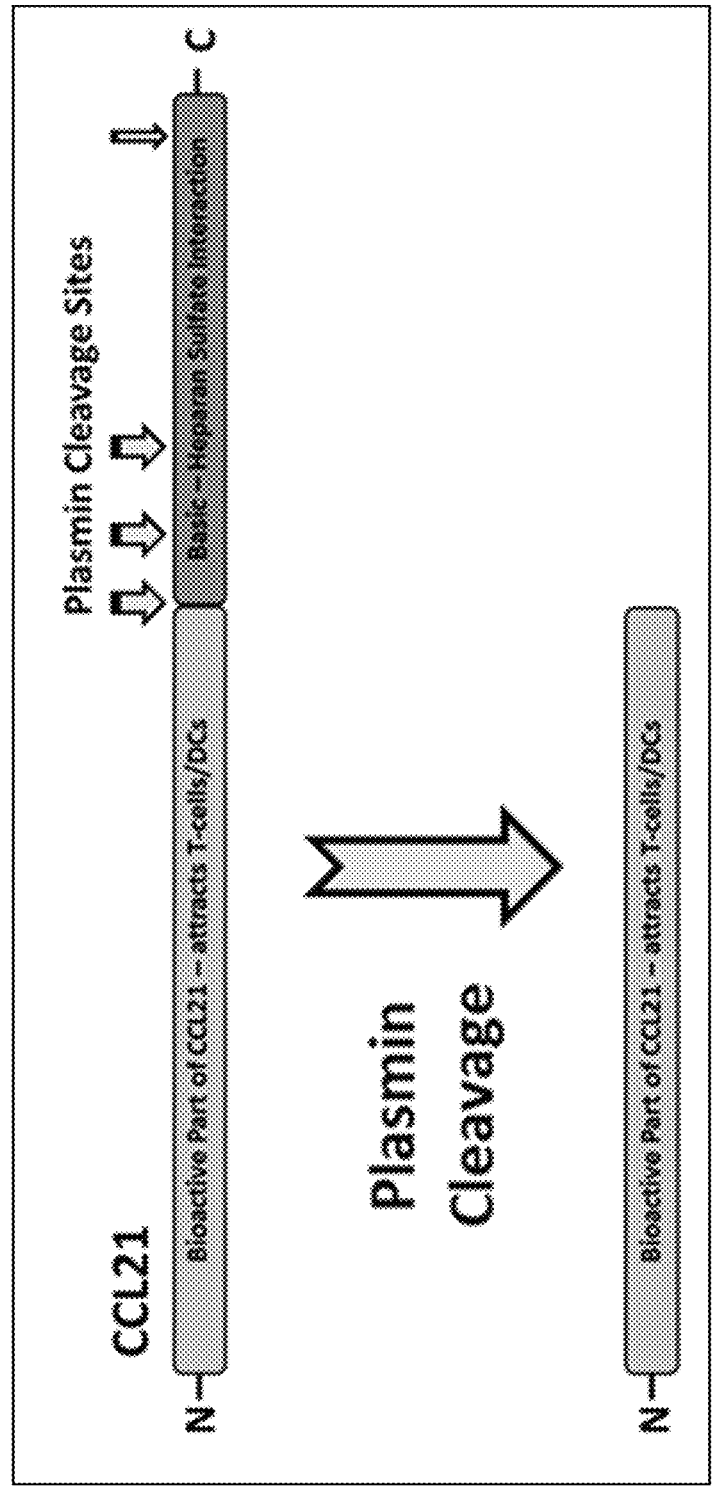
FIG. 15: Cartoon illustrating CCL21 processing by plasmin to generate the short and diffusible n-terminal fragment.
Figure 16:
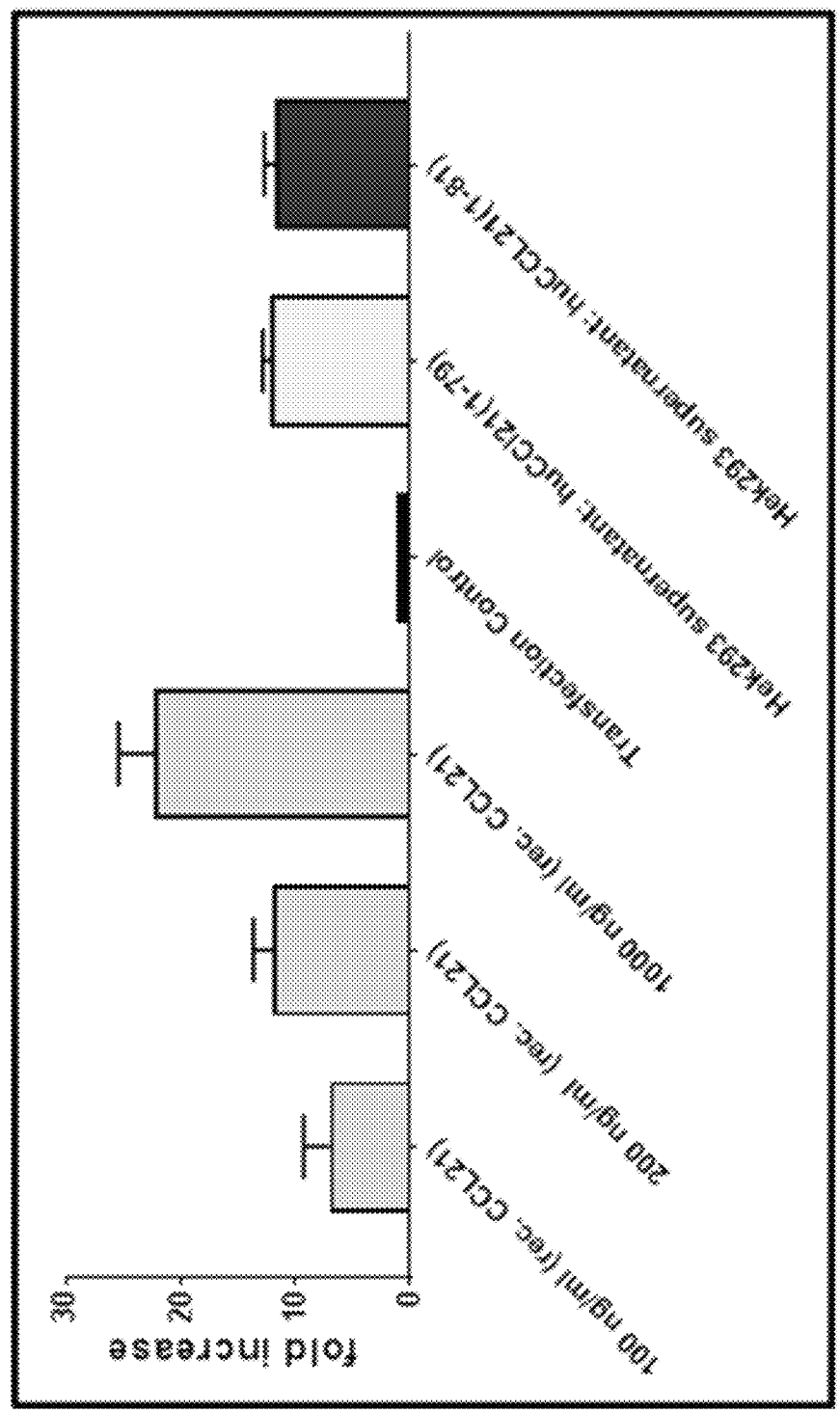
FIG. 16: Functional analysis of human T-cell migration using a Transwell set-up and recombinant human CCL21 (rec. CCL21) or supernatants from plasmid transfected HEK293 cells expressing the indicated, c-terminally truncated versions of CCL21.
Figure 17:
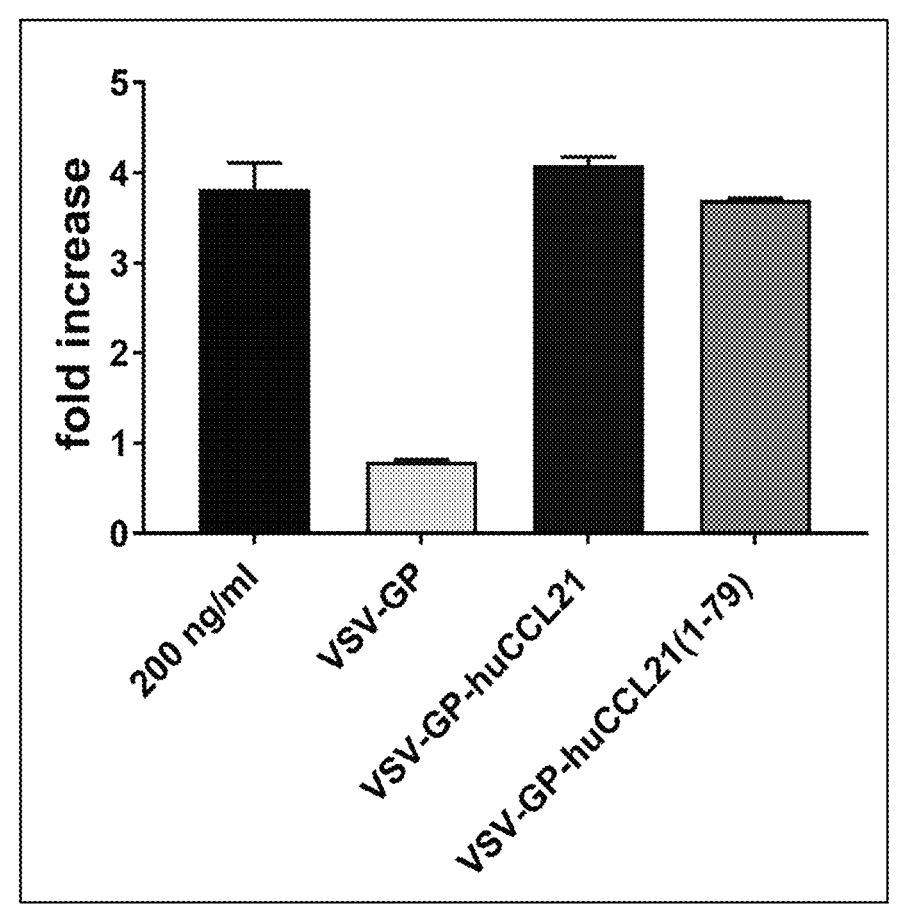

Cargo Activity In Vitro
Transwell (T-Cells/DCs) (FIGS. 6A & 12A & 16 & 17)
To confirm and further characterize the biological functionality of the viral CCL21 cargos (transgenes) their ability to attract T-cells or monocyte derived dendritic cells (moDCs) in a Transwell Migration assay was analyzed. To this end the mouse and human CCL21 containing supernatants resp. described in Example 5.2 (FIGS. 6A & 12A), migration medium only (background control), recombinant CCL21 (positive control) or matched supernatants from VSV-GP infected HEK293 cells (VSV-GP background control) were added to the bottom well of the Transwell Migration assay set-up and CD3/28 stimulated mouse (FIG. 6; right site) or human (FIG. 12; right site) T-cells added to the upper chamber (Transwell Insert). Following incubation cells in the bottom well were quantitated using Promega® CellTiter-Glo® Cell Viability Assay. Results are depicted as "fold increase" relative to the migration medium only control. Further experiments included the short cargo version of CCL21, CCL21(1-79) (aa 1-79 of human CCL21) and the shortest, naturally occurring CCL21 fragment resulting from plasmin mediated processing; CCL21(1-81) (aa 1-81 of human CCL21) using above described assays (see FIG. 15). For this purpose supernatants from expression plasmid transfected HEK293 cells were generated and analyzed (see FIG. 16). In a last step, supernatants were compared from VSV-GP, VSV-GP-huCCL21 (full-length) and VSV-GP-huCCL21(1-79) infected HEK293 cells by using the Transwell Migration assays described above and moDCs as responding cells. In this assay both full-length human CCL21 and CCL21(1-79) resulted in comparable moDC migration (see FIG. 17).

Example 5.4

Figure 13:
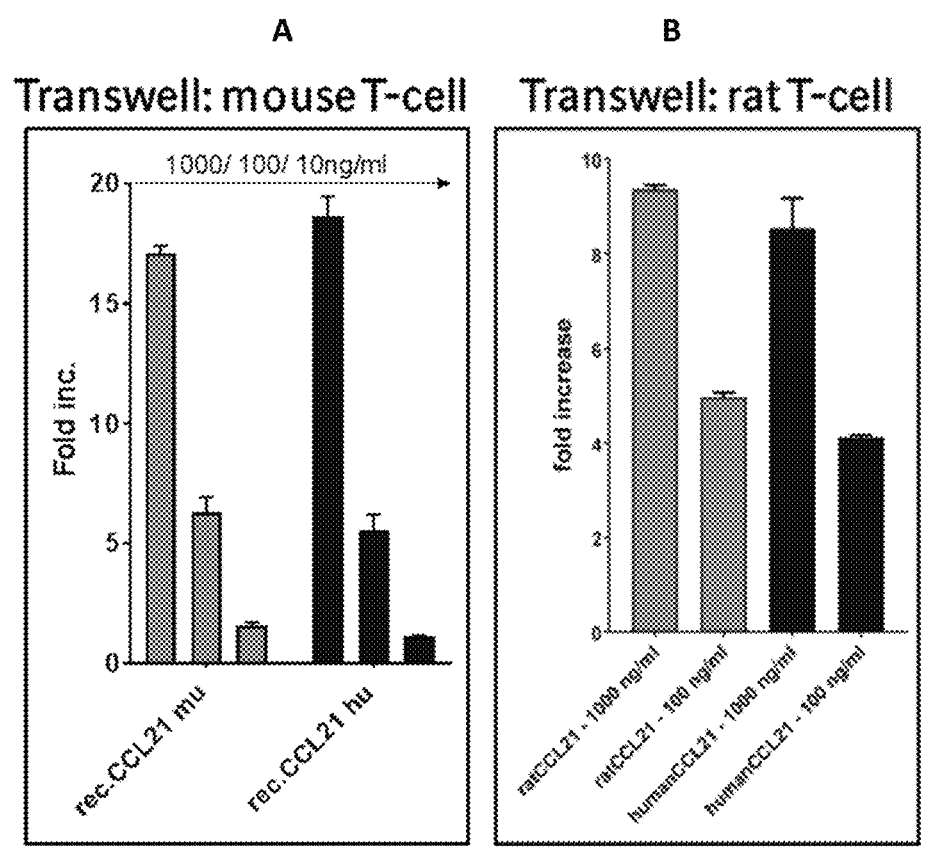
FIG. 13A-B: Functional analysis of mouse (A, left panel) and rat (B right panel) T-cell migration using a Transwell Set-up and recombinant mouse vs. human CCL21 or rat vs. human CCL21 respectively, to test for species cross reactivity.

Species Cross Reactivity (Human to Mouse & Rat) In Vitro
Transwell (T-Cells) (FIG. 13)
To confirm cross-species reactivity of the human CCL21 to the mouse and rat CCL21 receptor (CCR7) above-described Transwell Migration assay was used with mouse (left) or rat (right) T-cells as responders (see FIG. 13). Migration assays were performed using human vs. mouse (left) and human vs. rat (right) recombinant chemokines at the indicated concentrations (bottom well). In conclusion, human CCL21 was as active in the mouse and rat system as the corresponding mouse and rat chemokines respectively, indicating that the human molecule can be tested in preclinical rodent (mouse/rat) models.

Example 6

Figure 10:
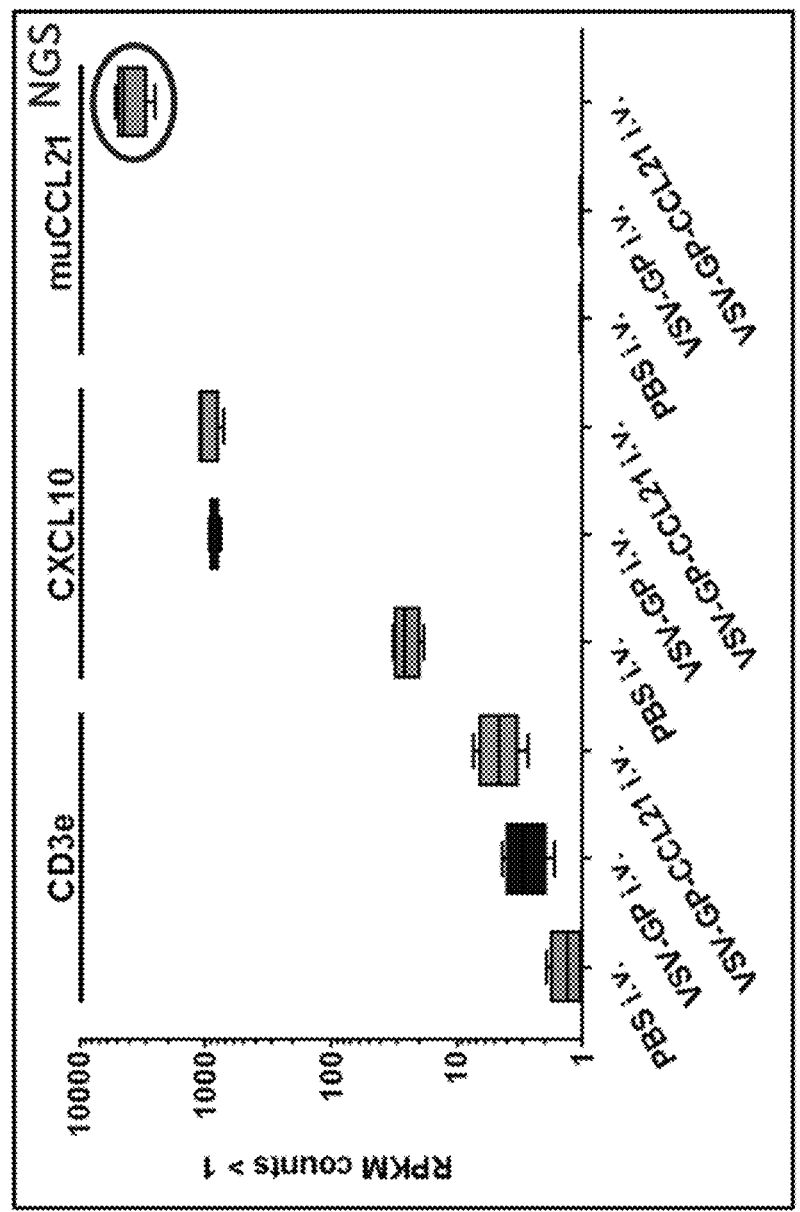
FIG. 10: Expression Analysis of LLC1-IFNARKO Tumors (whole RNA) from control, VSV-GP or VSV-GPmuCCL21 treated mice for CD3epsilon, CXCL10 and the codon-optimized sequence of murine CCL21 encoded by VSV-GP-muCCL21.

Cargo CCL21 Expression In Vivo
RNAseq (FIG. 10)
Virally encoded CCL21 expression was analyzed/confirmed in rodent tumors in control or VSV-GP resp. VSV-GP-muCCL21 infected tumors. To this end C57BL/6 mice with established LLC1-IFNARKO tumors were used as controls or treated with a single i.v. injection of $1 \times 10^8$ TCID$_{50}$ of VSV-GP or VSV-GP-muCCL21. Seven days post treatment tumors were resected; whole RNA was extracted and analyzed using RNAseq. CD3epsilon and CXCL10 were used as comparators. Virally encoded CCL21 was specifically detected using the codon optimized DNA sequence as a readout (see FIG. 10).

Example 6.1

Figure 11:
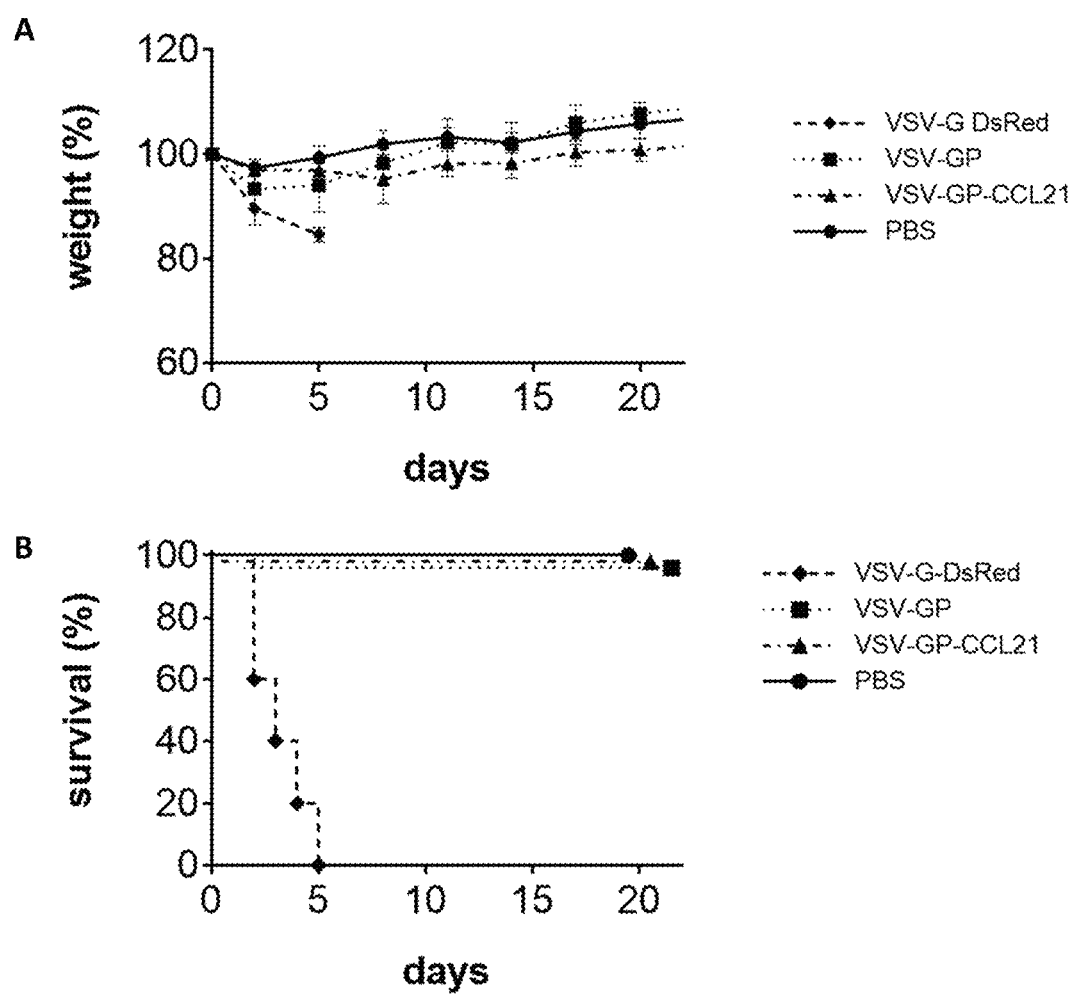
FIG. 11A-B: Assessment of neurotoxicity induced by intra-cerebral injection of VSV-G DsRed (neurotoxic wt VSV), VSV-GP, VSV-GP-muCCL21 or PBS. Panel (A) shows percentage weight gain/loss in mice over time after respective injections. Panel (B) shows percentage survival of mice over time after respective injections.

Lack of Neurotoxicity of VSV-GP and VSV-GP-CCL21
Survival (FIG. 11)
Wild type VSV infections can cause neurological symptoms when the virus gets access to the brain. These neurological complications include a severe encephalitis that can lead to death of the infected subject. The advantage of using a chimeric VSV-GP is that neuronal infection has been shown to be nearly completely absent rendering the VSV-backbone a safe oncolytic agent. The reason for the attenuated phenotype is thought to be due to an altered virus tropism facilitated via the viral envelope glycoprotein. Although neuronal infection and spread of VSV-GP in the brain is not seen, it is not clear if viral gene expression in other celltypes such as glia cells or astorcytes e.g. is completely lacking. Accidental expression of the CCL21 transgene by VSV GP might attract immune cells causing adverse effects within the brain therefore a neurotoxicity assessment of VSV-GP-muCCL21 was done.

Swiss CD-1 mice received a single intracranial injection of 3 µl containing $1 \times 10^6$ TCID$_{50}$ via stereotactic injection into the right striatum. PBS was administered i.c. in the control group. Animals were monitored daily for signs of neurotoxicity and general well-being. Mouse survival of PBS (dots), VSV-G DsRed (diamonds), VSV-GP (squares), and VSV-GP muCCL21 experimental groups were plotted as Kaplan-Meier curves (FIG. 11B). Kaplan-Meier analysis indicates that none of the tested virus variants showed neurotoxicity in mice. Only the VSV-G DsRed control group, which contained the wildtype VSV glycoprotein at the virus surface showed an increased weight loss (FIG. 11A), developed neurological signs leading to euthanasia within the first week after i.c. infection.

Example 6.2

Figure 14:
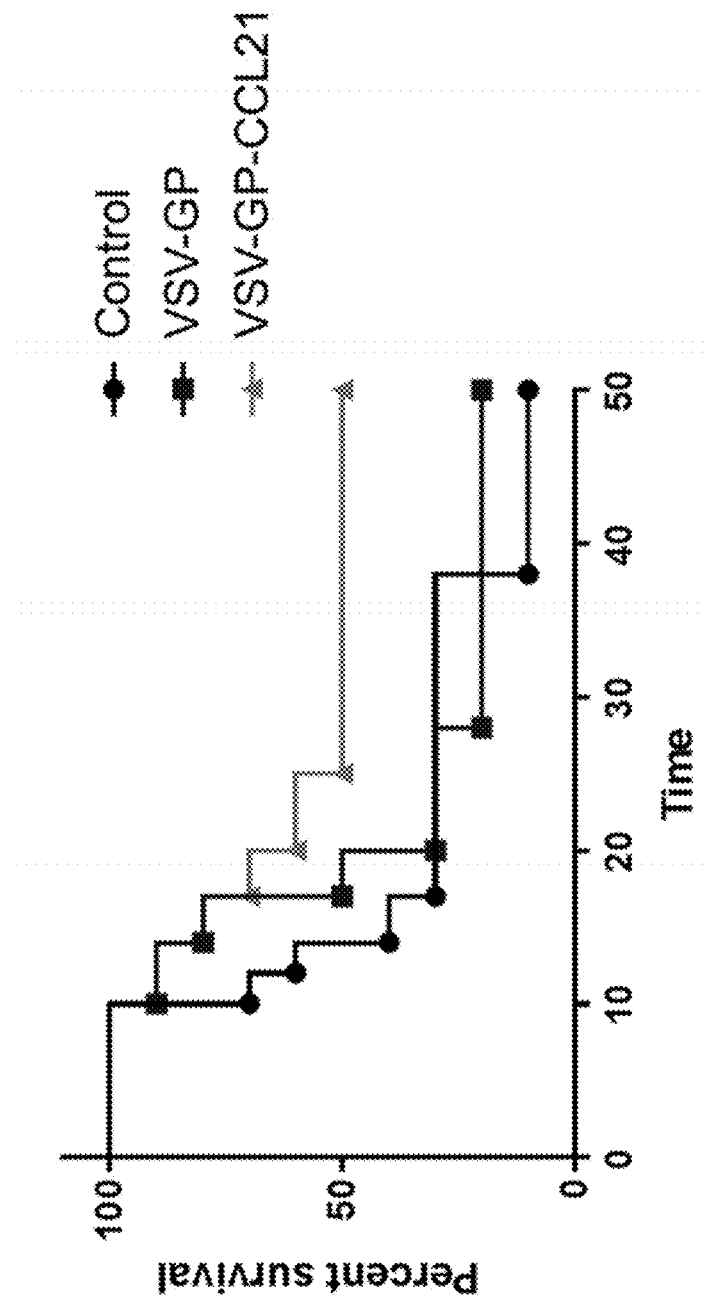
FIG. 14: Single tumor growth analysis of CT26.CL25-IFNARKO tumor-bearing control mice or mice treated with VSV-GP or VSV-GP-huCCL21.

In Vivo Efficacy of VSV-GP and VSV-GP-CCL21
Tumor Growth (FIG. 14)
The therapeutic potential of VSV-GP and VSV-GP-huCCL21 was assessed/compared using the CT26.CL25-IFNARKO tumor model. To this end established tumors were treated with two i.v. injections (day 0 and 3) of $2 \times 10^7$ TCID$_{50}$ VSV-GP or VSV-GP-huCCL21. Survival of mice treated as indicated is depicted in FIG. 14.

Example 6.3

Figure 20:
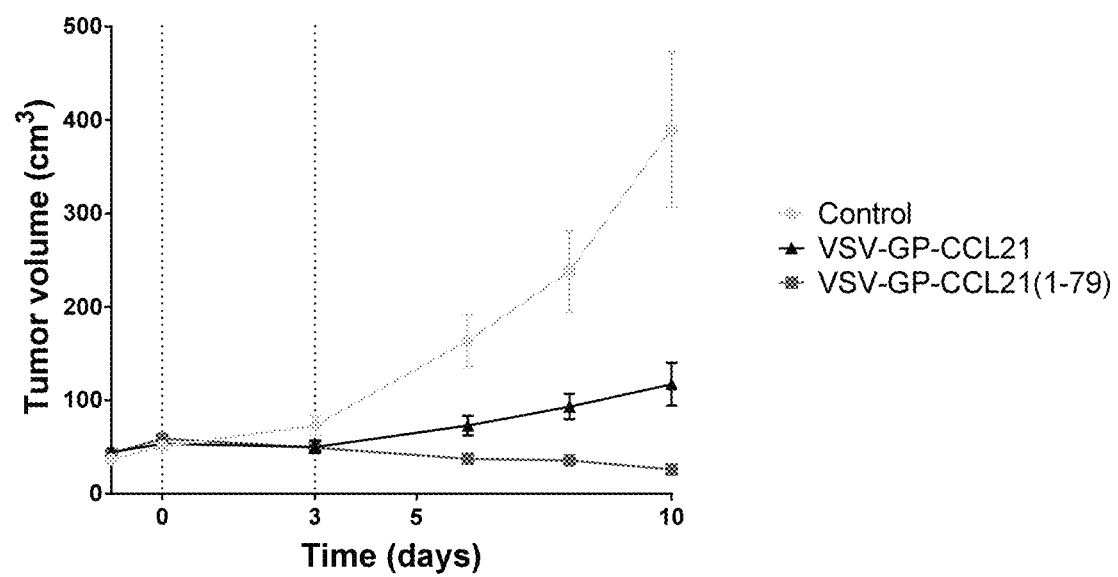
FIG. 20: Cumulative tumor growth in CT26.CL25-IFNARKO tumor-bearing control mice or mice treated with VSV-GP-huCCL21 or VSV-GP-huCCL21(1-79).

In Vivo Efficacy of VSV-GP-huCCL21 and VSV-GP-CCL21(1-79)
Tumor Growth/Survival (FIG. 20/21)
The therapeutic potential of VSV-GP-huCCL21 and VSV-GP-huCCL21(1-79) was assessed/compared using the CT26.CL25-IFNARKO tumor model. To this end established tumors were treated with two i.v. injections (day 0 and 3) of $2 \times 10^7$ TCID$_{50}$ VSV-GP-huCCL21 or VSV-GP-huCCL21(1-79). Cumulative tumor growth as well as 30-day survival of mice treated as indicated are depicted in FIG. 20/21. Treatment with the short CCL21 variant (CCL21(1-79)), corresponding to the fully plasmin processed (less aa 80/81) and freely diffusible form of human CCL21, was able to better control tumor growth and improve survival as compared to the full-length CCL21 bearing VSV-GP variant.

Example 6.4

Figure 22:
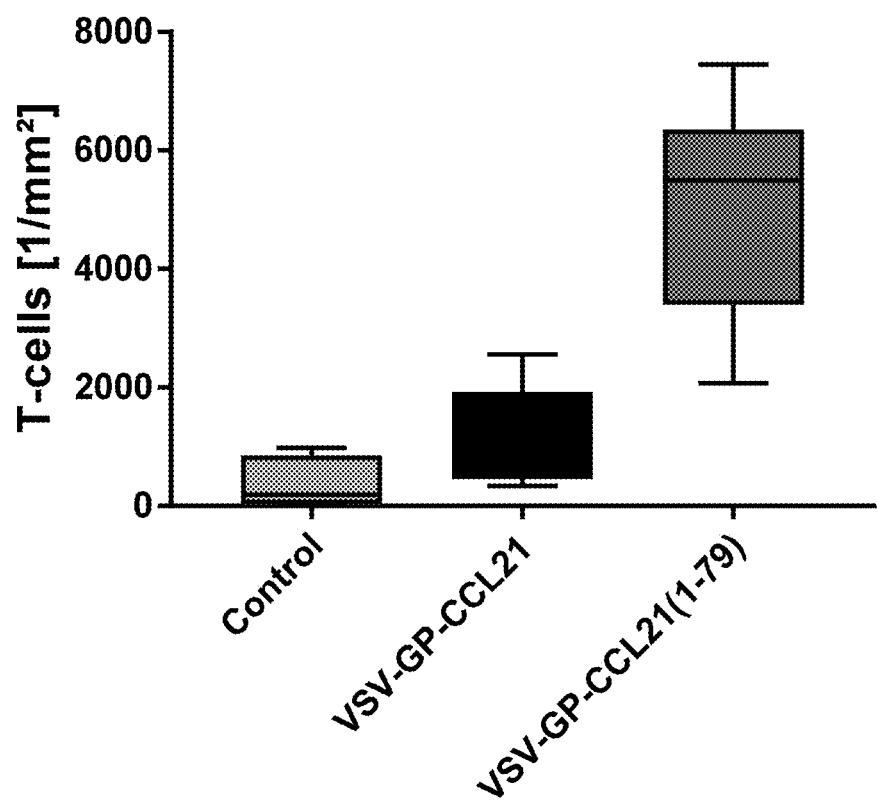
FIG. 22: IHC based quantitation of T-cell infiltration (viable, non-necrotic tumor segment) in CT26.CL25-IFNARKO tumor-bearing control mice or mice treated with VSV-GP-huCCL21 or VSV-GP-huCCL21(1-79).
Figure 23:
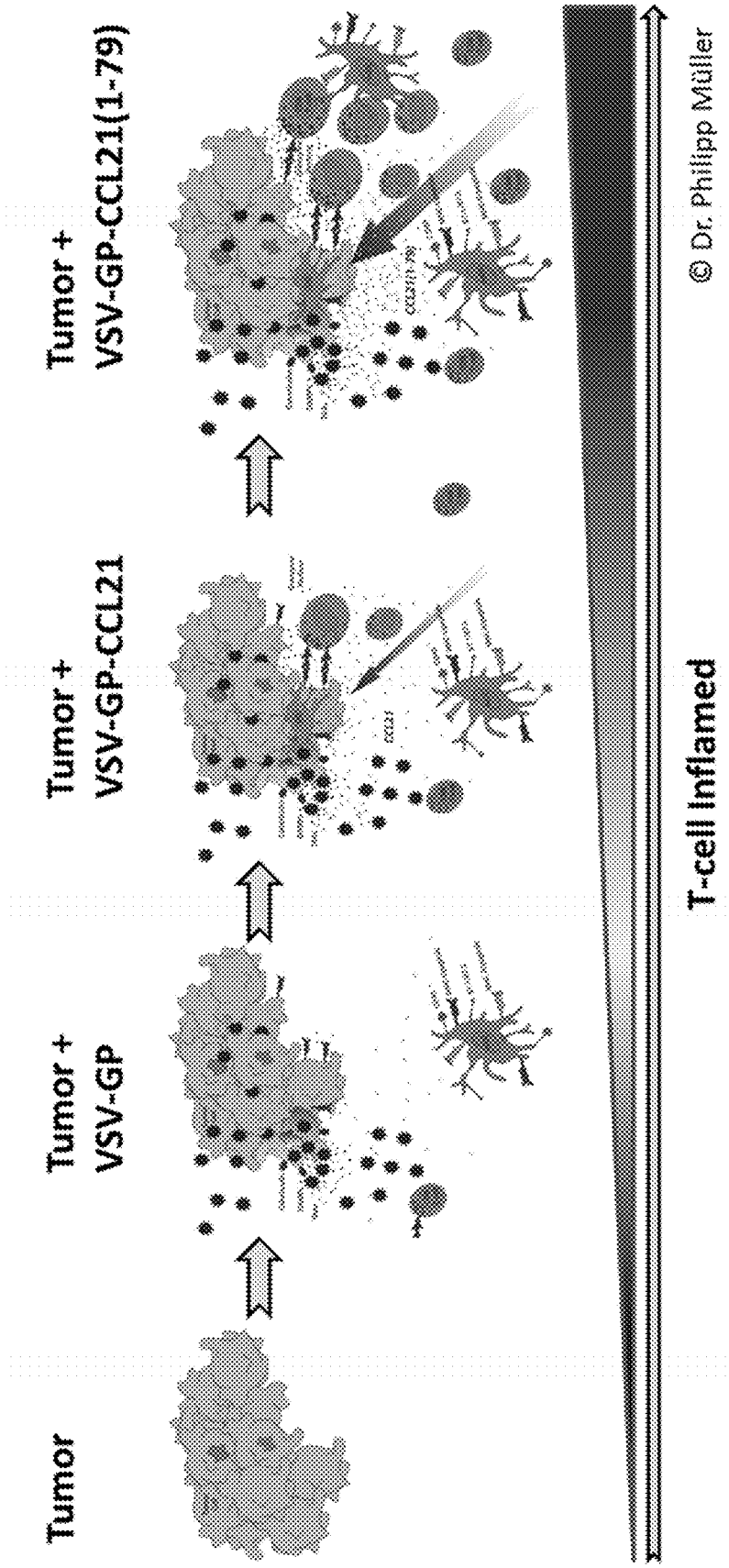
FIG. 23: Cartoon illustrating the impact of VSV-GP, VSV-GP-CCL21 (full length CCL21) and VSV-GP-CCL21 (1-79) (c-terminally truncated CCL21) on immune infiltration of virus infected tumors.

MoA: T-Cell Infiltration Induced by VSV-GP-huCCL21 and VSV-GP-huCCL21(1-79)
IHC (FIG. 22/23)
Tumors treated as under Example 6.3 were analyzed for T-cell infiltration. FFPE tumor sections were stained for CD4 and CD8 as well as VSV-N and cleaved Caspase3. Total T-cells (CD4+ & CD8+ cells) in the viable (non necrotic) tumor areas were quantitated. As depicted in FIG. 22 the short CCL21 variant (CCL21(1-79)), corresponding to the fully plasmin processed (less aa 80/81) and freely diffusible form of human CCL21, was able to attract more T-cells into the tumor, providing an explanation for the observed increase in efficacy (Example 6.3).

Figure 24:
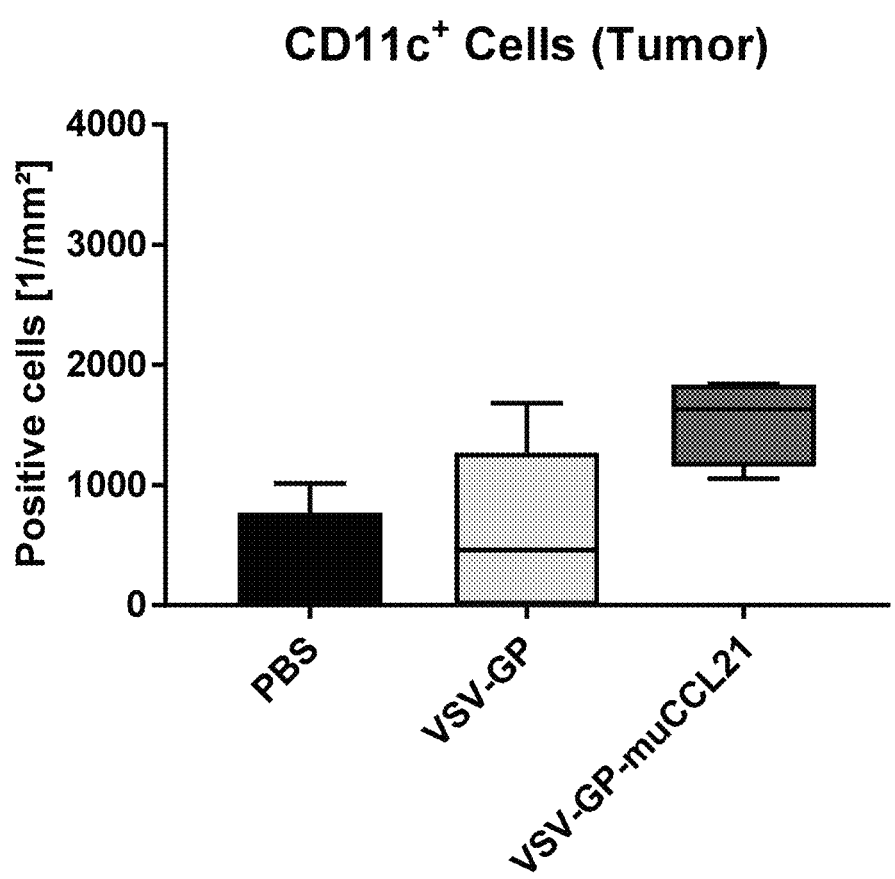
FIG. 24: IHC based quantitation of dendritic cell (CD11c positive) infiltration (tumor areas with active viral replication=necrotic margin) in CT26.CL25 tumor-bearing control mice or mice treated with VSV-GP or VSV-GP-muCCL21.

Additionally, virally expressed CCL21 was able to attract dendritic cells (CD11c positive) into infected CT26.CL25 tumors. Established CT26.CL25 tumors were locally (i.t.) injected with $2\times10^7$ $TCID_{50}$ of VSV-GP or VSV-GP-muCCL21 on day 0 and 3. FFPE sections of the respective tumors were analyzed for dendritic cell infiltration (tumor areas with active viral replication=necrotic margin)(see FIG. 24).

Example 7

Figure 9:
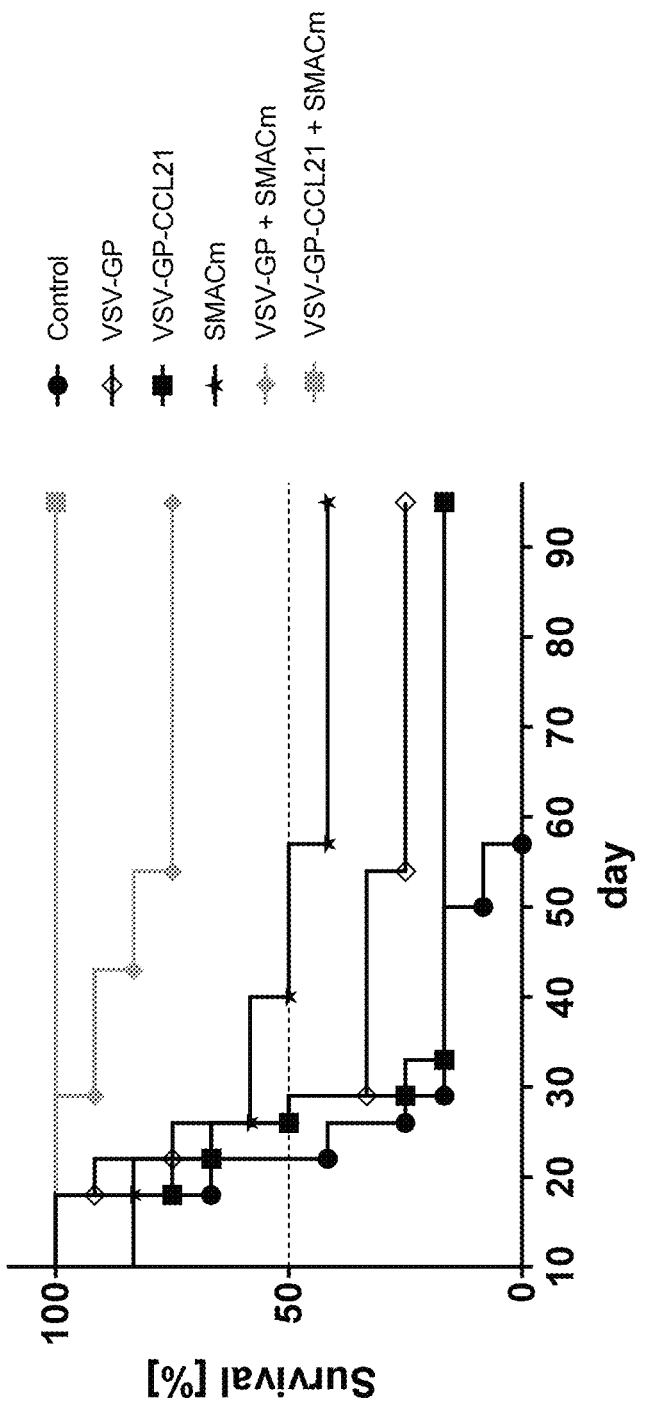
FIG. 9: Survival Analysis of the experiments depicted in FIGS. 7A-C and FIGS. 8A-C.

Efficacy: VSV-GP and VSV-GP-CCL21 Combo with SMACm
Tumor Growth/Survival (FIG. 7-9)

Building on the encouraging data from the combination of VSV-GP and a PD-1 blocking antibody (Example 2) further combinations were tested of VSV-GP (FIG. 7/9) and VSV-GP-muCCL21 (FIG. 8/9) with a SMAC mimetic (SMACm), a modulator of cellular death pathways rendering tumor cells more susceptible to cell death inducing stimuli/agents. The therapeutic interaction of the compounds was analyzed using the CT26.CL25-IFNARKO tumor model. To this end Balb/c mice with established CT26.CL25-IFNARKO tumors received a single i.v. treatment with $4\times10^6$ TCID50 of VSV-GP resp. VSV-GP-muCCL21 and/or 100 mg/kg of a SMACm given daily (p.o.) for a period of two weeks, starting on the same day as the VSV-GP resp. VSV-GP-muCCL21 treatment. Combination of VSV-GP and SMACm resulted in improved efficacy as compared to the corresponding monotherapies. When combining VSV-GP-muCCL21 with a SMACm the combinatorial effects were even more pronounced resulting in the cure of all treated animals.

The invention claimed is:

1. A recombinant vesicular stomatitis virus encoding in its genome at least one human CCL21 protein having a c-terminal truncation wherein said truncated CCL21 protein comprises the amino acids 1-79, 1-81, 1-88, or 1-91, as shown in SEQ ID NO:2 and having at least 80% identity to SEQ ID NO:3, and wherein the gene coding for the glycoprotein G of the recombinant vesicular stomatitis virus is replaced by the gene coding for the glycoprotein GP of Lymphocyte choriomeningitis virus (LCMV), and/or the glycoprotein G is replaced by the glycoprotein GP of LCMV.

2. The recombinant vesicular stomatitis virus according to claim 1, wherein said genome encodes for a plasmin processed truncated human CCL21 protein consisting of the amino acids 1-79, 1-81, 1-88, or 1-91, as shown in SEQ ID NO:2.

3. The recombinant vesicular stomatitis virus according to claim 1, wherein said genome encodes for a c-terminally truncated human CCL21 protein consisting of SEQ ID NO:3.

4. The recombinant vesicular stomatitis virus according to claim 1, wherein the said genome encodes for a truncated human CCL21 protein comprising SEQ ID NO:3 or having at least 96% identity to SEQ ID NO:3.

5. The recombinant vesicular stomatitis virus according to claim 1, wherein said truncated human CCL21 protein has at least 80% identity to SEQ ID NO:4.

6. The recombinant vesicular stomatitis virus according to claim 1, wherein the sequence encoding said truncated human CCL21 protein further comprises a signal peptide sequence operably linked to said human CCL2 protein encoding sequence.

7. The recombinant vesicular stomatitis virus according to claim 6 wherein the sequence encoding said human truncated CCL21 protein operably linked to signal sequence comprises SEQ ID NO:5 or a sequence having at least 80% identity to SEQ ID NO:5.

8. The recombinant vesicular stomatitis virus according to claim 1, encoding in its genome a vesicular stomatitis virus nucleoprotein (N) wherein the nucleoprotein (N) comprises an amino acid sequence as set forth in SEQ ID NO: 7 or at least 98% identical to SEQ ID NO: 7.

9. The recombinant vesicular stomatitis virus according to claim 1, encoding in its genome a vesicular stomatitis virus phosphoprotein (P) wherein the phosphoprotein (P) comprises an amino acid sequence as set forth in SEQ ID NO: 8 or at least 98% identical to SEQ ID NO: 8.

10. The recombinant vesicular stomatitis virus according to claim 1, encoding in its genome a vesicular stomatitis virus large protein (L) wherein the large protein (L) comprises an amino acid sequence as set forth in SEQ ID NO:9 or at least 98% identical to SEQ ID NO:9.

11. The recombinant vesicular stomatitis virus according to claim 1, encoding in its genome a vesicular stomatitis virus matrix protein (M) wherein the matrix protein (M) comprises an amino acid sequence as set forth in SEQ ID NO:10 or at least 98% identical to SEQ ID NO:10.

12. The recombinant vesicular stomatitis virus according to claim 1, encoding in its genome:
  the vesicular stomatitis virus nucleoprotein (N) comprising an amino acid sequence as set forth in SEQ ID NO:7 or at least 98% identical to SEQ ID NO:7
  the vesicular stomatitis virus phosphoprotein (P) comprising an amino acid sequence as set forth in SEQ ID NO:8 or at least 98% identical to SEQ ID NO:8
  the vesicular stomatitis virus large protein (L) comprising an amino acid sequence as set forth in SEQ ID NO:9 or at least 98% identical to SEQ ID NO:9, and
  the vesicular stomatitis virus matrix protein (M) comprising an amino acid sequence as set forth in SEQ ID NO:10 or at least 98% identical to SEQ ID NO:10.

13. The recombinant vesicular stomatitis virus according to claim 1, which is replication-competent.

14. A recombinant vesicular stomatitis virus encoding in its genome a vesicular stomatitis virus nucleoprotein (N), large protein (L), phosphoprotein (P), matrix protein (M), glycoprotein (G) and at least one human truncated CCL21 protein comprising the amino acids 1-79, 1-81, 1-88, or 1-91, as shown in SEQ ID NO:2 and having at least 80% identity to SEQ ID NO:3, and further comprising a signal sequence operably linked to said truncated CCL21 protein,
  wherein the gene coding for the glycoprotein G of the vesicular stomatitis virus is replaced by the gene coding for the glycoprotein GP of lymphocyte choriomeningitis virus (LCMV), and/or the glycoprotein G is replaced by the glycoprotein GP of LCMV, and wherein
  the nucleoprotein (N) comprises an amino acid as set forth in SEQ ID NO:7 or a at least 98% identical to SEQ ID NO:7
  wherein the phosphoprotein (P) comprises an amino acid as set forth in SEQ ID NO:8 or at least 98% identical to SEQ ID NO:8
  wherein the large protein (L) comprises an amino acid as set forth in SEQ ID NO:9 or at least 98% identical to SEQ ID NO:9
  the matrix protein (M) comprises an amino acid as set forth in SEQ ID NO:10 or at least 98% identical to SEQ ID NO:10.

15. A pharmaceutical composition, characterized in that the composition comprises a recombinant vesicular stomatitis virus according to claim 1.

16. A method for the treatment of solid cancers, comprising administration of a recombinant vesicular stomatitis virus according to claim 1 or a pharmaceutical composition comprising said vesicular stomatitis virus.

17. The method according to claim 16, wherein the solid cancer is selected from the list comprising: reproductive tumor, an ovarian tumor, a testicular tumor, an endocrine tumor, a gastrointestinal tumor, a pancreatic tumor, a liver tumor, a kidney tumor, a colon tumor, a colorectal tumor, a bladder tumor, a prostate tumor, a skin tumor, melanoma, a respiratory tumor, a lung tumor, a breast tumor, a head & neck tumor, a head and neck squamous-cell carcinoma (HNSCC) and a bone tumor.

18. The method according to claim 16, wherein administration of the recombinant vesicular stomatitis virus or the pharmaceutical composition is intratumorally or intravenously.

19. The method according to claim 16, wherein administration of the recombinant vesicular stomatitis virus or the pharmaceutical composition is at least once intratumorally and subsequently intravenously.

20. The method according to claim 19, wherein the subsequent intravenous administration is given 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the initial intratumoral administration.

21. A composition comprising a recombinant vesicular stomatitis virus according to claim 1 and further a PD-1 pathway inhibitor or a SMAC mimetic.

22. The composition according to claim 21, wherein the PD-1 pathway inhibitor is an antagonistic antibody which is directed against PD-1 or PD-L1.

23. The composition according to claim 21, wherein the SMAC mimetic is selected from the group consisting of any one of compounds 1 to 26:

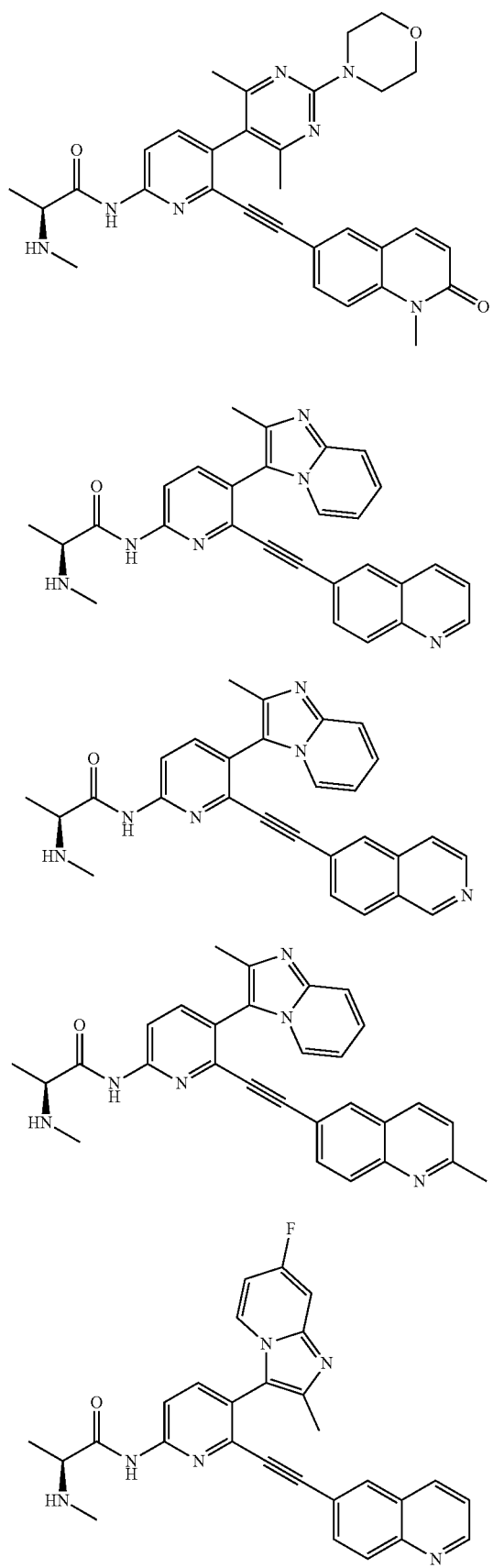
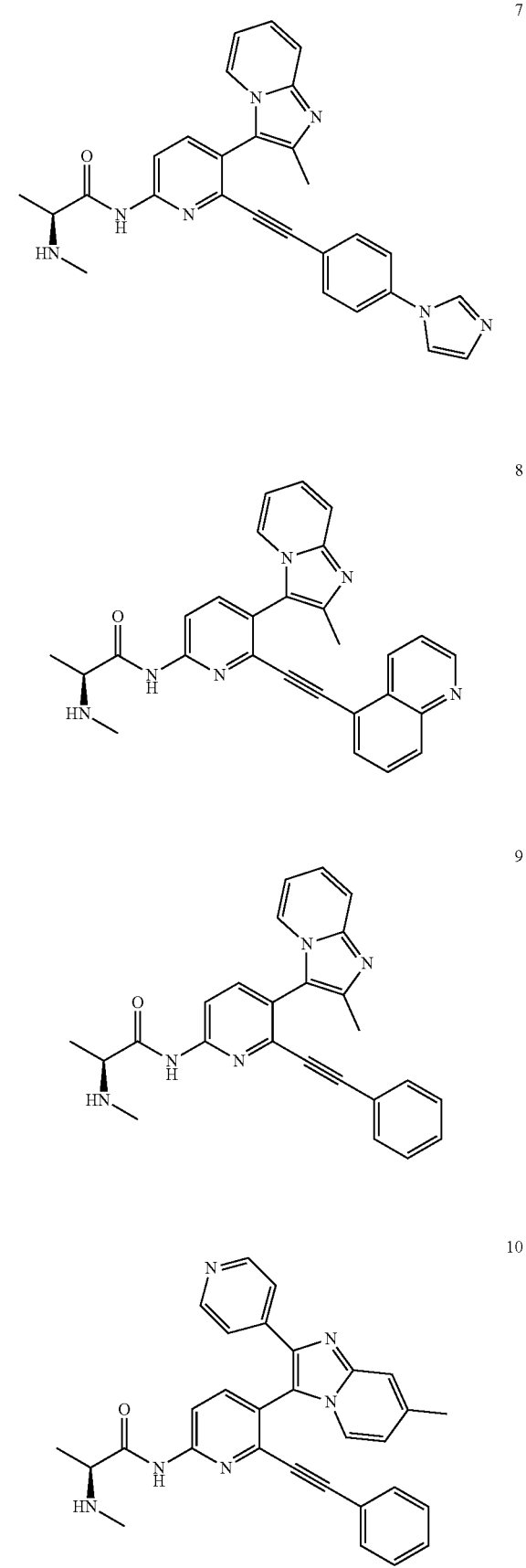

11
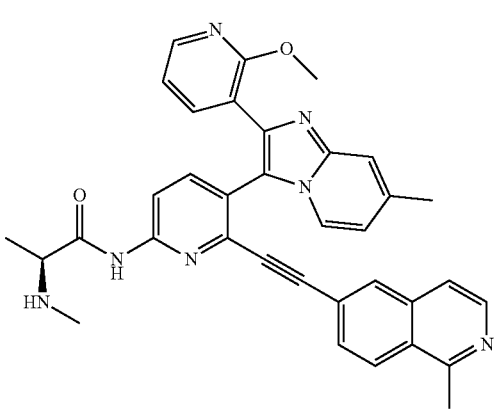
15
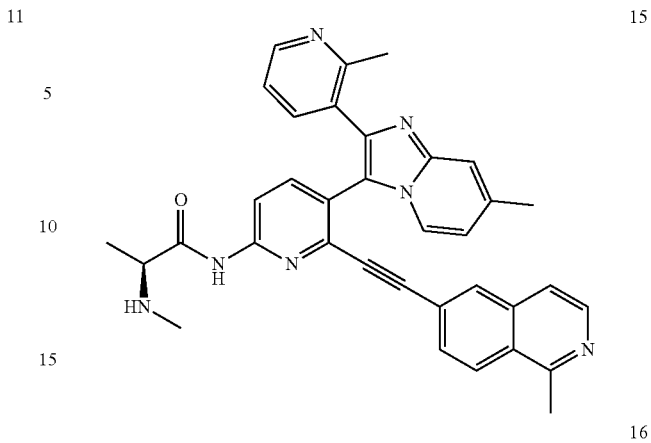
12
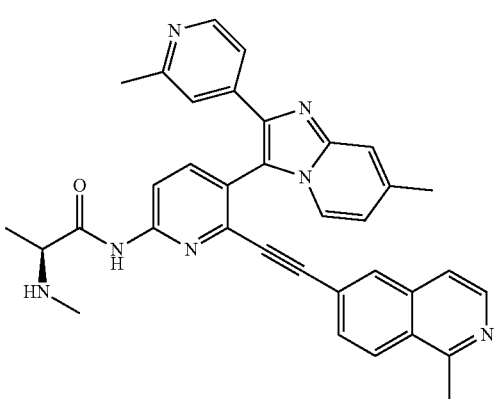
16
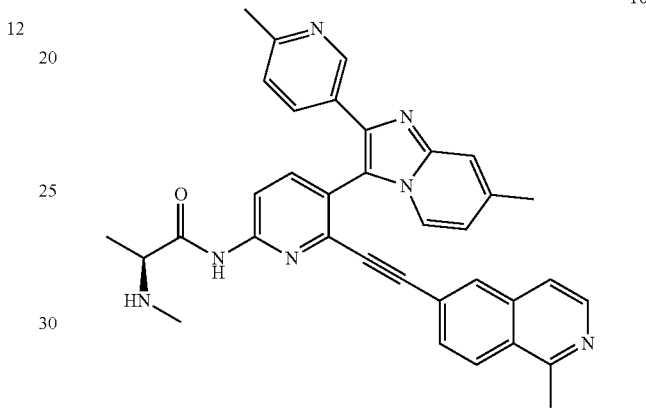
13
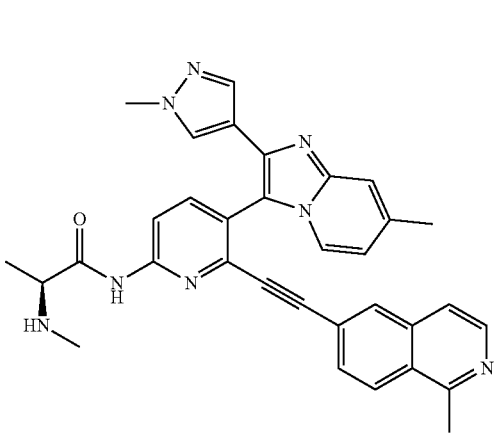
17
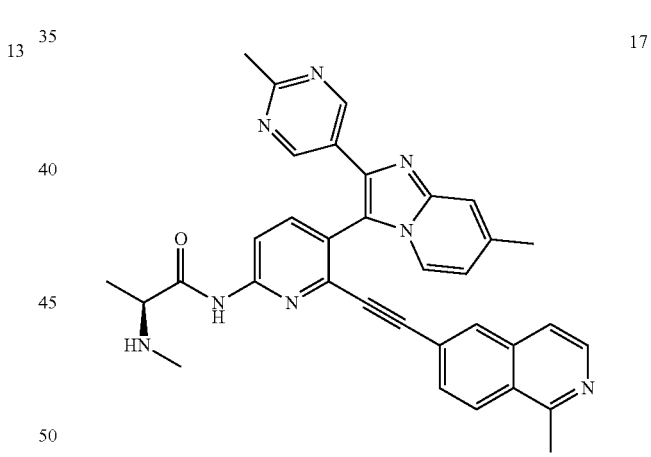
14
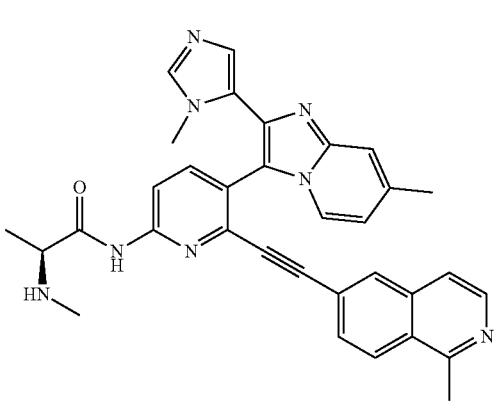
18
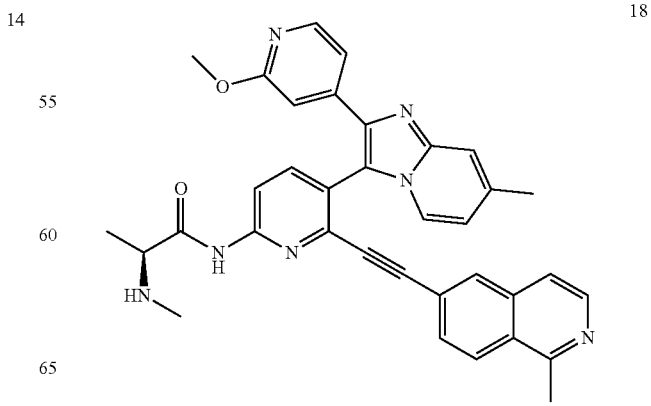

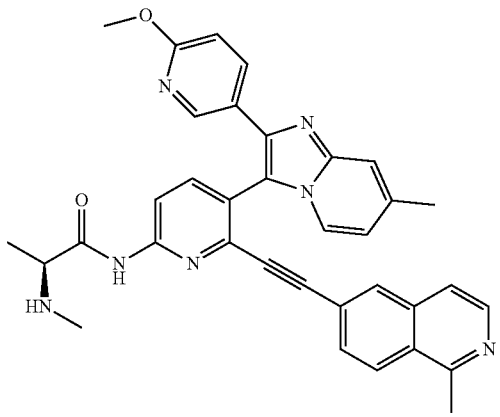
19
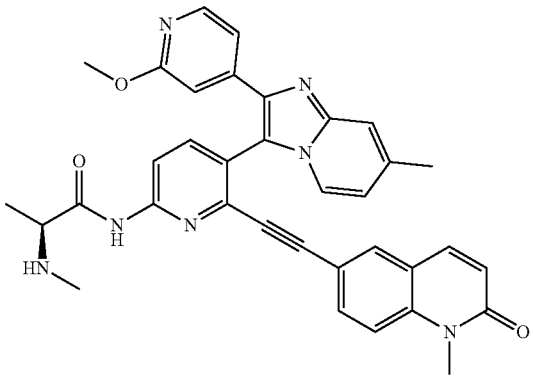 [SMILES: CN[C@@H](C)C(=O)Nc1ccc(-c2c(-c3ccnc(OC)c3)nc3cc(C)ccn23)c(C#Cc2ccc3c(ccc(=O)n3C)c2)n1]
23
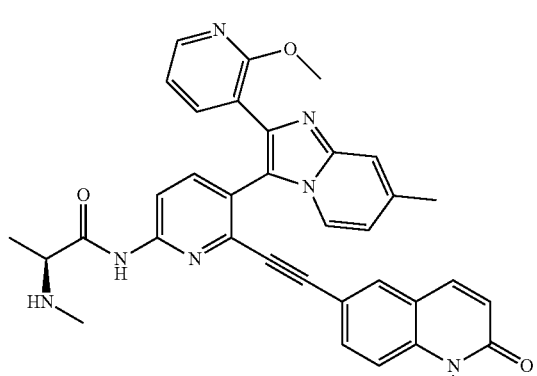
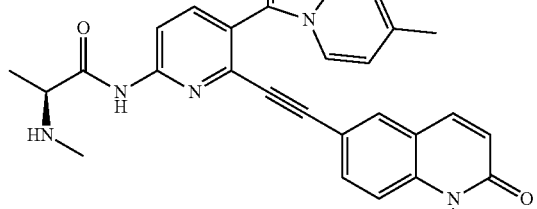
20
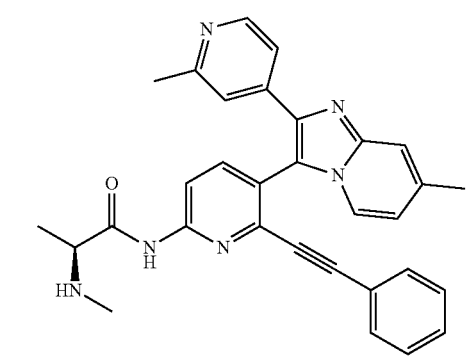
21
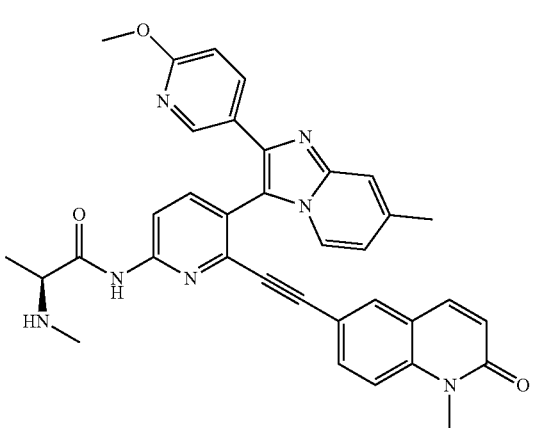
24
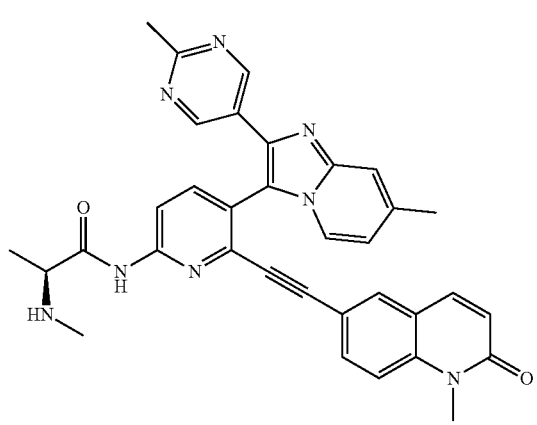
22
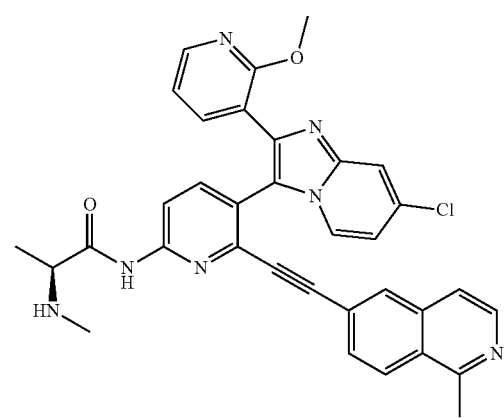
25

-continued

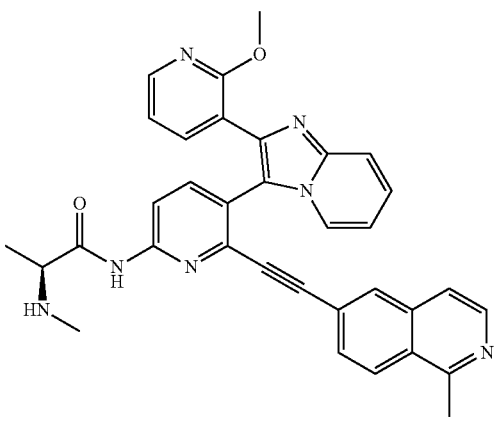

or a pharmaceutically acceptable salt of one of these compounds.

24. The composition according to claim 21, wherein the PD-1 pathway inhibitor is an antagonist selected from the group consisting of pembrolizumab, nivolumab, pidilizumab, atezolizumab, avelumab, durvalumab, PDR-001, PD1-1, PD1-2, PD1-3, PD1-4 and PD1-5.

25. A kit of parts comprising:
a) a recombinant vesicular stomatitis virus as defined in claim 1, or a pharmaceutical composition comprising said recombinant vesicular stomatitis virus, and
b) a PD-1 pathway inhibitor or SMAC mimetic.

26. The method according to claim 16, wherein the recombinant vesicular stomatitis virus, or the pharmaceutical composition is administered in combination with a PD-1 pathway inhibitor or a SMAC mimetic.

27. The method according to claim 26, wherein the recombinant vesicular stomatitis virus, or the pharmaceutical composition is administered concomittantly, sequentially or alternately with the PD-1 pathway inhibitor or the SMAC mimetic.

28. The method according to claim 26, wherein the SMAC mimetic is selected from the group consisting of any one of compounds 1 to 26 according to claim 23 or a pharmaceutically acceptable salt of one of these compounds.

29. The method according to claim 26, wherein the PD-1 pathway inhibitor is selected from the group consisting of pembrolizumab, nivolumab, pidilizumab, atezolizumab, avelumab, durvalumab, PDR-001, PD1-1, PD1-2, PD1-3, PD1-4 and PD1-5.

30. The method according to claim 26, wherein the recombinant vesicular stomatitis virus or the pharmaceutical composition is administered via a different administration route then the PD-1 pathway inhibitor or the SMAC mimetic.

31. The method according to claim 26, wherein the recombinant vesicular stomatitis virus or the pharmaceutical composition are administered at least once intratumorally and the PD-1 pathway inhibitor or the SMAC mimetic is administered intravenously.

32. A virus producing cell, characterized in that the cell produces a recombinant vesicular stomatitis virus according claim 1.

33. The virus producing cell of claim 32, characterized in that the cell is a Vero cell, a HEK cell, a HEK293 cell, a Chinese hamster ovary cell (CHO), or a baby hamster kidney (BHK) cell.

34. A recombinant rhabdovirus encoding in its RNA genome at least one human CCL21 protein, wherein the RNA genome of the recombinant rhabdovirus comprises or consists of a coding sequence identical or at least 75%, identical to SEQ ID NO: 24.

* * * * *

SEQUENCE LISTING

```
<160> NUMBER OF SEQ ID NOS: 24

<210> SEQ ID NO 1
<211> LENGTH: 134
<212> TYPE: PRT
<213> ORGANISM: Homo sapiens

<400> SEQUENCE: 1

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 2
<211> LENGTH: 111
<212> TYPE: PRT
<213> ORGANISM: Homo sapiens

<400> SEQUENCE: 2

Ser Asp Gly Gly Ala Gln Asp Cys Cys Leu Lys Tyr Ser Gln Arg Lys
1               5                   10                  15

Ile Pro Ala Lys Val Val Arg Ser Tyr Arg Lys Gln Glu Pro Ser Leu
            20                  25                  30

Gly Cys Ser Ile Pro Ala Ile Leu Phe Leu Pro Arg Lys Arg Ser Gln
        35                  40                  45

Ala Glu Leu Cys Ala Asp Pro Lys Glu Leu Trp Val Gln Gln Leu Met
    50                  55                  60
```

-continued

Gln His Leu Asp Lys Thr Pro Ser Pro Gln Lys Pro Ala Gln Gly Cys
65                  70                  75                  80

Arg Lys Asp Arg Gly Ala Ser Lys Thr Gly Lys Lys Gly Lys Gly Ser
                85                  90                  95

Lys Gly Cys Lys Arg Thr Glu Arg Ser Gln Thr Pro Lys Gly Pro
            100                 105                 110

<210> SEQ ID NO 3
<211> LENGTH: 79
<212> TYPE: PRT
<213> ORGANISM: Homo sapiens

<400> SEQUENCE: 3

Ser Asp Gly Gly Ala Gln Asp Cys Cys Leu Lys Tyr Ser Gln Arg Lys
1               5                   10                  15

Ile Pro Ala Lys Val Val Arg Ser Tyr Arg Lys Gln Glu Pro Ser Leu
                20                  25                  30

Gly Cys Ser Ile Pro Ala Ile Leu Phe Leu Pro Arg Lys Arg Ser Gln
            35                  40                  45

Ala Glu Leu Cys Ala Asp Pro Lys Glu Leu Trp Val Gln Gln Leu Met
        50                  55                  60

Gln His Leu Asp Lys Thr Pro Ser Pro Gln Lys Pro Ala Gln Gly
65                  70                  75

<210> SEQ ID NO 4
<211> LENGTH: 81
<212> TYPE: PRT
<213> ORGANISM: Homo sapiens

<400> SEQUENCE: 4

Ser Asp Gly Gly Ala Gln Asp Cys Cys Leu Lys Tyr Ser Gln Arg Lys
1               5                   10                  15

Ile Pro Ala Lys Val Val Arg Ser Tyr Arg Lys Gln Glu Pro Ser Leu
                20                  25                  30

Gly Cys Ser Ile Pro Ala Ile Leu Phe Leu Pro Arg Lys Arg Ser Gln
            35                  40                  45

Ala Glu Leu Cys Ala Asp Pro Lys Glu Leu Trp Val Gln Gln Leu Met
        50                  55                  60

Gln His Leu Asp Lys Thr Pro Ser Pro Gln Lys Pro Ala Gln Gly Cys
65                  70                  75                  80

Arg

<210> SEQ ID NO 5
<211> LENGTH: 98
<212> TYPE: PRT
<213> ORGANISM: Homo sapiens

<400> SEQUENCE: 5

Met Gly Trp Ser Cys Ile Ile Leu Phe Leu Val Ala Thr Ala Thr Gly
1               5                   10                  15

Val His Ser Ser Asp Gly Gly Ala Gln Asp Cys Cys Leu Lys Tyr Ser
                20                  25                  30

Gln Arg Lys Ile Pro Ala Lys Val Val Arg Ser Tyr Arg Lys Gln Glu
            35                  40                  45

Pro Ser Leu Gly Cys Ser Ile Pro Ala Ile Leu Phe Leu Pro Arg Lys
        50                  55                  60

Arg Ser Gln Ala Glu Leu Cys Ala Asp Pro Lys Glu Leu Trp Val Gln 65 70 75 80

Gln Leu Met Gln His Leu Asp Lys Thr Pro Ser Pro Gln Lys Pro Ala
85 90 95

Gln Gly

<210> SEQ ID NO 6
<211> LENGTH: 19
<212> TYPE: PRT
<213> ORGANISM: Mus musculus

<400> SEQUENCE: 6

Met Gly Trp Ser Cys Ile Ile Leu Phe Leu Val Ala Thr Ala Thr Gly
1 5 10 15

Val His Ser

<210> SEQ ID NO 7
<211> LENGTH: 422
<212> TYPE: PRT
<213> ORGANISM: Vesicular stomatitis virus

<400> SEQUENCE: 7

Met Ser Val Thr Val Lys Arg Ile Ile Asp Asn Thr Val Val Val Pro
1 5 10 15

Lys Leu Pro Ala Asn Glu Asp Pro Val Glu Tyr Pro Ala Asp Tyr Phe
20 25 30

Arg Lys Ser Lys Glu Ile Pro Leu Tyr Ile Asn Thr Thr Lys Ser Leu
35 40 45

Ser Asp Leu Arg Gly Tyr Val Tyr Gln Gly Leu Lys Ser Gly Asn Val
50 55 60

Ser Ile Ile His Val Asn Ser Tyr Leu Tyr Gly Ala Leu Lys Asp Ile
65 70 75 80

Arg Gly Lys Leu Asp Lys Asp Trp Ser Ser Phe Gly Ile Asn Ile Gly
85 90 95

Lys Ala Gly Asp Thr Ile Gly Ile Phe Asp Leu Val Ser Leu Lys Ala
100 105 110

Leu Asp Gly Val Leu Pro Asp Gly Val Ser Asp Ala Ser Arg Thr Ser
115 120 125

Ala Asp Asp Lys Trp Leu Pro Leu Tyr Leu Leu Gly Leu Tyr Arg Val
130 135 140

Gly Arg Thr Gln Met Pro Glu Tyr Arg Lys Lys Leu Met Asp Gly Leu
145 150 155 160

Thr Asn Gln Cys Lys Met Ile Asn Glu Gln Phe Glu Pro Leu Val Pro
165 170 175

Glu Gly Arg Asp Ile Phe Asp Val Trp Gly Asn Asp Ser Asn Tyr Thr
180 185 190

Lys Ile Val Ala Ala Val Asp Met Phe Phe His Met Phe Lys Lys His
195 200 205

Glu Cys Ala Ser Phe Arg Tyr Gly Thr Ile Val Ser Arg Phe Lys Asp
210 215 220

Cys Ala Ala Leu Ala Thr Phe Gly His Leu Cys Lys Ile Thr Gly Met
225 230 235 240

Ser Thr Glu Asp Val Thr Thr Trp Ile Leu Asn Arg Glu Val Ala Asp
245 250 255

Glu Met Val Gln Met Met Leu Pro Gly Gln Glu Ile Asp Lys Ala Asp
260 265 270

```
Ser Tyr Met Pro Tyr Leu Ile Asp Phe Gly Leu Ser Ser Lys Ser Pro
            275                 280                 285

Tyr Ser Ser Val Lys Asn Pro Ala Phe His Phe Trp Gly Gln Leu Thr
    290                 295                 300

Ala Leu Leu Leu Arg Ser Thr Arg Ala Arg Asn Ala Arg Gln Pro Asp
305                 310                 315                 320

Asp Ile Glu Tyr Thr Ser Leu Thr Thr Ala Gly Leu Leu Tyr Ala Tyr
                325                 330                 335

Ala Val Gly Ser Ser Ala Asp Leu Ala Gln Gln Phe Cys Val Gly Asp
            340                 345                 350

Asn Lys Tyr Thr Pro Asp Asp Ser Thr Gly Gly Leu Thr Thr Asn Ala
        355                 360                 365

Pro Pro Gln Gly Arg Asp Val Val Glu Trp Leu Gly Trp Phe Glu Asp
370                 375                 380

Gln Asn Arg Lys Pro Thr Pro Asp Met Met Gln Tyr Ala Lys Arg Ala
385                 390                 395                 400

Val Met Ser Leu Gln Gly Leu Arg Glu Lys Thr Ile Gly Lys Tyr Ala
                405                 410                 415

Lys Ser Glu Phe Asp Lys
            420

<210> SEQ ID NO 8
<211> LENGTH: 265
<212> TYPE: PRT
<213> ORGANISM: Vesicular stomatitis virus

<400> SEQUENCE: 8

Met Asp Asn Leu Thr Lys Val Arg Glu Tyr Leu Lys Ser Tyr Ser Arg
1               5                   10                  15

Leu Asp Gln Ala Val Gly Glu Ile Asp Glu Ile Glu Ala Gln Arg Ala
            20                  25                  30

Glu Lys Ser Asn Tyr Glu Leu Phe Gln Glu Asp Gly Val Glu Glu His
        35                  40                  45

Thr Lys Pro Ser Tyr Phe Gln Ala Ala Asp Asp Ser Asp Thr Glu Ser
    50                  55                  60

Glu Pro Glu Ile Glu Asp Asn Gln Gly Leu Tyr Ala Pro Asp Pro Glu
65                  70                  75                  80

Ala Glu Gln Val Glu Gly Phe Ile Gln Gly Pro Leu Asp Asp Tyr Ala
                85                  90                  95

Asp Glu Glu Val Asp Val Val Phe Thr Ser Asp Trp Lys Gln Pro Glu
            100                 105                 110

Leu Glu Ser Asp Glu His Gly Lys Thr Leu Arg Leu Thr Ser Pro Glu
        115                 120                 125

Gly Leu Ser Gly Glu Gln Lys Ser Gln Trp Leu Ser Thr Ile Lys Ala
    130                 135                 140

Val Val Gln Ser Ala Lys Tyr Trp Asn Leu Ala Glu Cys Thr Phe Glu
145                 150                 155                 160

Ala Ser Gly Glu Gly Val Ile Met Lys Glu Arg Gln Ile Thr Pro Asp
                165                 170                 175

Val Tyr Lys Val Thr Pro Val Met Asn Thr His Pro Ser Gln Ser Glu
            180                 185                 190

Ala Val Ser Asp Val Trp Ser Leu Ser Lys Thr Ser Met Thr Phe Gln
        195                 200                 205

Pro Lys Lys Ala Ser Leu Gln Pro Leu Thr Ile Ser Leu Asp Glu Leu
    210                 215                 220
```

```
Phe Ser Ser Arg Gly Glu Phe Ile Ser Val Gly Asp Gly Arg Met
225                 230                 235                 240

Ser His Lys Glu Ala Ile Leu Leu Gly Leu Arg Tyr Lys Lys Leu Tyr
            245                 250                 255

Asn Gln Ala Arg Val Lys Tyr Ser Leu
        260                 265

<210> SEQ ID NO 9
<211> LENGTH: 2109
<212> TYPE: PRT
<213> ORGANISM: Vesicular stomatitis virus

<400> SEQUENCE: 9

Met Glu Val His Asp Phe Glu Thr Asp Glu Phe Asn Asp Phe Asn Glu
1               5                   10                  15

Asp Asp Tyr Ala Thr Arg Glu Phe Leu Asn Pro Asp Glu Arg Met Thr
            20                  25                  30

Tyr Leu Asn His Ala Asp Tyr Asn Leu Asn Ser Pro Leu Ile Ser Asp
        35                  40                  45

Asp Ile Asp Asn Leu Ile Arg Lys Phe Asn Ser Leu Pro Ile Pro Ser
    50                  55                  60

Met Trp Asp Ser Lys Asn Trp Asp Gly Val Leu Glu Met Leu Thr Ser
65                  70                  75                  80

Cys Gln Ala Asn Pro Ile Pro Thr Ser Gln Met His Lys Trp Met Gly
                85                  90                  95

Ser Trp Leu Met Ser Asp Asn His Asp Ala Ser Gln Gly Tyr Ser Phe
            100                 105                 110

Leu His Glu Val Asp Lys Glu Ala Glu Ile Thr Phe Asp Val Val Glu
        115                 120                 125

Thr Phe Ile Arg Gly Trp Gly Asn Lys Pro Ile Glu Tyr Ile Lys Lys
    130                 135                 140

Glu Arg Trp Thr Asp Ser Phe Lys Ile Leu Ala Tyr Leu Cys Gln Lys
145                 150                 155                 160

Phe Leu Asp Leu His Lys Leu Thr Leu Ile Leu Asn Ala Val Ser Glu
                165                 170                 175

Val Glu Leu Leu Asn Leu Ala Arg Thr Phe Lys Gly Lys Val Arg Arg
            180                 185                 190

Ser Ser His Gly Thr Asn Ile Cys Arg Ile Arg Val Pro Ser Leu Gly
        195                 200                 205

Pro Thr Phe Ile Ser Glu Gly Trp Ala Tyr Phe Lys Lys Leu Asp Ile
    210                 215                 220

Leu Met Asp Arg Asn Phe Leu Leu Met Val Lys Asp Val Ile Ile Gly
225                 230                 235                 240

Arg Met Gln Thr Val Leu Ser Met Val Cys Arg Ile Asp Asn Leu Phe
                245                 250                 255

Ser Glu Gln Asp Ile Phe Ser Leu Leu Asn Ile Tyr Arg Ile Gly Asp
            260                 265                 270

Lys Ile Val Glu Arg Gln Gly Asn Phe Ser Tyr Asp Leu Ile Lys Met
        275                 280                 285

Val Glu Pro Ile Cys Asn Leu Lys Leu Met Lys Leu Ala Arg Glu Ser
    290                 295                 300

Arg Pro Leu Val Pro Gln Phe Pro His Phe Glu Asn His Ile Lys Thr
305                 310                 315                 320

Ser Val Asp Glu Gly Ala Lys Ile Asp Arg Gly Ile Arg Phe Leu His
```

-continued

```
                325                 330                 335
Asp Gln Ile Met Ser Val Lys Thr Val Asp Leu Thr Leu Val Ile Tyr
                340                 345                 350
Gly Ser Phe Arg His Trp Gly His Pro Phe Ile Asp Tyr Tyr Thr Gly
                355                 360                 365
Leu Glu Lys Leu His Ser Gln Val Thr Met Lys Lys Asp Ile Asp Val
                370                 375                 380
Ser Tyr Ala Lys Ala Leu Ala Ser Asp Leu Ala Arg Ile Val Leu Phe
385                 390                 395                 400
Gln Gln Phe Asn Asp His Lys Lys Trp Phe Val Asn Gly Asp Leu Leu
                405                 410                 415
Pro His Asp His Pro Phe Lys Ser His Val Lys Glu Asn Thr Trp Pro
                420                 425                 430
Thr Ala Ala Gln Val Gln Asp Phe Gly Asp Lys Trp His Glu Leu Pro
                435                 440                 445
Leu Ile Lys Cys Phe Glu Ile Pro Asp Leu Leu Asp Pro Ser Ile Ile
                450                 455                 460
Tyr Ser Asp Lys Ser His Ser Met Asn Arg Ser Glu Val Leu Lys His
465                 470                 475                 480
Val Arg Met Asn Pro Asn Thr Pro Ile Pro Ser Lys Lys Val Leu Gln
                485                 490                 495
Thr Met Leu Asp Thr Lys Ala Thr Asn Trp Lys Glu Phe Leu Lys Glu
                500                 505                 510
Ile Asp Glu Lys Gly Leu Asp Asp Asp Leu Ile Ile Gly Leu Lys
                515                 520                 525
Gly Lys Glu Arg Glu Leu Lys Leu Ala Gly Arg Phe Phe Ser Leu Met
                530                 535                 540
Ser Trp Lys Leu Arg Glu Tyr Phe Val Ile Thr Glu Tyr Leu Ile Lys
545                 550                 555                 560
Thr His Phe Val Pro Met Phe Lys Gly Leu Thr Met Ala Asp Asp Leu
                565                 570                 575
Thr Ala Val Ile Lys Lys Met Leu Asp Ser Ser Ser Gly Gln Gly Leu
                580                 585                 590
Lys Ser Tyr Glu Ala Ile Cys Ile Ala Asn His Ile Asp Tyr Glu Lys
                595                 600                 605
Trp Asn Asn His Gln Arg Lys Leu Ser Asn Gly Pro Val Phe Arg Val
                610                 615                 620
Met Gly Gln Phe Leu Gly Tyr Pro Ser Leu Ile Glu Arg Thr His Glu
625                 630                 635                 640
Phe Phe Glu Lys Ser Leu Ile Tyr Tyr Asn Gly Arg Pro Asp Leu Met
                645                 650                 655
Arg Val His Asn Asn Thr Leu Ile Asn Ser Thr Ser Gln Arg Val Cys
                660                 665                 670
Trp Gln Gly Gln Glu Gly Gly Leu Glu Gly Leu Arg Gln Lys Gly Trp
                675                 680                 685
Ser Ile Leu Asn Leu Leu Val Ile Gln Arg Glu Ala Lys Ile Arg Asn
                690                 695                 700
Thr Ala Val Lys Val Leu Ala Gln Gly Asp Asn Gln Val Ile Cys Thr
705                 710                 715                 720
Gln Tyr Lys Thr Lys Lys Ser Arg Asn Val Val Glu Leu Gln Gly Ala
                725                 730                 735
Leu Asn Gln Met Val Ser Asn Asn Glu Lys Ile Met Thr Ala Ile Lys
                740                 745                 750
```

```
Ile Gly Thr Gly Lys Leu Gly Leu Leu Ile Asn Asp Asp Glu Thr Met
            755                 760                 765

Gln Ser Ala Asp Tyr Leu Asn Tyr Gly Lys Ile Pro Ile Phe Arg Gly
    770                 775                 780

Val Ile Arg Gly Leu Glu Thr Lys Arg Trp Ser Arg Val Thr Cys Val
785                 790                 795                 800

Thr Asn Asp Gln Ile Pro Thr Cys Ala Asn Ile Met Ser Ser Val Ser
                805                 810                 815

Thr Asn Ala Leu Thr Val Ala His Phe Ala Glu Asn Pro Ile Asn Ala
            820                 825                 830

Met Ile Gln Tyr Asn Tyr Phe Gly Thr Phe Ala Arg Leu Leu Leu Met
            835                 840                 845

Met His Asp Pro Ala Leu Arg Gln Ser Leu Tyr Glu Val Gln Asp Lys
    850                 855                 860

Ile Pro Gly Leu His Ser Ser Thr Phe Lys Tyr Ala Met Leu Tyr Leu
865                 870                 875                 880

Asp Pro Ser Ile Gly Gly Val Ser Gly Met Ser Leu Ser Arg Phe Leu
                885                 890                 895

Ile Arg Ala Phe Pro Asp Pro Val Thr Glu Ser Leu Ser Phe Trp Arg
            900                 905                 910

Phe Ile His Val His Ala Arg Ser Glu His Leu Lys Glu Met Ser Ala
            915                 920                 925

Val Phe Gly Asn Pro Glu Ile Ala Lys Phe Arg Ile Thr His Ile Asp
    930                 935                 940

Lys Leu Val Glu Asp Pro Thr Ser Leu Asn Ile Ala Met Gly Met Ser
945                 950                 955                 960

Pro Ala Asn Leu Leu Lys Thr Glu Val Lys Lys Cys Leu Ile Glu Ser
                965                 970                 975

Arg Gln Thr Ile Arg Asn Gln Val Ile Lys Asp Ala Thr Ile Tyr Leu
            980                 985                 990

Tyr His Glu Glu Asp Arg Leu Arg Ser Phe Leu Trp Ser Ile Asn Pro
    995                 1000                1005

Leu Phe Pro Arg Phe Leu Ser Glu Phe Lys Ser Gly Thr Phe Leu Gly
    1010                1015                1020

Val Ala Asp Gly Leu Ile Ser Leu Phe Gln Asn Ser Arg Thr Ile Arg
1025                1030                1035                1040

Asn Ser Phe Lys Lys Lys Tyr His Arg Glu Leu Asp Asp Leu Ile Val
                1045                1050                1055

Arg Ser Glu Val Ser Ser Leu Thr His Leu Gly Lys Leu His Leu Arg
            1060                1065                1070

Arg Gly Ser Cys Lys Met Trp Thr Cys Ser Ala Thr His Ala Asp Thr
            1075                1080                1085

Leu Arg Tyr Lys Ser Trp Gly Arg Thr Val Ile Gly Thr Thr Val Pro
    1090                1095                1100

His Pro Leu Glu Met Leu Gly Pro Gln His Arg Lys Glu Thr Pro Cys
1105                1110                1115                1120

Ala Pro Cys Asn Thr Ser Gly Phe Asn Tyr Val Ser Val His Cys Pro
                1125                1130                1135

Asp Gly Ile His Asp Val Phe Ser Ser Arg Gly Pro Leu Pro Ala Tyr
            1140                1145                1150

Leu Gly Ser Lys Thr Ser Glu Ser Thr Ser Ile Leu Gln Pro Trp Glu
            1155                1160                1165
```

```
Arg Glu Ser Lys Val Pro Leu Ile Lys Arg Ala Thr Arg Leu Arg Asp
    1170                1175                1180

Ala Ile Ser Trp Phe Val Glu Pro Asp Ser Lys Leu Ala Met Thr Ile
1185                1190                1195                1200

Leu Ser Asn Ile His Ser Leu Thr Gly Glu Glu Trp Thr Lys Arg Gln
            1205                1210                1215

His Gly Phe Lys Arg Thr Gly Ser Ala Leu His Arg Phe Ser Thr Ser
        1220                1225                1230

Arg Met Ser His Gly Gly Phe Ala Ser Gln Ser Thr Ala Ala Leu Thr
    1235                1240                1245

Arg Leu Met Ala Thr Thr Asp Thr Met Arg Asp Leu Gly Asp Gln Asn
1250                1255                1260

Phe Asp Phe Leu Phe Gln Ala Thr Leu Leu Tyr Ala Gln Ile Thr Thr
1265                1270                1275                1280

Thr Val Ala Arg Asp Gly Trp Ile Thr Ser Cys Thr Asp His Tyr His
            1285                1290                1295

Ile Ala Cys Lys Ser Cys Leu Arg Pro Ile Glu Glu Ile Thr Leu Asp
        1300                1305                1310

Ser Ser Met Asp Tyr Thr Pro Pro Asp Val Ser His Val Leu Lys Thr
    1315                1320                1325

Trp Arg Asn Gly Glu Gly Ser Trp Gly Gln Glu Ile Lys Gln Ile Tyr
1330                1335                1340

Pro Leu Glu Gly Asn Trp Lys Asn Leu Ala Pro Ala Glu Gln Ser Tyr
1345                1350                1355                1360

Gln Val Gly Arg Cys Ile Gly Phe Leu Tyr Gly Asp Leu Ala Tyr Arg
            1365                1370                1375

Lys Ser Thr His Ala Glu Asp Ser Ser Leu Phe Pro Leu Ser Ile Gln
        1380                1385                1390

Gly Arg Ile Arg Gly Arg Gly Phe Leu Lys Gly Leu Leu Asp Gly Leu
    1395                1400                1405

Met Arg Ala Ser Cys Cys Gln Val Ile His Arg Ser Leu Ala His
1410                1415                1420

Leu Lys Arg Pro Ala Asn Ala Val Tyr Gly Gly Leu Ile Tyr Leu Ile
1425                1430                1435                1440

Asp Lys Leu Ser Val Ser Pro Pro Phe Leu Ser Leu Thr Arg Ser Gly
            1445                1450                1455

Pro Ile Arg Asp Glu Leu Glu Thr Ile Pro His Lys Ile Pro Thr Ser
        1460                1465                1470

Tyr Pro Thr Ser Asn Arg Asp Met Gly Val Ile Val Arg Asn Tyr Phe
    1475                1480                1485

Lys Tyr Gln Cys Arg Leu Ile Glu Lys Gly Lys Tyr Arg Ser His Tyr
1490                1495                1500

Ser Gln Leu Trp Leu Phe Ser Asp Val Leu Ser Ile Asp Phe Ile Gly
1505                1510                1515                1520

Pro Phe Ser Ile Ser Thr Thr Leu Leu Gln Ile Leu Tyr Lys Pro Phe
            1525                1530                1535

Leu Ser Gly Lys Asp Lys Asn Glu Leu Arg Glu Leu Ala Asn Leu Ser
        1540                1545                1550

Ser Leu Leu Arg Ser Gly Glu Gly Trp Glu Asp Ile His Val Lys Phe
    1555                1560                1565

Phe Thr Lys Asp Ile Leu Leu Cys Pro Glu Glu Ile Arg His Ala Cys
1570                1575                1580

Lys Phe Gly Ile Ala Lys Asp Asn Asn Lys Asp Met Ser Tyr Pro Pro
```

```
                1585                1590                1595                1600
Trp Gly Arg Glu Ser Arg Gly Thr Ile Thr Thr Ile Pro Val Tyr Tyr
                    1605                1610                1615

Thr Thr Thr Pro Tyr Pro Lys Met Leu Glu Met Pro Arg Ile Gln
    1620                1625                1630

Asn Pro Leu Leu Ser Gly Ile Arg Leu Gly Gln Leu Pro Thr Gly Ala
        1635                1640                1645

His Tyr Lys Ile Arg Ser Ile Leu His Gly Met Gly Ile His Tyr Arg
    1650                1655                1660

Asp Phe Leu Ser Cys Gly Asp Gly Ser Gly Gly Met Thr Ala Ala Leu
1665                1670                1675                1680

Leu Arg Glu Asn Val His Ser Arg Gly Ile Phe Asn Ser Leu Leu Glu
            1685                1690                1695

Leu Ser Gly Ser Val Met Arg Gly Ala Ser Pro Glu Pro Pro Ser Ala
                1700                1705                1710

Leu Glu Thr Leu Gly Gly Asp Lys Ser Arg Cys Val Asn Gly Glu Thr
            1715                1720                1725

Cys Trp Glu Tyr Pro Ser Asp Leu Cys Asp Pro Arg Thr Trp Asp Tyr
        1730                1735                1740

Phe Leu Arg Leu Lys Ala Gly Leu Gly Leu Gln Ile Asp Leu Ile Val
1745                1750                1755                1760

Met Asp Met Glu Val Arg Asp Ser Ser Thr Ser Leu Lys Ile Glu Thr
                1765                1770                1775

Asn Val Arg Asn Tyr Val His Arg Ile Leu Asp Glu Gln Gly Val Leu
            1780                1785                1790

Ile Tyr Lys Thr Tyr Gly Thr Tyr Ile Cys Glu Ser Glu Lys Asn Ala
        1795                1800                1805

Val Thr Ile Leu Gly Pro Met Phe Lys Thr Val Asp Leu Val Gln Thr
    1810                1815                1820

Glu Phe Ser Ser Gln Thr Ser Glu Val Tyr Met Val Cys Lys Gly
1825                1830                1835                1840

Leu Lys Lys Leu Ile Asp Glu Pro Asn Pro Asp Trp Ser Ser Ile Asn
                1845                1850                1855

Glu Ser Trp Lys Asn Leu Tyr Ala Phe Gln Ser Ser Glu Gln Glu Phe
        1860                1865                1870

Ala Arg Ala Lys Lys Val Ser Thr Tyr Phe Thr Leu Thr Gly Ile Pro
            1875                1880                1885

Ser Gln Phe Ile Pro Asp Pro Phe Val Asn Ile Glu Thr Met Leu Gln
    1890                1895                1900

Ile Phe Gly Val Pro Thr Gly Val Ser His Ala Ala Ala Leu Lys Ser
1905                1910                1915                1920

Ser Asp Arg Pro Ala Asp Leu Leu Thr Ile Ser Leu Phe Tyr Met Ala
                1925                1930                1935

Ile Ile Ser Tyr Tyr Asn Ile Asn His Ile Arg Val Gly Pro Ile Pro
            1940                1945                1950

Pro Asn Pro Pro Ser Asp Gly Ile Ala Gln Asn Val Gly Ile Ala Ile
        1955                1960                1965

Thr Gly Ile Ser Phe Trp Leu Ser Leu Met Glu Lys Asp Ile Pro Leu
    1970                1975                1980

Tyr Gln Gln Cys Leu Ala Val Ile Gln Gln Ser Phe Pro Ile Arg Trp
1985                1990                1995                2000

Glu Ala Val Ser Val Lys Gly Gly Tyr Lys Gln Lys Trp Ser Thr Arg
                2005                2010                2015
```

Gly Asp Gly Leu Pro Lys Asp Thr Arg Ile Ser Asp Ser Leu Ala Pro
            2020                2025                2030

Ile Gly Asn Trp Ile Arg Ser Leu Glu Leu Val Arg Asn Gln Val Arg
            2035                2040                2045

Leu Asn Pro Phe Asn Glu Ile Leu Phe Asn Gln Leu Cys Arg Thr Val
            2050                2055                2060

Asp Asn His Leu Lys Trp Ser Asn Leu Arg Arg Asn Thr Gly Met Ile
2065                2070                2075                2080

Glu Trp Ile Asn Arg Arg Ile Ser Lys Glu Asp Arg Ser Ile Leu Met
                2085                2090                2095

Leu Lys Ser Asp Leu His Glu Glu Asn Ser Trp Arg Asp
            2100                2105

<210> SEQ ID NO 10
<211> LENGTH: 229
<212> TYPE: PRT
<213> ORGANISM: Vesicular stomatitis virus

<400> SEQUENCE: 10

Met Ser Ser Leu Lys Lys Ile Leu Gly Leu Lys Gly Lys Gly Lys Lys
1               5                   10                  15

Ser Lys Lys Leu Gly Ile Ala Pro Pro Tyr Glu Glu Asp Thr Ser
            20                  25                  30

Met Glu Tyr Ala Pro Ser Ala Pro Ile Asp Lys Ser Tyr Phe Gly Val
        35                  40                  45

Asp Glu Met Asp Thr Tyr Asp Pro Asn Gln Leu Arg Tyr Glu Lys Phe
50                  55                  60

Phe Phe Thr Val Lys Met Thr Val Arg Ser Asn Arg Pro Phe Arg Thr
65                  70                  75                  80

Tyr Ser Asp Val Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
            115                 120                 125

Pro Glu Tyr His Ala His Cys Glu Gly Arg Ala Tyr Leu Pro His Arg
        130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
        195                 200                 205

Gly Leu Ile Val Glu Lys Lys Ala Ser Gly Ala Trp Val Leu Asp Ser
    210                 215                 220

Ile Gly His Phe Lys
225

<210> SEQ ID NO 11
<211> LENGTH: 498
<212> TYPE: PRT
<213> ORGANISM: Lymphocytic choriomeningitis mammarenavirus

<400> SEQUENCE: 11

```
Met Gly Gln Ile Val Thr Met Phe Glu Ala Leu Pro His Ile Ile Asp
1               5                   10                  15

Glu Val Ile Asn Ile Val Ile Val Leu Ile Ile Thr Ser Ile
                20              25              30

Lys Ala Val Tyr Asn Phe Ala Thr Cys Gly Ile Leu Ala Leu Val Ser
            35              40                  45

Phe Leu Phe Leu Ala Gly Arg Ser Cys Gly Met Tyr Gly Leu Asn Gly
        50              55              60

Pro Asp Ile Tyr Lys Gly Val Tyr Gln Phe Lys Ser Val Glu Phe Asp
65              70              75              80

Met Ser His Leu Asn Leu Thr Met Pro Asn Ala Cys Ser Ala Asn Asn
                85                  90                  95

Ser His His Tyr Ile Ser Met Gly Ser Ser Gly Leu Glu Leu Thr Phe
                100                 105                 110

Thr Asn Asp Ser Ile Leu Asn His Asn Phe Cys Asn Leu Thr Ser Ala
            115                 120                 125

Phe Asn Lys Lys Thr Phe Asp His Thr Leu Met Ser Ile Val Ser Ser
        130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Ile Ser Gln Cys Arg Thr Phe Arg Gly Arg Val Leu
                180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
        210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
        275                 280                 285

Trp Met Ile Leu Ala Ala Glu Leu Lys Cys Phe Gly Asn Thr Ala Val
        290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
            340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
                405                 410                 415
```

```
Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg

<210> SEQ ID NO 12
<211> LENGTH: 498
<212> TYPE: PRT
<213> ORGANISM: Dandenong virus

<400> SEQUENCE: 12

Met Gly Gln Leu Ile Thr Met Phe Glu Ala Leu Pro His Ile Ile Asp
1               5                   10                  15

Glu Val Ile Asn Ile Val Ile Val Leu Val Ile Ile Thr Ser Ile
            20                  25                  30

Lys Ala Val Tyr Asn Phe Ala Thr Cys Gly Ile Ile Ala Leu Ile Ser
        35                  40                  45

Phe Cys Leu Leu Ala Gly Arg Ser Cys Gly Leu Tyr Gly Val Thr Gly
    50                  55                  60

Pro Asp Ile Tyr Lys Gly Leu Tyr Gln Phe Lys Ser Val Glu Phe Asn
65                  70                  75                  80

Met Ser Gln Leu Asn Leu Thr Met Pro Asn Ala Cys Ser Ala Asn Asn
                85                  90                  95

Ser His His Tyr Ile Ser Met Gly Lys Ser Gly Leu Glu Leu Thr Phe
            100                 105                 110

Thr Asn Asp Ser Ile Ile Ser His Asn Phe Cys Asn Leu Thr Asp Gly
        115                 120                 125

Phe Lys Lys Lys Thr Phe Asp His Thr Leu Met Ser Ile Val Ala Ser
    130                 135                 140

Leu His Leu Ser Ile Arg Gly Asn Thr Asn Tyr Lys Ala Val Ser Cys
145                 150                 155                 160

Asp Phe Asn Asn Gly Ile Thr Ile Gln Tyr Asn Leu Ser Phe Ser Asp
                165                 170                 175

Ala Gln Ser Ala Ile Asn Gln Cys Arg Thr Phe Arg Gly Arg Val Leu
            180                 185                 190

Asp Met Phe Arg Thr Ala Phe Gly Gly Lys Tyr Met Arg Ser Gly Tyr
        195                 200                 205

Gly Trp Lys Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Glu
225                 230                 235                 240

Tyr Ala Gly Pro Phe Gly Leu Ser Arg Val Leu Phe Ala Gln Glu Lys
                245                 250                 255

Thr Lys Phe Leu Thr Arg Arg Leu Ala Gly Thr Phe Thr Trp Thr Leu
            260                 265                 270

Ser Asp Ser Ser Gly Thr Glu Asn Pro Gly Gly Tyr Cys Leu Thr Lys
        275                 280                 285
```

```
Trp Met Leu Ile Ala Ala Glu Leu Lys Cys Phe Gly Asn Thr Ala Val
    290                 295                 300
Ala Lys Cys Asn Ile Asn His Asp Glu Glu Phe Cys Asp Met Leu Arg
305                 310                 315                 320
Leu Ile Asp Tyr Asn Lys Ala Ala Leu Lys Lys Phe Lys Glu Asp Val
                325                 330                 335
Glu Ser Ala Leu His Leu Phe Lys Thr Thr Val Asn Ser Leu Ile Ser
            340                 345                 350
Asp Gln Leu Leu Met Arg Asn His Leu Arg Asp Leu Met Gly Val Pro
        355                 360                 365
Tyr Cys Asn Tyr Ser Lys Phe Trp Tyr Leu Glu His Val Lys Thr Gly
    370                 375                 380
Asp Thr Ser Val Pro Lys Cys Trp Leu Val Ser Asn Gly Ser Tyr Leu
385                 390                 395                 400
Asn Glu Thr His Phe Ser Asp Gln Ile Glu Gln Ala Asp Asn Met
                405                 410                 415
Ile Thr Glu Met Leu Arg Lys Asp Tyr Ile Lys Arg Gln Gly Ser Thr
            420                 425                 430
Pro Leu Ala Leu Met Asp Leu Leu Met Phe Ser Thr Ser Ala Tyr Leu
        435                 440                 445
Ile Ser Val Phe Leu His Leu Met Lys Ile Pro Thr His Arg His Ile
    450                 455                 460
Lys Gly Gly Thr Cys Pro Lys Pro His Arg Leu Thr Ser Lys Gly Ile
465                 470                 475                 480
Cys Ser Cys Gly Ala Phe Lys Val Pro Gly Val Lys Thr Val Trp Lys
                485                 490                 495
Arg Arg

<210> SEQ ID NO 13
<211> LENGTH: 489
<212> TYPE: PRT
<213> ORGANISM: Mopeia mammarenavirus

<400> SEQUENCE: 13

Met Gly Gln Ile Val Thr Phe Phe Gln Glu Val Pro His Ile Leu Glu
1               5                   10                  15
Glu Val Met Asn Ile Val Leu Met Thr Leu Ser Ile Leu Ala Ile Leu
                20                  25                  30
Lys Gly Ile Tyr Asn Val Met Thr Cys Gly Ile Ile Gly Leu Ile Thr
            35                  40                  45
Phe Leu Phe Leu Cys Gly Arg Ser Cys Ser Ser Ile Tyr Lys Asp Asn
        50                  55                  60
Tyr Glu Phe Phe Ser Leu Asp Leu Asp Met Ser Ser Leu Asn Ala Thr
65                  70                  75                  80
Met Pro Leu Ser Cys Ser Lys Asn Asn Ser His His Tyr Ile Gln Val
                85                  90                  95
Gly Asn Glu Thr Gly Leu Glu Leu Thr Leu Thr Asn Thr Ser Ile Ile
                100                 105                 110
Asp His Lys Phe Cys Asn Leu Ser Asp Ala His Arg Arg Asn Leu Tyr
            115                 120                 125
Asp Lys Ala Leu Met Ser Ile Leu Thr Thr Phe His Leu Ser Ile Pro
        130                 135                 140
Asp Phe Asn Gln Tyr Glu Ala Met Ser Cys Asp Phe Asn Gly Gly Lys
145                 150                 155                 160
```

```
Ile Ser Ile Gln Tyr Asn Leu Ser His Ser Asn Tyr Val Asp Ala Gly
                165                 170                 175

Asn His Cys Gly Thr Ile Ala Asn Gly Ile Met Asp Val Phe Arg Arg
            180                 185                 190

Met Tyr Trp Ser Thr Ser Leu Ser Val Ala Ser Asp Ile Ser Gly Thr
        195                 200                 205

Gln Cys Ile Gln Thr Asp Tyr Lys Tyr Leu Ile Ile Gln Asn Thr Ser
    210                 215                 220

Trp Glu Asp His Cys Met Phe Ser Arg Pro Ser Pro Met Gly Phe Leu
225                 230                 235                 240

Ser Leu Leu Ser Gln Arg Thr Arg Asn Phe Tyr Ile Ser Arg Arg Leu
                245                 250                 255

Leu Gly Leu Phe Thr Trp Thr Leu Ser Asp Ser Glu Gly Asn Asp Met
            260                 265                 270

Pro Gly Gly Tyr Cys Leu Thr Arg Ser Met Leu Ile Gly Leu Asp Leu
        275                 280                 285

Lys Cys Phe Gly Asn Thr Ala Ile Ala Lys Cys Asn Gln Ala His Asp
    290                 295                 300

Glu Glu Phe Cys Asp Met Leu Arg Leu Phe Asp Phe Asn Lys Gln Ala
305                 310                 315                 320

Ile Ser Lys Leu Arg Ser Glu Val Gln Gln Ser Ile Asn Leu Ile Asn
                325                 330                 335

Lys Ala Val Asn Ala Leu Ile Asn Asp Gln Leu Val Met Arg Asn His
            340                 345                 350

Leu Arg Asp Leu Met Gly Ile Pro Tyr Cys Asn Tyr Ser Lys Phe Trp
        355                 360                 365

Tyr Leu Asn Asp Thr Arg Thr Gly Arg Thr Ser Leu Pro Lys Cys Trp
    370                 375                 380

Leu Val Thr Asn Gly Ser Tyr Leu Asn Glu Thr Gln Phe Ser Thr Glu
385                 390                 395                 400

Ile Glu Gln Glu Ala Asn Asn Met Phe Thr Asp Met Leu Arg Lys Glu
                405                 410                 415

Tyr Glu Lys Arg Gln Ser Thr Thr Pro Leu Gly Leu Val Asp Leu Phe
            420                 425                 430

Val Phe Ser Thr Ser Phe Tyr Leu Ile Ser Val Phe Leu His Leu Ile
        435                 440                 445

Lys Ile Pro Thr His Arg His Ile Lys Gly Lys Pro Cys Pro Lys Pro
    450                 455                 460

His Arg Leu Asn His Met Ala Ile Cys Ser Cys Gly Phe Tyr Lys Gln
465                 470                 475                 480

Pro Gly Leu Pro Thr Gln Trp Lys Arg
                485

<210> SEQ ID NO 14
<211> LENGTH: 446
<212> TYPE: PRT
<213> ORGANISM: Homo sapiens

<400> SEQUENCE: 14

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ala Ser
                20                  25                  30

Ala Met Ser Trp Val Arg Gln Ala Pro Gly Lys Gly Leu Glu Trp Val
            35                  40                  45
```

```
Ala Tyr Ile Ser Gly Gly Gly Asp Thr Tyr Tyr Ser Ser Ser Val
            50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                85                  90                  95
Ala Arg His Ser Asn Val Asn Tyr Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Cys Ser Arg Ser Thr Ser Glu Ser Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
            195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
                260                 265                 270
Val Gln Phe Asn Trp Tyr Val Asp Gly Val Glu Val His Asn Ala Lys
            275                 280                 285
Thr Lys Pro Arg Glu Glu Gln Phe Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly
            435                 440                 445

<210> SEQ ID NO 15
<211> LENGTH: 218
```

```
<212> TYPE: PRT
<213> ORGANISM: Homo sapiens

<400> SEQUENCE: 15

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 16
<211> LENGTH: 446
<212> TYPE: PRT
<213> ORGANISM: Homo sapiens

<400> SEQUENCE: 16

Glu Val Met Leu Val Glu Ser Gly Gly Leu Val Gln Pro Gly Gly
1               5                   10                  15

Ser Leu Arg Leu Ser Cys Thr Ala Ser Gly Phe Thr Phe Ser Ala Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Pro Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
                435                 440                 445

<210> SEQ ID NO 17
<211> LENGTH: 218
<212> TYPE: PRT
<213> ORGANISM: Homo sapiens

<400> SEQUENCE: 17

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Thr Ser
                20                  25                  30

Gly Ile Ser Phe Met Asn Trp Tyr Gln Gln Lys Pro Gly Gln Ala Pro
                35                  40                  45

Lys Leu Leu Ile Tyr Val Ala Ser Asn Gln Gly Ser Gly Ile Pro Ala
50                  55                  60
```

```
Arg Phe Ser Gly Ser Gly Ser Gly Thr Asp Phe Thr Leu Thr Ile Ser
 65                  70                  75                  80

Arg Leu Glu Pro Glu Asp Phe Ala Val Tyr Tyr Cys Gln Gln Ser Lys
                 85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 18
<211> LENGTH: 446
<212> TYPE: PRT
<213> ORGANISM: Homo sapiens

<400> SEQUENCE: 18

```
Glu Val Met Leu Val Glu Ser Gly Gly Gly Leu Val Gln Pro Gly Gly
  1               5                  10                  15

Ser Leu Arg Leu Ser Cys Thr Ala Ser Gly Phe Thr Phe Ser Lys Ser
             20                  25                  30

Ala Met Ser Trp Val Arg Gln Ala Pro Gly Lys Gly Leu Glu Trp Val
         35                  40                  45

Ala Tyr Ile Ser Gly Gly Gly Asp Thr Tyr Tyr Ser Ser Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
```

```
            210                 215                 220
Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
                435                 440                 445

<210> SEQ ID NO 19
<211> LENGTH: 218
<212> TYPE: PRT
<213> ORGANISM: Homo sapiens

<400> SEQUENCE: 19

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140
```

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 20
<211> LENGTH: 446
<212> TYPE: PRT
<213> ORGANISM: Homo sapiens

<400> SEQUENCE: 20

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
            35                  40                  45

Ala Tyr Ile Ser Gly Gly Gly Asp Thr Tyr Tyr Ser Ser Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300
```

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 21
<211> LENGTH: 218
<212> TYPE: PRT
<213> ORGANISM: Homo sapiens

<400> SEQUENCE: 21

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 22
<211> LENGTH: 446
<212> TYPE: PRT
<213> ORGANISM: Homo sapiens

<400> SEQUENCE: 22

Glu Val Met Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Lys Ser
            20                  25                  30

Ala Met Ser Trp Val Arg Gln Ala Pro Gly Lys Gly Leu Glu Trp Val
        35                  40                  45

Ala Tyr Ile Ser Gly Gly Gly Asp Thr Tyr Tyr Ser Ser Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ser Asn Val Asn Tyr Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445

<210> SEQ ID NO 23
<211> LENGTH: 218
<212> TYPE: PRT
<213> ORGANISM: Homo sapiens

<400> SEQUENCE: 23

Glu Ile Val Leu Thr Gln Ser Pro Ala Thr Leu Ser Leu Ser Pro Gly
1               5                   10                  15

Glu Arg Ala Thr Met Ser Cys Arg Ala Ser Glu Asn Ile Asp Val Ser
            20                  25                  30

Gly Ile Ser Phe Met Asn Trp Tyr Gln Gln Lys Pro Gly Gln Ala Pro
        35                  40                  45

Lys Leu Leu Ile Tyr Val Ala Ser Asn Gln Gly Ser Gly Ile Pro Ala
50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln Gln Ser Lys
                85                  90                  95

Glu Val Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 24
<211> LENGTH: 11520
<212> TYPE: RNA
<213> ORGANISM: Vesicular stomatitis virus

<400> SEQUENCE: 24
ugcuucuguu uguuggguaa uaauaguaau uuuccgaguc cucuuugaaa uugucauuag      60
uuuuacagac aaugucaguu ucuuaguaaa cuguugugue agcaucaagg uuuugaagga    120
cguuuacucc uaggucaccu uaugggccgu cuaaugaagu cuuuuagauu cucuaagga    180 gaaauguagu uaugaguuu ucaaacagu cuagauucuc cuauacagau ggauuccggag    240 uuuaggccuu uacauaguua guauguacag uugucgauga acauaccucg uaauuuccug    300

```
uaggccccau ucaaccuauu ucuaaccagu ucaaagccuu auuuguagcc cuuucguccc    360
cuauguuagc cuuauaaacu ggaacauagg aacuuucggg accugccgca ugaaggucua    420
ccucauagcc uacgaagguc uuggucgcgu cuacuguuua ccaacggaaa cauagaugaa    480
ccgaauaugu cucacccguc uuguguuuac ggacuuaugu cuuuuucga guaccaccc     540
gacuguuuag uuacguuuua cuaguuacuu gucaaacuug gagaacacgg ucuuccagca    600
cuguaaaaac uacacacccc uuuacuguca uuaaugugu uuuaacagcg acgucaccug    660
uacaagaagg uguacaaguu uuuguacuu acacggagca agucuaugcc uugauaacaa    720
aggucuaagu uucuaacacg acguaaccgu uguaaaccug uggagacguu uuauuggccu    780
uacagauguc uucuacauug cuggaccuag aacuggcuc uucaacgucu acuuuaccag    840
guuuacuacg aagguccggu ucuuuaacug uccggcuaa guauguacgg aauaaacuag    900
cugaaaaccua acagaagauu cagagguaua agaaggcagu uuugggacg aaggugaag    960
accccccguua acgucgaga agacgagucu aggugguccuc guuccuuacg ggcugucgga   1020
cuacuguaac ucauauguag agaaugaugu cguccaaaca acaugcgaau acgucauccu   1080
aggagacggc ugaaccgugu ugucaaaaca caaccucuau uguuuaugug aggucuacua   1140
ucauggccuc cuaacugcug auuacguggc ggguguccgu cucuacacca gcuuaccgag   1200
ccuaccaaac uucuaguuuu gucuuuuggc ugaggacuau acuacgucau acgcuuuucu   1260
cgucaguaca gugacguucc ggauucucuc uucuguuaac cguucauacg auucagucuu   1320
aaacuguuua cugggauauu aagagucuag uggauaauau auaauacgau guauacuuuu   1380
uuugauuguc uauaguaccu auuagagugu uuucaagcac ucauagaguu caggauaaga   1440
gcagaccuag uccgccaucc ucucuaucua cucuagcuuc guguugcucg acuuuucagg   1500
uuaauacuca acaagguucu ccaccucac cuuucucguau gauucgggag aauaaaaguc    1560
cgucgucuac uaagacgugu ucuuagacuu ggucuuuaac uucuguuagu ccgaacaua    1620
cguggucuag gucuucgacu cguucaacuu ccgaaauaug uccccggaaa ucuacugaua   1680
cgucuacucc uucaccuaca acauaaauga agccugaccu uugucggacu cgaacuuaga   1740
cugcucguac cuuucuggaa ugccaacugu agcggcuccc caaauucacc ucucgucuuu   1800
agggucaccg aaagcugcua auuucgucag cacguuucac gguuuaugac cuuagaccgu   1860
cucacgugua aacuucguag ccccucuccc caguaauacu uccucgcggu cuauugaggc   1920
cuacauauau uccagugagg ucacuacuug uguaggca gggguuagucu cgucauagu     1980
cuacaaacca gagagauuu cuguaggauc ugaaagguug gguucuuucg uucagaaguc   2040
ggagaguggu auaggaaccu acuaacaag aguagauccu cucucaagua gagacagccu    2100
ccacugccug cuuacagagu auuucccgg uaggacgagc cggacucuau uguuuucaac   2160
auguuagucc gcucucaguu uauaagagac aucgauacu uuuuucauu gucuauagug    2220
cuagauucac aauagggua gguaaguagu acucaaggaa uucuucuaa gagccagacu    2280
ucccuuuccc auucuuuaga uucuuuaauc ccuagcgugg uggggaaua cuucuccugu    2340
gaucguaccu cauacgaggc ucgcgagguu aacuguuuag gauaaaaccu caacugcucu   2400
accuguggau acuaggcuua guuaauucua uacucuuuaa gaagaaagu cacuuuuacu     2460
gccaaucuag auuagcaggc aagucuugua ugagcuaca ccgucggcga cauagggua      2520
cccuagugua caugagccu uaccguccc ugcagggaa gauguuuag aaccgaaaaa       2580
acccaagaag auuagauuuc cggugaggu cgccauaaccg ucuaguucca guugucuca    2640
```

-continued

```
uagugcgagu gacgcuuccg ucccgaauaa acguguauc cuaccccuuc uggggagggu      2700
acgaguuaca uggucucgug aagucuucug guaaguuaua uccagaaaug uucccuugcu     2760
aacucgagug uuacugguag augcuacuac ucagugaccu ucgucgagga uacuagaccc     2820
uaguaaaguu aagaagguuu aaaagacuaa agucucucuu ccggaauuac aaaccggacu     2880
aacagcucuu uuuccguaga ccucgcaccc aggaccugag auagccggug aaguuuacuc     2940
gaucagauug aagaucgaag acuuguuagg ggccaaauga gucagagggg auuaaggucg     3000
gagagcuugu ugauuauagg acagaaaaga uagggauacu uuuuugauu gucucuagcu      3060 agacaaaugc gcagugccua gggggcccga cguccuuaag cgguggguacc cggucuagca    3120 cugguacaag cuccgggacg ggguguagua gcugcuccac uaguuguagc acuauagca     3180 cgauaguag uagguggucgu aguuccggca cauguugaag cgguggacgc cguaggaccg    3240
ggaccacucg aaggacaagg accggccguc uucgacgccg uacaugccgg acuuaccggg    3300
gcuauagaug uucccgcaca uggucaaguu cucgcaccuc aagcuguacu cgguggacuu    3360 ggaguggguac ggguugcgga cgucgcgguu guuaucgggug ugaugagu cguaccccguc   3420 gucgccggac cucaacugga aguuguugcu gucguaggac ugggguguuga agacguugga   3480 guggucgcgg aaguuguucu uuuggaagcu ggugugggag uacucguagc acucgucgga    3540
cguggacucg uagucccgu ugucguuggu guuccggcac ucgacgcuga aguuguugcc     3600 guaguggguag ucauguuugg acucgaaguc gcuaggaguc ucgcgguagu cggucacguc    3660
uuggaagucu ccgucucacg accuguacaa gucuuggcgg aagccgccgu ucauguacuc    3720
uucgccgacc ccgacccggc cgucgcugcc guucgguggg accacgucgg ucggucgau     3780 ggucauggag uaguaggucu ugucuuggac ccucuuggug acgucauauc ggccuggaaa    3840
gccguacucg ucuuaggaca agcggguccu cuuuggguuc aaggagugguu ccucugaccg    3900 gccguggaag uggaccugggg acucgcuguc gucgccgcac cucuuggggac cgccgaugac    3960 ggaguggguuc accauacugg accggcggcu cgacuucacg aagccguugu ggcggcaccg    4020
guucacguug cacuggugugc ugcuccucaa gacgcuguac gacucugagu agcugauguu    4080
guuccggcgg gacucguuca aguucgguccu gcaccucucg cgggacgugc acaaguucug    4140
guggcacuug ucgaguagu cgcuggucga cgaguacucu uggugugguacu cucuggaguu    4200 cccgcacggg augacguuga ugucguucaa gaccauagac cucgugcggu ucuggccgcu    4260
cuggucgcac ggguucacga ccgaccacug guuaccgucg auggacuugc ucugggugaa    4320
gucgcugguc uagcucgucc uucggcuguu guacuagugg cucuacgacu ccuuccugau    4380
guaguucucu gucccgucgu gggggaccg ggaguaccua gacgaguaca agucgugguc     4440
gcggauggag uagucguaga aggacguggga ccacuucuag ggguggugu cuguguaguu    4500 cccgccgucg acggguucg ggguggucuga gugguuguuc ccguagacgu cgacgccgcg    4560
gaaguuccac gggccgcacu uuugguagac cuucuccucu auccgccggc gaugcuggag    4620
cugauacuuu uuuugauugu cuauaggagc ugcgguggua cccgaccagg acguaguaag    4680
acaaagacca ccggugucgg uggccacagg uaucaagacu accgccgcga guccugacga    4740
cggacuucau gagagucucu uucuaggggc gguuccagca cgccucgaug ucuuucguuc    4800
ucggaagaga cccgacgaga uagggacggu aggacaaaga cggggccuuc ucuaguguc     4860 ggcuugacac gcggcuagga uuucuugaca cccacgucgu cgacuacguc guagaccugu    4920
ucugggguag aggagucuuc ggacgaguuc cgacuacuaa aaauaugauc ggucuaagaa    4980
guacaaaccu gguuuaguug aacacuaugg uacgaguuuc uccggaguua auauaaacuc    5040
```

```
aaaaauuaaa aauacuuuuu uugauugucg uuaguaccuu caggugcuaa aacucuggcu    5100
gcucaaguua cuaaaguuac uucuacugau acgugeuucu cuuaaggacu uagggcuacu    5160
cgcguacugc augaacuuag uacgacuaau guuggacuua agaggagauu aaucacuacu    5220
auaacuguua aauuagaccu uuaaguuaag agaagguuaa gggagcuaca cccuaucauu    5280
cuugacccua ccucaagaac ucuacaauug caguacaguu cgguaggge agggeuguag    5340 agucuacgua uuuaccuacc cuucaaccaa uuacagacua uaguacuac ggucaguucc    5400 cauaucaaaa aauguacuuc accguuucu ccgucuuuau guaaacugc accaccucug    5460 gaaguaggcg ccgaccccgu uguuggua acuauguag uuuucccuuu cuaccugacu    5520
gaguaaguuu uaagagcgaa uaaacacagu uucaaaaac cugaaugugu caacuguaa    5580 uuagaauuua cgacagagac uccaccuuaa cgaguugaac cgcuccugaa aguuccguu    5640 ucagucuucu ucaagaguac cuugcuugua uacguccuaa ucccaagggu cgaacccagg    5700
augaaaauaa agucuuccua cccgaaugaa guucuuugaa cuauaagauu accuggcuuu    5760
gaaagacaau uaccaguuuc uacacuaaua ucccuccuac guuugccacg auagguacca    5820
uacaucuuau cuguuggaca agagucucgu ucuguagaag agggaagauu uauagauguc    5880
uuaaccucua uuuuaacacc ucccgucc uuuaaaaaga auacugaacu aauuuuacca    5940
ccuuggcuau acguugaacu ucgacuacuu uaaucguucu cuuaguucg gaaaucaggg    6000 uguuaaggga guaaaacuuu uaguauaguu cugaagacaa cuacuucccc guuuuuaacu    6060
ggcuccauau ucuaaggagg uacuagcuua uuacucacac uuuugucacc uagaguguga    6120
ccacuaaaua ccuagcaagu cuguaaccccc aguaggaaaa uaucuaauaa ugugaccuga    6180
ucuuuuuaau guaagguuc auugguacuu cuuucuauaa cuacacagua uacguuucg    6240 ugaacguuca cuaaaucgag ccuaacaaga uaaaguuguc aaguuacuag uauuuuucac    6300
caagcacuua ccucugaacg aggggagacu aguagggaa uuucaguac aauucuuuu     6360 auguaccggg ugucgacgag uucaaguucu aaaaccucua uuuaccguac uugaaggcga    6420
cuaauuuaca aaacuuuaug ggcugaauga ucugggcage uauuauauga gacuguuuc    6480 aguaaguuac uuaccaguc uccacaaccu uguacaggcu uacuuaggcu ugugaggaua    6540
gggaucauuu uuccacaacg ucugauacaa ccugeguuuc cgaugguuaa ccuucuuaa    6600 agaauuucuc uaacuacucu ucccgaaucu acuacuacua gauuaauaac cagaauuucc    6660
uuuccucucc cuugacuuca accguccauc uaaaagagg gauuacagaa ccuuuaacgc    6720
ucuuaugaaa cauuaauggc uuauaaacua uucugagua aagcagggau acaaauuucc    6780
ggacuguuac cgccugcuag auugacguca guaauuuuc uacaaucuaa ggaguaggcc    6840
gguuccuaac uucaguauac uccguuaaac guaucgguua guguaacuaa ugcuuuuac    6900 cuuauuggug guuccuuca auaguuugcc gggucacaag gcucauuacc cggucaagaa    6960
uccaauaggu aggaauuagc ucucuugagu acuaaaaaa cucuuuucag aauauaugau    7020
guuaccuucu ggucugaacu acgcacaagu guuguugugu gacuaguuaa guuggagggu    7080
ugcucaaaca accguccuug uucucccacc ugaccuucca gaugccguuu uccuaccuc    7140 auaggaguua gaugaccaau aaguuucucu ccgauuuuau ucuuugugac gacaguuuca    7200
gaaccguguu ccacuauuag uucaauaaac gugugucaua uuuugcuucu uuagcucuuu    7260
gcaacaucuu aaugcccac gagaguuagu uaccaaaga uauuacucu uuuaauacug    7320 acguuaguuu uaucccugue ccuucaauce ugaaaacuau uuacugcuac ucugauacgu    7380
```

-continued

```
uagacgucua augaacuuaa uaccuuuuua uggcuaaaag gcaccucacu aaucucccaa      7440
ucucugguuc ucuaccagug cucacugaac acagugguua cugguuuaug ggugaacacg      7500
auuauauuac ucgagucaaa gguguuuacg agaguggcau cgaguaaaac gacucuuggg      7560
uuaguuacgg uacuauguca uguuaauaaa acccuguaaa cgaucugaga caacuacua       7620 cguacuagga cgagaagcag uuaguaacau acuucaaguu cuauucuaug cccgaacgu       7680 gucaagauga aaguuuaugc gguacaacau aaaccuggga agguaaccuc cucacagccc      7740
guacagaaac agguccaaaa acuaaucucg gaagggucua gggcauuguc uuucagagag      7800
uaagaccucu aaguagguac auguacgagc uucacucgua gacuuccucu acucacguca      7860
uaaaccuuug gggcucuauc gguucaaagc uuauugagug uaucuguucg aucaucuucu      7920
agguuggaga gacuuguagc gauacccuua cucaggucgc uugaacaauu ucugaccuca      7980
auuuuuuacg aauuagcuua guucuguuug guaguccuug guccacuaau uccuacguug      8040
guauauaaac auaguacuuc uccuagccga gucuucaaag aauaccaguu auuuaggaga      8100
caagggaucu aaaaauucac uuaaguuuag uccgugaaaa aacccucagc gucugcccga      8160
guagucagau aaaguuuuaa gagcaugaua agccuugagg aaauucuuuu ucauaguauc      8220
ccuuaaccua cuaacuaac acuccucacu ccauaggaga aacuguguaa aucccuuuga       8280
aguaaacucu uccccuagua cauuuuacac cuguacaagu cgaugaguac gacuuguaa       8340 uucuauguuu aggaccccgg caugucaaua acccuguuga caugggguag guaaucuuua      8400
caacccaggu guuguagcuu uucucugagg aacacguggu acauugugua gucccaaguu      8460
aauacaaaga cacgaacag gucugcccua gguacgcag aaaucaagug ccccugguaa        8520
cggacgaaua gauccccagau uuuguagacu uagauguaga uaaaacgucg gaacccuuuc    8580
ccuuucguuu cagggugacu aauuuuccg augugcagaa ucucuacgau agagaaccaa      8640
acaacuuggg cugagauuug aucguuacug auaugaaaga uuguagguga gaaauuguc     8700 gcuucuuacc ugguuuuccg ucguacccaa guuuucuugu cccagacggg aaguauccaa    8760
aagcuguaga gccacucgg uaccacccaa gcguagaguc ucgugacguc guaacugguc     8820
caacuaccgu ugaugucugu gguaccuccu agcccucuua gucuuaaagc ugaaaaauaa    8880
gguucguugc aacgagauac gaguuuaaug guggugacaa cguucucugc cuaccuagug     8940
gucaacaugu cuaguaauag uauaacggac auucaggaca aacucugggu ucuucucua      9000 gugggaccug aguucauacc ugaugugcgg gggucuacau aggguacacg acuucuguac    9060
cuccuuaccc cuuccaagca ccccuguucu cuauuuuguc uagauaggaa aucuucccuu    9120
aaccuucuua aaucguggac gacucguuag gauaguucag ccgucuacau auccaaaaga    9180
uauaccucug aaccgcauau cuuuuagaug aguacggcuc cugucaagag auaaaggaga    9240
uagauauguu ccagcauaau cuccagcucc aaagaauuuu cccaacgauc ugccuaauua    9300
cucucguuca acgacgguuc auuaugggc cucuucagac cgaguaaacu ucuccggccg      9360
guugcgucac augccuccaa acuaaaugaa cuaacuauuu aacucacaua guggagguaa    9420
ggaaagagaa ugaucuaguc cuggauaauc ucugcuuaau cuuugcuaag ggguguucua    9480
ggguuggagg auaggcuguu cguuggcacu auaccccac uaacagucuu uaaugaaguu      9540
uaugguuacg gcagauuaac uuuucccuuu augucuagu guauaagug uuauaccaa        9600 uaagagcuca cagaauaggu aucgaagua accgguaag agauaaaggu ggugggagaa      9660
cguuuaggau auguucggua aaauagacc cuucuauuc uuacucaacu cucucgaccg      9720
uuuagaaaga aguaacgauu cuagucucu ccccacccuu cuguauguac acuuuaagaa     9780
```

| | | | | |
|---|---|---|---|---|
| gugguuccug | uauaauaaca | caggucuccu | uuagucugua | cgaacguuca agcccuaacg 9840 |
| auuccuauua | uuauuucugu | acucgauagg | gggaaccccu | ucccuuaggu cucccuguua 9900 |
| auguuguuag | ggacaaauaa | uaugcuggug | gggaaugggu | uucuacgauc ucuacggagg 9960 |
| uucuuagguu | uuaggggacg | acaggccuua | guccaacccg | guuaaugguu gaccgcgagu 10020 |
| aauauuuuaa | gccucauaua | auguaccuua | cccuuaggua | augcccuga agaacucaac 10080 |
| accucugccg | aggccucccu | acugacgacg | uaaugaugcu | cuuuuacacg uaucgucucc 10140 |
| uuauaaguua | ucagacaauc | uuaauagucc | cagucaguac | gcuccgcgga gaggacucgg 10200 |
| ggggucacgg | gaucuuugaa | auccuccucu | auuuagcucu | acacauuuac cacuuuguac 10260 |
| aacccuuaua | gguagacuga | auacacuggg | uuccugaacc | cugauaaagg aggcugaguu 10320 |
| ucguccgaac | cccgaaguuu | aacuaaauua | acauuaccua | uaccuucaag cccuaagaag 10380 |
| augaucggac | uuuuaacucu | gcuuacaauc | uuuaauacac | guggccuaaa accuacucgu 10440 |
| uccucaaaau | uagauguucu | gaauaccuug | uauauaaaca | cucucgcuuu ucuuacguca 10500 |
| uuguuaggaa | ccaggguaca | aguucugcca | gcugaaucaa | guugucuua aaucaucaag 10560 |
| aguuugcaga | cuucauauau | accauacauu | uccaaacuuc | uuuaauuagc uacuuggguu 10620 |
| agggcuaacc | agaagguagu | uacuuaggac | cuuuuuggac | augcguaagg ucaguagucu 10680 |
| uguccuuaaa | cggucucguu | ucuuccaauc | auguaugaaa | uggaacuguc cauaagggag 10740 |
| gguuaaguaa | ggacuaggaa | aacauuugua | acucugauac | gauguuuaua agccucaugg 10800 |
| gugcccacac | agaguacgcc | gacgaauuu | uaguagacua | ucggacguc uaaauaacug 10860 |
| guaaucggaa | aaaauauacc | gcuaauauag | cauaauauug | uaguuaguau agucucaucc 10920 |
| uggcuaugga | ggcuuggggg | guagucuacc | uuaacguguu | uuacaccccu agcgauauug 10980 |
| accauauucg | aaaaccgacu | caaacuaccu | cuuucuguaa | ggugauauag uugucacaaa 11040 |
| ucgucaauag | gucguuagua | agggcuaauc | cacccuccga | caaagucauu uuccuccuau 11100 |
| guucgucuuc | accucaugau | cuccacuacc | cgagggu uuu | cuaugggcuu aaagucugag 11160 |
| gaaccgggu | uagcccuuga | ccuagucuag | agaccuuaac | caggcuuugg uucaagcaga 11220 |
| uuuagguaag | uuacucuaga | acaaguuagu | cgauacagca | ugucaccuau uaguaaacuu 11280 |
| uaccaguuua | aacgcuucuu | uguguccuua | cuaacuuacc | uaguuaucug cuuaaaguuu 11340 |
| ucuucuggcc | agauaugacu | acaacuucuc | acuggaugug | cuccuuuuga gaaccucucu 11400 |
| aauuuuuuag | uacuccucug | agguuugaaa | uucauacuuu | uuuugaaacu aggaauucug 11460 |
| ggagaacacc | aaaaauaaaa | aauagaccaa | aacaccagaa | gcaucggacg aguuccgacu 11520 |